(12) United States Patent
Kawa et al.

(10) Patent No.: US 8,329,884 B2
(45) Date of Patent: Dec. 11, 2012

(54) **REAGENTS AND METHODS FOR DETECTING *NEISSERIA GONORRHOEAE***

(75) Inventors: Diane Kawa, San Marcos, CA (US); Shi-Da Lu, San Jose, CA (US); Peter Dailey, Clayton, CA (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 0 days.

(21) Appl. No.: 13/293,489

(22) Filed: Nov. 10, 2011

(65) Prior Publication Data

US 2012/0115148 A1 May 10, 2012

Related U.S. Application Data

(63) Continuation-in-part of application No. 12/908,791, filed on Nov. 8, 2010, now Pat. No. 8,071,303, which is a continuation of application No. 11/873,324, filed on Oct. 16, 2007, now Pat. No. 7,842,794, which is a continuation-in-part of application No. 11/017,476, filed on Dec. 17, 2004, now abandoned.

(51) Int. Cl.
*C07H 21/04* (2006.01)
*C12Q 1/68* (2006.01)

(52) U.S. Cl. .................. 536/23.1; 536/24.3; 536/24.32; 435/6.1; 435/6.11; 435/6.12; 435/6.15

(58) Field of Classification Search ........................ None
See application file for complete search history.

(56) References Cited

U.S. PATENT DOCUMENTS

| | | | |
|---|---|---|---|
| 5,389,515 A | 2/1995 | Chmelo et al. | |
| 5,550,040 A | 8/1996 | Purohit et al. | |
| 5,834,591 A | 11/1998 | Normark et al. | |
| 6,171,785 B1 | 1/2001 | Higuchi | |
| 7,157,564 B1 | 1/2007 | Mittmann et al. | |
| 2005/0158768 A1 | 7/2005 | Kawa et al. | |

FOREIGN PATENT DOCUMENTS

| EP | 08017887 | 5/2009 |
|---|---|---|
| WO | WO 02/079243 A3 | 10/2002 |

OTHER PUBLICATIONS

*Chlamydia trachomatis* genome, GenBank No. NC_000117 provided at http://www.ncbi.nlm.nih.gov as of Aug. 26,2005.
Crotchfelt et al. (1997) "Detection of *Neisseria gonorrhoea* and *Chlamydia trachomatis* in genitourinary specimens from men and woman by a coamplification PCR assay" *Journal of Clinical Microbiology* 35(6): 1536-1540.
Didomenico et al. (1996) "COBAS AMPLICOR™: a fully automated RNA and DNA amplification and detection system for routine diagnostic PCR." *Clinical Chemistry* 42(12): 1915-1923.
Diemert et al. (2002) "Confirmation by 16s rRNA PCR of the COBAS Amplicor CT/NG test for diagnosis of *Neisseria gonorrhoea* infection in a low-prevalence population." *Journal of Clinical Microbiology*, 40(11) 4056-4059.
Drosten et al. (2001) "TaqMan 5'-Nuclease Human Immunodeficiency Virus Type 1 PCR Assay with phage-packaged competitive internal control for high-throughput blood donor screening." *Journal of Clinical Microbiology*, 39(12): 4302-4308.
Farrell. (1999) "Evaluation of AMPLICOR *Neisseria gonorrhoea* PCR using *ccB* nested PCR and 16S rRNA PCR." *Journal of Clinical Microbiology*, 37(2) 386-390.
Jungkind et al. (1996) "Evaluation of automated COBAS AMPLICOR™ PCR system for detection of several infectious agents and its impact on laboratory management." *Journal of Clinical Microbiology* 34(11):2778-2783.
Kalman et al. (1999) "Comparative genomes of *Chlamydia pneumoniae* and *C. trachomatis*." *Nature Genetics* 21(4):385-389.
Leoffelholz et al. (1992) "Detection of *Chlamydia trachomatis* in endocervical specimens by polymerase chain reaction." *Journal of Clinical Microbiology* 30(11): 2847-2851.
*Neisseria gonorrhoeae* genome, Los Alamos National Laboratory Sexually Transmitted Diseases database provided at www.stdgen.lanl.gov/stdgen/bacteria/ngon/ as of Mar. 12, 2004.
Roe et al. (2004) "*Neisseria gonorrhoeae* Genome Sequencing" The Gonococcal Genome Sequencing Project at the University of Oklahoma, GenBank™ Accession No. AE004969; Feb. 19, 2004; p. 1-4 www.genome.ou.edu/gono.html.
Schweitzer and Kingsmore (2001) "Combining Nucleic Acid Amplification and Detection." *Current Opinion in Biotechnology*, 12:21-27.
Seib et al. (2004) "Defenses against oxidative stress in *Neisseria gonorrhoeae* and *Neisseria meningitidis*: distinctive systems for different lifestyles." *Journal of Infectious Diseases* 190(1) 136-47.
Stephens et al. (1998) "Genome sequence of an obligate intracellular pathogen of humans: *Chlamydia trachomatis*." *Science* 282:754-759.
Tinsley et al. (1996) "Analysis of the genetic differences between *Neisseria meningitidis* and *Neisseria gonorrhoae*: Two closely related bacteria expressing two different pathogenicities." Proc Natl. Acad. Science USA 93, 11109-11114.
Van Der Pol et al. (2000) "Multicenter Evaluation of the AMPLICOR and Automated COBAS AMPLICOR CT/NG tests for detection of *Chlamydia trachomatis.*" *Journal of Clinical Microbiology* 38(3): 1105-1112.
Van Doornum et al. (2001) "Comparison between the LCx Probe System and the COBAS AMPLICOR system for detection of *C. trachomatis* and *N. gonorrhoeae* infections in patients attending a clinic for treatment of sexually transmitted diseases in Amsterdam, the Netherlands." *Journal of Clinical Microbiology* 39(3) 829-835.
Whitcombe et al. (1999) "Detection of PCR products using self-probing amplicons and fluorescence." *Nature Biotechnology* 17:804-807.

*Primary Examiner* — Albert Navarro
(74) *Attorney, Agent, or Firm* — M. Reza Savari

(57) ABSTRACT

This invention provides compositions and methods for detecting *Neisseria gonorrhoeae* in a sample. This invention also provides related reaction mixtures, kits, systems, and computers.

9 Claims, 33 Drawing Sheets

Fig. 1

```
     G T T T T G C C G T C G G T T T T G T T G C T A C T G T T T G C A T T T T G T T  Majority(SEQ IN NO: 28)
     ---------+---------+---------+---------+
             210       220       230       240
     ---------+---------+---------+---------+
201  G T T T T G C C G T C G G T T T T G T T G C T A C T G T T T G C A T T T T G T T  NGDR9(SEQ IN NO: 1)
  1  . . . . . . . . . . . . . . . . . . . . . . . . . . . . . . . . . . . . . . . .  1117(SEQ IN NO: 29)
  1  . . . . . . . . . . . . . . . . . . . . . . . . . . . . . . . . . . . . . . . .  1120(SEQ IN NO: 30)
  2  . . . . . . . . . . . . . . . . . . . . . . . . . . . . . . . . . . . . . . . .  6346(SEQ IN NO: 31)
  7  . . . . . . . . . . . . . . . . . . . . . . . . . . . . . . . . . . . . . . . .  6359(SEQ IN NO: 32)
  7  . . . . . . . . . . . . . . . . . . . . . . . . . . . . . . . . . . . . . . . .  6364(SEQ IN NO: 33)

NG519 Upstream primer →
     T T C T C G A T T T T T T T G A T G C C C G T T C T C T C A A T G C C C A A T C A T  Majority(SEQ IN NO: 28)
     ---------+---------+---------+---------+
             250       260       270       280
     ---------+---------+---------+---------+
241  T T C T C G A T T T T T T T G A T G C C C G T T C T C T C A A T G C C C A A T C A T  NGDR9(SEQ IN NO: 1)
 24  . . . . . . . . . . . . . . . . . . . . . . . . . . . . . . . . . . . . . . . . .  1117(SEQ IN NO: 29)
 17  . . . . . . . . . . . . . . . . . . . . . . . . . . . . . . . . . . . . . . . . .  1120(SEQ IN NO: 30)
 42  . . . . . . . . . . . . . . . . . . . . . . . . . . . . . . . . . . . . . . . . .  6346(SEQ IN NO: 31)
 47  . . . . . . . . . . . . . . . . . . . . . . . . . . . . . . . . . . . . . . . . .  6359(SEQ IN NO: 32)
 47  . . . . . . . . . . . . . . . . . . . . . . . . . . . . . . . . . . . . . . . . .  6364(SEQ IN NO: 33)
```

Fig. 1 Cont.

| | | | |
|---|---|---|---|
| A A A G C T G T A T C T C T C A C G A G G T C G C C G A A T T T A A A A T T G A T | Majority | (SEQ IN NO: 28) |
| 290 | 300 | 310 | 320 |

```
       A A A G C T G T A T C T C T C A C G A G G T C G C C G A A T T T A A A A T T G A T    NGDR9(SEQ IN NO:  1)
281    A A A G C T G T A T C T C T C A C G A G G T C G C C G A A T T T A A A A T T G A T    NGDR9(SEQ IN NO:  1)
 64    . . . . . . . . . . . . . . . . . . . . . . . . . . . . . . . . . . . . . . . .    1117 (SEQ IN NO: 29)
 57    . . . . . . . . . . . . . . . . . . . . . . . . . . . . . . . . . . . . . . . .    1120 (SEQ IN NO: 30)
 82    . . . . . . . . . . . . . . . . . . . . . G . . . . . . . . . . . . . . . . . .    6346 (SEQ IN NO: 31)
 87    . . . . . . . . . . . . . . . . . . . . . . . . . . . . . . . . . . . . . . . .    6359 (SEQ IN NO: 32)
 87    . . . . . . . . . . . . . . . . . . . . . G . . . . . . . . . . . . . . . . . .    6364 (SEQ IN NO: 33)

A G T T C A T G T C T T G T T C C A T T A A T A T C A A A C G C A A T C T T C A    Majority(SEQ IN NO: 28)
                          330                 340                 350                 360
321    A G T T C A T G T C T T G T T C C A T T A A T A T C A A A C G C A A T C T T C A    NGDR9(SEQ IN NO:  1)
104    . . . . . . . . . . . . . . . . . . . . . . . . . . . . . . . . . . . . . . . .    1117 (SEQ IN NO: 29)
 97    . . . . . . . . . . . . . . . . . . . . . . . . . . . . . . . . . . . . . . . .    1120 (SEQ IN NO: 30)
122    . . . . . . . . . . . . . . . . . . . . . . . . . . . . . . . . . . . . . . . .    6346 (SEQ IN NO: 31)
127    . . . . . . . . . . . . . . . . . . . . . . . . . . . . . C . . . . . . . . . .    6359 (SEQ IN NO: 32)
127    . . . . . . . . . . . . . . . . . . . . . . . . . . . . . . . . . . . . . . . .    6364 (SEQ IN NO: 33)

A A C A C C T C A A T T A C A T T T T T T A A A A T C G C T A A T A C C A T A A T    Majority(SEQ IN NO: 28)
                          370                 380                 390                 400
361    A A C A C C T C A A T T A C A T T T T T T A A A A T C G C T A A T A C C A T A A T    NGDR9(SEQ IN NO:  1)
144    . . . . . . . . . . . . . . . . . . . . . . . . . . . . . . . . . . . . . . . .    1117 (SEQ IN NO: 29)
137    . . . . . . . . . . . . . . . . . . . . . . . . . . . . . . . . . . . . . . . .    1120 (SEQ IN NO: 30)
162    . . . . . . . . . . . . . . . . . . . . . . . . . . . . . . . . . . . . . . . .    6346 (SEQ IN NO: 31)
167    . . . . . . . . . . . . . . . . . . . . . . . . . . . . . . . . . . . C . . . .    6359 (SEQ IN NO: 32)
167    . . . . . . . . . . . . . . . . . . . . . . . . . . . . . . . . . . . . . . . .    6364 (SEQ IN NO: 33)
```

```
641 CAATCTTCGCGCCCTGCTACTTGCCGACCGCTTTCAATCGC        Majority (SEQ ID NO: 28)
          ----+----|----+----|----+----|----+----|
              650       660       670       680
          ----+----|----+----|----+----|----+----|
370                                                 NGDR9 (SEQ ID NO: 1)
375                                                 1117  (SEQ ID NO: 29)
400                                                 1120  (SEQ ID NO: 30)
405                                                 6346  (SEQ ID NO: 31)
405                                                 6359  (SEQ ID NO: 32)
                                                    6364  (SEQ ID NO: 33)

681 TTTTCTGATGGCGGTTTTGTCCGGTTCGGTTTTGACGGCC        Majority (SEQ ID NO: 28)
          ----+----|----+----|----+----|----+----|
              690       700       710       720
          ----+----|----+----|----+----|----+----|
370                                                 NGDR9 (SEQ ID NO: 1)
375                                                 1117  (SEQ ID NO: 29)
400                                                 1120  (SEQ ID NO: 30)
405                                                 6346  (SEQ ID NO: 31)
405                                                 6359  (SEQ ID NO: 32)
                                                    6364  (SEQ ID NO: 33)
```

Fig. 1 Cont.

```
                                                                                      Majority
       ------+---------+---------+---------+---------+---------+---------+
               730       740       750       760
721    T C A C G C A T A A A T T C G G C G G G G A T T T G C T T C G T C T A A G A    NGDR9(SEQ IN NO: 1)
370                                                                                    1117(SEQ IN NO: 29)
375                                                                                    1120(SEQ IN NO: 30)
400                                                                                    6346(SEQ IN NO: 31)
405                                                                                    6359(SEQ IN NO: 32)
405                                                                                    6364(SEQ IN NO: 33)

Majority
       ------+---------+---------+---------+---------+---------+---------+
               770       780       790       800
761    T C A C G A C G G C T T C G G A T T T G C G G A A C G A G G C T T T A A A A G T   NGDR9(SEQ IN NO: 1)
370                                                                                    1117(SEQ IN NO: 29)
375                                                                                    1120(SEQ IN NO: 30)
400                                                                                    6346(SEQ IN NO: 31)
405                                                                                    6359(SEQ IN NO: 32)
405                                                                                    6364(SEQ IN NO: 33)

Majority

801    G C C G T C                                                                     NGDR9(SEQ IN NO: 1)
370                                                                                    1117(SEQ IN NO: 29)
375                                                                                    1120(SEQ IN NO: 30)
400                                                                                    6346(SEQ IN NO: 31)
405                                                                                    6359(SEQ IN NO: 32)
405                                                                                    6364(SEQ IN NO: 33)
```

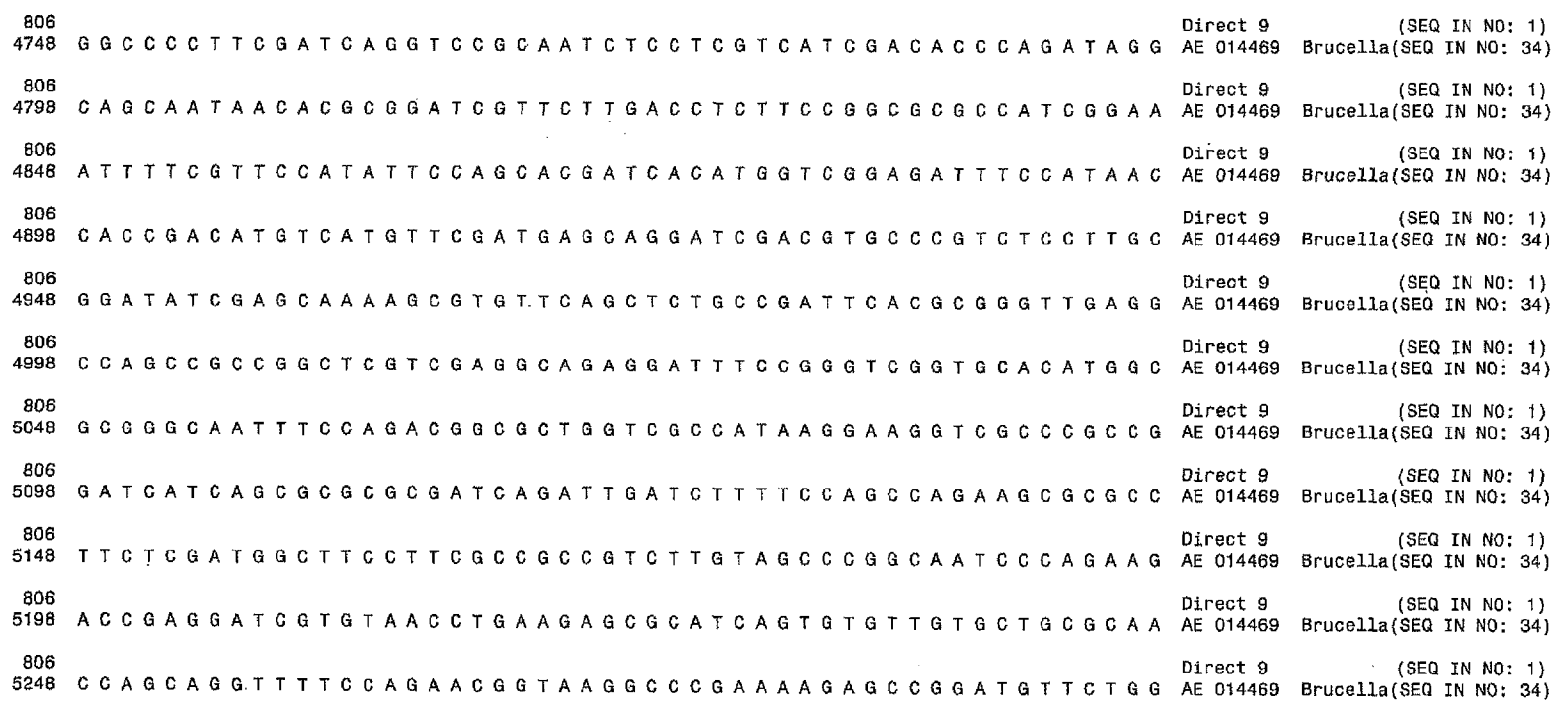

| Position | Sequence | Source | | |
|---|---|---|---|---|
| 806 4748 | GGCCCCTTCGATCAGGTCCGCAATCTCCTCGTCATCGGACACCCAGATAGG | Direct 9 AE 014469 | Brucella | (SEQ I

| Lane | ID |
|---|---|
| 1 | Mwt 20 bp |
| 2 | NG2072 |
| 3 | " |
| 4 | NM450 |
| 5 | " |
| 6 | LP 5700 |
| 7 | " |
| 8 | Neg |
| 9 | " |
| 10 | Mwt 20 bp |

NG = N. gonorrhoeae
NM = N. meningitidis
LP = L. pneumophila
Neg = Negative Control
Mwt 20 bp = Molecular Weight Standard

```
(SEQ ID NO: 2)Direct 33     TCGGCGCGTATCTCCGGCGATGCCCATTGCGTTCATTTCTT      0
(SEQ ID NO:35)AE002435      ---------------------------------------------  4840

(SEQ ID NO: 2)Direct 33     CGGGCAAAATCGACCGGGTTGCCTTTGAGCCTTTGCAGGGC      0
(SEQ ID NO:35)AE002435      ---------------------------------------------  4880

(SEQ ID NO: 2)Direct 33     GGAAATCATTTTCGGCGCGCCGACCAGTTTTGCCGGCGCC      0
(SEQ ID NO:35)AE002435      ---------------------------------------------  4920

(SEQ ID NO: 2)Direct 33     GCATCGGGCGCGGTATTCGCGTTGTCGGCTGAACCACATGA      0
(SEQ ID NO:35)AE002435      ---------------------------------------------  4960

(SEQ ID NO: 2)Direct 33     CAATTAAGCTGGCCAAGGAAGCCGAACAGGATTTGGAATAC      0
(SEQ ID NO:35)AE002435      ---------------------------------------------  5000

(SEQ ID NO: 2)Direct 33     CATGCTGACCAGGAAAATAAGTTCCCTGGGACTGGCTGCCG      0
(SEQ ID NO:35)AE002435      ---------------------------------------------  5040

(SEQ ID NO: 2)Direct 33     TCGTTTGTTTCGGGCAATCAGGTTGGCAATAATGCGCGACA      0
(SEQ ID NO:35)AE002435      ---------------------------------------------  5080

(SEQ ID NO: 2)Direct 33     GGAACACGACAAAGGTATTGACCACGCCTTGAATCAGCGT      0
(SEQ ID NO:35)AE002435      ---------------------------------------------  5120

(SEQ ID NO: 2)Direct 33     CAGCGTAACCATATCGCCCGTTGCCGACGTGTGCCATTTCG      0
(SEQ ID NO:35)AE002435      ---------------------------------------------  5160

(SEQ ID NO: 2)Direct 33     TGCGCCAATACGGCTTCCACTTCGTCACGCGTCATATGGT      0
(SEQ ID NO:35)AE002435      ---------------------------------------------  5200
                                          *Direct Repeat 33 Start →
(SEQ ID NO: 2)Direct 33     CGAGCAAACCGGTGCTG--ACGCCGTGGTGCGGCCTGTTTGT     23
(SEQ ID NO:35)AE002435      .........G..ATCA.G..AG......C.                 5240

(SEQ ID NO: 2)Direct 33     CGGATACTGCCTGGGCAAAAGC----------GGACGCGCG     54
(SEQ ID NO:35)AE002435      ....G.GC..GT.....G.....G.....ATTGGGTTC..GG..A..T. 5279
```

```
(SEQ ID NO: 2)Direct 33    GGGGAAGTGTCGGCATTCCCCCGATTTTTTACAT-ATC    986
(SEQ ID NO:35)AE002435     .AA.A..CC..GAAA.AA.G..TT.CCG...AC..CG.G.  6314

(SEQ ID NO: 2)Direct 33    GGGCGGACGC---GGCAAATTTTTGCCGT---TTTGTTTG  1020
(SEQ ID NO:35)AE002435     AAAA.C...A.TTTT..TCG.....A.A.CAAAC.G.AAG. 6354

(SEQ ID NO: 2)Direct 33    CGCGAAAGGGGGCGTTATACA--AAATTATCAGGCGCACCA  1058
(SEQ ID NO:35)AE002435     ..AAC.C.C.TAA....TC...G.TGAC...A.C.A.     6394

(SEQ ID NO: 2)Direct 33    ATAAATGG----GCGGAAATGAAAATGCCGTACCGATCCG   1093
(SEQ ID NO:35)AE002435     GC.G..A..AAGCC.T.A..GCCG..G.ATT.GG.GC..TG. 6434

(SEQ ID NO: 2)Direct 33    GACAACAACC----GATGCCGCACCCTGCGGGCAGGCTTC  1129
(SEQ ID NO:35)AE002435     .CA..T..ATCGAAA.G.T..T....A.............  6473

←Direct Repeat 33 Stop*
(SEQ ID NO: 2)Direct 33    GCACTCTGAAAGG                             1142
(SEQ ID NO:35)AE002435     .........ACAGAAAAATCAGGTTTTCAGACGACCTGT   6513
```

Fig. 8 Cont.

Gel C

| Lane | ID | Lane | ID |
|---|---|---|---|
| 1 | Mwt 20 bp | 14 | Mwt 20 bp |
| 2 | NG2949 | 15 | NG3534 |
| 3 | " | 16 | " |
| 4 | NSP2627 | 17 | NSS2631 |
| 5 | " | 18 | " |
| 6 | NC3308 | 19 | NM450 |
| 7 | " | 20 | " |
| 8 | NG3533 | 21 | NG1922 |
| 9 | " | 22 | " |
| 10 | NSS840 | 23 | NC82 |
| 11 | " | 24 | " |
| 12 | Neg | 25 | Neg |
| 13 | " | 26 | " |

NG= N. gonorrhoeae
NM =N. meningitidis
NC=N. cinerea
NF=N. flavescens
NK= N. kochi
NS= N. sicca
NSF= N. subflava biovar flava
NSP= N. subflava biovar perflava
NSS= N. subflava biovar subflava/flava
Neg = Negative Control
Mwt 20 bp = Molecular Weight Standard

Alignment of NGDR9Var sequence and NGDR9 sequence and *N. gonorrhoeae* strains

```
              NG545Hind (NGDR9Univ) (SEQ ID NO: 59) Pos Ctrl Upstream →
          ----+----+----+----+----+----+----+----+
                   10        20        30        40
    1 C A G C C G C A T C A T G A T G C C G C A C G T C A G G C T T C G T C T T C C    NGDR9Var (SEQ ID NO: 36)
    1 . . . . . . . . . . . . . . . . . . . . . . . . . . . . . . . . . . . . . . .    1137  (SEQ ID NO: 61)
    1 . . . . . . . . . . . . . . . . . . . . . . . . . . . . . . . . . . . . . . .    6676  (SEQ ID NO: 62)
    1 . . . . . . . . . . . . . . . . . . . . . . . . . . . . . . . . . . . . . . .    6677  (SEQ ID NO: 63)
    1 . . . . . . . . . . . . . . . . . . . . . . . . . . . . . . . . . . . . . . .    6864A (SEQ ID NO: 64)
    1 . . . . . . . . . . . . . . . . . . . . . . . . . . . . . . . . . . . . . . .    NGDR9 (SEQ ID NO: 1)
    1 . . . . . . . . . . . . . . . . . . . . . . . . . . . . . . . . . . . . . . .    2072  (SEQ ID NO: 65)
    1 - - - - - - - . . . . . . . . . . . . . . . . . . . . . . . . . . . . . . . .    3533  (SEQ ID NO: 66)
    1 . . . . . . . . . . . . . . . . . . . . . . . . . . . . . . . . . . . . . . .    6864B (SEQ ID NO: 67)

----+----+----+----+----+----+----+----+
                   50        60        70        80
   41 G A T A C C T T T G C G C C C G A C A A C A T C C G G G C G A T G T T T T C T T    NGDR9Var (SEQ ID NO: 36)
   41 . . . . . . . . . . . . . . . . . . . . . . . . . . . . . . . . . . . . . . .    1137  (SEQ ID NO: 61)
   26 . . . . . . . . . . . . . . . . . . . . . . . . . . . . . . . . . . . . . . .    6676  (SEQ ID NO: 62)
   41 . . . . . . . . . . . . . . . . . . . . . . . . . . . . . . . . . . . . . . .    6677  (SEQ ID NO: 63)
   41 . . . . . . . . . . . . A . . . . . . . . . . . . . . . . . . . . . . . . . .    6864A (SEQ ID NO: 64)
   41 . . . . . . . . . . . . A . . . . . . . . . . . . . . . . . . . . . . . . . .    NGDR9 (SEQ ID NO: 1)
   41 . . . . . . . . . . . . . . . . . . . . . . . . . . . . . . . . . . . . . . .    2072  (SEQ ID NO: 65)
   35 . . . . . . . . . . . . . . . . . . . . . . . . . . . . . . . . . . . . . . .    3533  (SEQ ID NO: 66)
   41 . . . . . . . . . . . . . . . . . . . . . . . . . . . . . . . . . . . . . . .    6864B (SEQ ID NO: 67)

----+----+----+----+----+----+----+----+
                   90       100       110       120
   81 T T T G C G C T T T T G A C C G G A C A G C C G G T T C C G G T C A A C          NGDR9Var (SEQ ID NO: 36)
   81 . . . . . . . . . . . . . . . . . . . . . . . . . . . . . . . . . . .          1137  (SEQ ID NO: 61)
   66 . . . . . . . . . . . . . . . . . . . . . . . . . . . . . . . . . . .          6676  (SEQ ID NO: 62)
   81 . . . . . . . . . . . . . . . . . . . . . . . . . . . . . . . . . . .          6677  (SEQ ID NO: 63)
   81 . . . . . . . . . . . . . . . . . . . . . . . . . . . . . . . . . . .          6864A (SEQ ID NO: 64)
   81 . . . . . . . . . . . . . . . . . . . . . . . . . . . . . . . . . . .          NGDR9 (SEQ ID NO: 1)
   81 . . . . . . . . . . . . . . . . . . . . . . . . . . . . . . . . . . .          2072  (SEQ ID NO: 65)
   75 . . . . . . . . . . . . . . . . . . . . . . . . . . . . . . . . . . .          3533  (SEQ ID NO: 66)
   81 . . . . . . . . . . . . . . . . . . . . . . . . . . . . . . . . . . .          6864B (SEQ ID NO: 67)
```

Amplification and detection of Neisserial Genomic DNA using NGDR9Var primers NG579 and NG552.

| Gel A | | | | | Gel B | | | |
|---|---|---|---|---|---|---|---|---|
| Lane | ID | Lane | ID | | Lane | ID | Lane | ID |
| 1 | Mwt 100 bp | 14 | NG2948 | | 1 | Mwt 100 bp | 14 | NM348 |
| 2 | NG2072 | 15 | " | | 2 | NG889 | 15 | " |
| 3 | " | 16 | NG2949 | | 3 | " | 16 | NM349 |
| 4 | NG2075 | 17 | " | | 4 | NG1137 | 17 | " |
| 5 | " | 18 | NG3533 | | 5 | " | 18 | NM350 |
| 6 | NG1922 | 19 | " | | 6 | NG6676 | 19 | " |
| 7 | " | 20 | NG3534 | | 7 | " | 20 | NC832 |
| 8 | NG2077 | 21 | " | | 8 | NG6677 | 21 | " |
| 9 | " | 22 | Neg | | 9 | " | 22 | Neg |
| 10 | NG2079 | 23 | " | | 10 | NM346 | 23 | " |
| 11 | " | 24 | NG FA1090 | | 11 | " | 24 | NG FA1090 |
| 12 | NG2080 | 25 | " | | 12 | NM347 | 25 | " |
| 13 | " | 26 | 100 bp | | 13 | " | 26 | 100 bp |

NG = N. gonorrhoeae
NM = N. meningitidis
NC = N. cinerea

Fig. 12B
Amplification and detection of Neisserial Genomic DNA using NGDR9Var primers NG579 and NG552.

| Gel A | | | |
|---|---|---|---|
| Lane | ID | Lane | ID |
| 1 | Mwt 100 bp | 14 | NSP2627 |
| 2 | NF920 | 15 | " |
| 3 | " | 16 | NSS840 |
| 4 | NK2039 | 17 | " |
| 5 | " | 18 | NSS2631 |
| 6 | NL539 | 19 | " |
| 7 | " | 20 | NC3306 |
| 8 | NS839 | 21 | " |
| 9 | " | 22 | Neg |
| 10 | NS929 | 23 | " |
| 11 | " | 24 | NG FA1090 |
| 12 | NSF2738 | 25 | " |
| 13 | " | 26 | 100 bp |

| Gel B | | |
|---|---|---|
| Lane | ID | |
| 1 | Mwt 100 bp | NG = N. gonorrhoeae |
| 2 | NC3307 | NM = N. meningitidis |
| 3 | " | NC = N. cinerea |
| 4 | NC3308 | NF = N. flavescens |
| 5 | " | NK = N. kochi |
| 6 | NG6864 | NS = N. sicca |
| 7 | " | NL = N. lactamica |
| 8 | NM450 | NSF = N. subflava biovar flava |
| 9 | " | NSP = N. subflava biovar perflava |
| 10 | Neg | NSS = N. subflava biovar subflava/flava |
| 11 | " | |
| 12 | 100bp | |

Fig. 13A
Amplification and detection of Neisserial Genomic DNA using NGDR9Univ primers NGSU2 and NGSL2

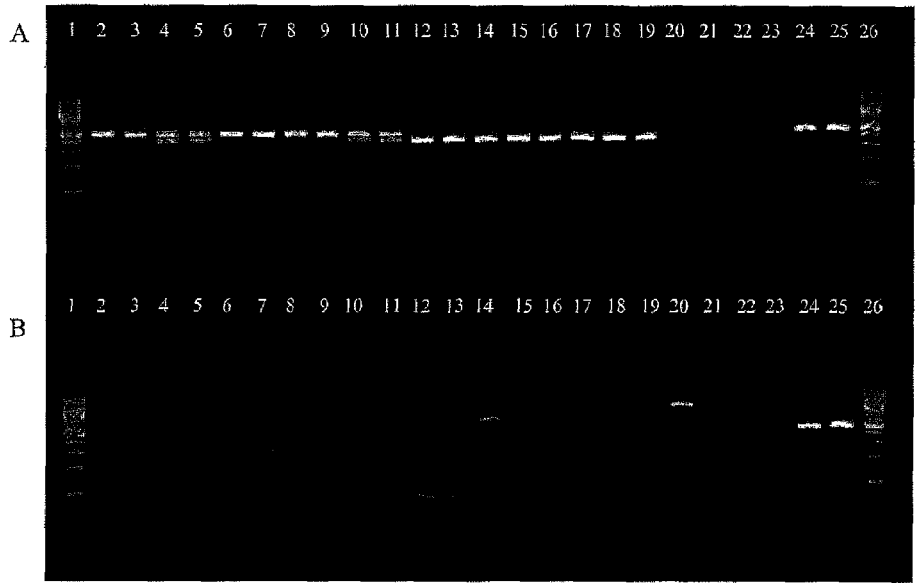

| Gel A | | | |
|---|---|---|---|
| Lane | ID | Lane | ID |
| 1 | Mwt 100 bp | 14 | NG1137 |
| 2 | NG2072 | 15 | " |
| 3 | " | 16 | NG6676 |
| 4 | NG2075 | 17 | " |
| 5 | " | 18 | NG6677 |
| 6 | NG1922 | 19 | " |
| 7 | " | 20 | NM346 |
| 8 | NG2077 | 21 | " |
| 9 | " | 22 | Neg |
| 10 | NG3534 | 23 | " |
| 11 | " | 24 | NG FA1090 |
| 12 | NG889 | 25 | " |
| 13 | " | 26 | 100 bp |

| Gel B | | | |
|---|---|---|---|
| Lane | ID | Lane | ID |
| 1 | Mwt 100 bp | 14 | NS839 |
| 2 | NM347 | 15 | " |
| 3 | " | 16 | NS929 |
| 4 | NM349 | 17 | " |
| 5 | " | 18 | NSF2738 |
| 6 | NM350 | 19 | " |
| 7 | " | 20 | NSP2627 |
| 8 | NF920 | 21 | " |
| 9 | " | 22 | Neg |
| 10 | NK2039 | 23 | " |
| 11 | " | 24 | NG FA1090 |
| 12 | NL539 | 25 | " |
| 13 | " | 26 | 100 bp |

NG = N. gonorrhoeae
NM = N. meningitidis
NF = N. flavescens
NK = N. kochi
NS = N. sicca
NL = N. lactamica
NSF = N. subflava biovar flava
NSP = N. subflava biovar perflava

Amplification and detection of Neisserial Genomic DNA using NGDR9Univ primers NGSU2 and NGSL2

Gel A

| Lane | ID | Lane | ID |
|---|---|---|---|
| 1 | Mwt 100 bp | 14 | Neg |
| 2 | NSS840 | 15 | " |
| 3 | " | 16 | NG FA1090 |
| 4 | NSS2631 | 17 | " |
| 5 | " | 18 | 100 bp |
| 6 | NC3306 | | |
| 7 | " | | |
| 8 | NC3307 | | |
| 9 | " | | |
| 10 | NC3308 | | |
| 11 | " | | |
| 12 | NG6864 | | |
| 13 | " | | |

NG = N. gonorrhoeae
NC = N. cinerea
NSS = N. subflava biovar subflava/flava

REAGENTS AND METHODS FOR DETECTING *NEISSERIA GONORRHOEAE*

CROSS-REFERENCES TO RELATED APPLICATIONS

This application is a continuation-in-part of application Ser. No. 12/908,791 filed Nov. 8, 2010, which is a continuation of application Ser. No. 11/873,324 filed Oct. 16, 2007 now U.S. Pat. No. 7,842,794, which is a continuation-in-part of application Ser. No. 11/017,476 filed Dec. 17, 2004, the disclosures of which are incorporated by reference in their entirety for all purposes.

FIELD OF THE INVENTION

The present invention relates to the fields of molecular biology and nucleic acid chemistry. The invention provides methods and reagents for detecting pathogens, such as *Neisseria gonorrhoeae* and accordingly, also relates to the fields of medical diagnostics and prognostics.

BACKGROUND OF THE INVENTION

The genus *Neisseria* consists of Gram-negative aerobic bacteria including the human pathogen *N. gonorrhoeae*, which is the causative agent of gonorrhea. *N. gonorrhoeae* infections, which have a high prevalence and low mortality, are generally acquired by sexual contact and typically affect mucous membranes of the urethra in males and the endocervix in females. However, the infection may also spread to other tissues. For example, a genital infection in males can ascend the urethra and produce symptoms of prostatitis, whereas in females, an *N. gonorrhoeae* infection of the cervix may spread to the fallopian tubes and ultimately cause sterility among other conditions, if untreated. The pathogenic mechanism of *N. gonorrhoeae* involves the attachment of the bacterium to nonciliated epithelial cells via pili. The mechanism also includes the production of endotoxin and IgA proteases.

Co-infection of *N. gonorrhoeae* and *Chlamydia trachomatis* is frequently observed. Both infections are two known causes of ectopic pregnancy and can also lead to infertility if untreated. They are also known causes of the acute clinical syndromes of mucopurulent cervicitis and pelvic inflammatory disease. Therefore, the detection of *N. gonorrhoeae* and *C. trachomatis* infections, which can be asymptomatic, especially in females, is of consequence to individuals in need of treatment and to broader populations at risk of acquiring and further propagating the infections.

The detection and identification of bacterial infections has traditionally been accomplished by pure culture isolation and determination procedures that make use of knowledge of specimen source, growth requirements, visible growth features, microscopic morphology, staining reactions, and biochemical characteristics. For example, pre-existing methods of detecting and identifying *N. gonorrhoeae* infections, include Gram-staining, culturing on selective agar media, and cytochrome oxidase and carbohydrate utilization testing. Serological assays, including coagglutination and fluorescent antibody staining have also been described for the detection of *N. gonorrhoeae*. Culture-based methods, while relatively sensitive, are generally slow to perform, often including overnight incubation, and are labor intensive. The Gram-stain and antibody-based tests typically provide results in less than one hour, but are generally of lower sensitivity than culture-based methods.

The use of specific polynucleotide sequences as probes for the recognition of infectious agents is one alternative to problematic immunological identification assays and other pre-existing methodologies. For example, nucleic acid probes complementary to targeted nucleic acid sequences have been used in hybridization procedures, such as Southern blots and dot blots, to detect the target nucleic acid sequence. Many of these hybridization procedures have depended on the cultivation and/or enrichment of the organism and, thus, are unsuitable for rapid diagnosis. The advent of techniques for the rapid amplification of specific nucleic acid sequences, such as the polymerase chain reaction among many others, have provided a mechanism to use sequence specific probes directly on clinical specimens, thereby eliminating enrichment and in vitro culturing of the pathogen prior to performing the hybridization assay. Thus, amplification-based hybridization assays can provide simple and rapid diagnostic techniques for the detection of pathogens in clinical samples.

Many probes used to date lack sufficient specificity to differentiate between pathogenic agents having highly homologous nucleic acid sequences, such as *N. gonorrhoeae*, *N. meningitidis*, and the like. This can lead to biased assay results, including false positives. One consequence of such misdiagnosis may be the administration of an inappropriate course of treatment to a patient.

SUMMARY OF THE INVENTION

The present invention provides methods and reagents for the rapid detection of *Neisseria gonorrhoeae* that are species specific, that is, without substantial detection of other species in the *Neisseria* genus or species from other genera. For example, the nucleic acid detection reagents of the invention (e.g., probe nucleic acids, sequence specific antibodies, etc.) typically bind to nucleotide sequences present in *N. gonorrhoeae* but not in other species. Further, since patients infected with *N. gonorrhoeae* are often also infected with *Chlamydia trachomatis*, the invention also provides methods of concurrently detecting *N. gonorrhoeae* and *C. trachomatis* in samples. This approach minimizes the number of diagnostic procedures to which a patient is subjected, which also typically minimizes the overall cost of diagnosis. In addition to compositions and reaction mixtures, the invention also relates to kits and systems for detecting these pathogenic agents, and to related computer and computer readable media.

In one aspect, the invention provides an oligonucleotide consisting of a nucleic acid with a sequence selected from the group consisting of: SEQ ID NOS: 3-27, 37-60, 68-70, or complements thereof. In another aspect, the invention provides an oligonucleotide comprising a nucleic acid with a sequence selected from the group consisting of: SEQ ID NOS: 3-27, 37-60, 68-70, and complements thereof, which oligonucleotide has 100 or fewer nucleotides. In still another aspect, the invention provides an oligonucleotide that includes a nucleic acid having at least 90% sequence identity (e.g., at least 95%, etc.) to one of SEQ ID NOS: 3-27, 37-60, 68-70, or a complement thereof, which oligonucleotide has 100 or fewer nucleotides. Typically, these oligonucleotides are primer nucleic acids, probe nucleic acids, or the like in these embodiments. In certain of these embodiments, the oligonucleotides have 40 or fewer nucleotides (e.g., 35 or fewer nucleotides, 30 or fewer nucleotides, etc.). In some embodiments, the oligonucleotides comprise at least one modified nucleotide. Optionally, the oligonucleotides comprise at least one label and/or at least one quencher moiety. In some embodiments, the oligonucleotides include at least one conservatively modified variation.

In another aspect, the invention relates to an oligonucleotide comprising at least 90% sequence identity with a subsequence of SEQ ID NO: 1, SEQ ID NO: 2, SEQ ID NO: 36, or the complement thereof, which oligonucleotide has 100 or fewer nucleotides. In certain embodiments, the oligonucleotide has a sequence between about 12 and about 50 nucleotides in length. In some embodiments, at least one nucleotide of the oligonucleotide is modified to alter nucleic acid hybridization stability relative to unmodified nucleotides. In certain embodiments, the oligonucleotide comprises at least one label and/or at least one quencher moiety. In some embodiments, a solid support comprises the oligonucleotide.

In another aspect, the invention provides a method of detecting Neisseria gonorrhoeae in a sample, which method includes (a) contacting nucleic acids from the sample with at least a first pair of primer nucleic acids that selectively bind to a nucleic acid with a sequence consisting of SEQ ID NO: 1, SEQ ID NO: 2, SEQ ID NO: 36, a substantially identical variant thereof in which the variant has at least 90% sequence identity to one of SEQ ID NOS: 1 or 2 or 36, or a complement of SEQ ID NO: 1, SEQ ID NO: 2, SEQ ID NO: 36 or the variant, in at least one nucleic acid amplification reaction. The method also includes (b) detecting the nucleic acids and/or one or more amplicons thereof from the nucleic acid amplification reaction during or after (a), thereby detecting the Neisseria gonorrhoeae in the sample. In certain embodiments, for example, the nucleic acids and/or the amplicons thereof comprise at least one sequence selected from the group consisting of: SEQ ID NOS: 28-33. In some embodiments, (a) comprises contacting the nucleic acids from the sample with at least a second pair of primer nucleic acids that are at least partially complementary to a Chlamydia trachomatis nucleic acid. In these embodiments, (b) comprises detecting one or more additional amplicons from the nucleic acid amplification reaction during or after (a), thereby detecting Chlamydia trachomatis in the sample. In certain embodiments, at least one of the primer nucleic acids comprises a modified primer nucleic acid. In some embodiments, at least one of the primer nucleic acids comprises at least one label. In these embodiments, (b) optionally comprises detecting a detectable signal produced by the label, or amplifying a detectable signal produced by the label to produce an amplified signal and detecting the amplified signal. In some embodiments, (b) comprises monitoring binding between the amplicons and one or more nucleic acid detection reagents that detectably bind to a nucleic acid with a sequence consisting of SEQ ID NO: 1, SEQ ID NO: 2, SEQ ID NO: 36, a substantially identical variant thereof in which the variant has at least 90% sequence identity to one of SEQ ID NOS: 1 or 2 or 36, or a complement of SEQ ID NO: 1, SEQ ID NO: 2, SEQ ID NO: 36 or the variant. Typically, at least one of the nucleic acid detection reagents comprises at least one label and/or at least one quencher moiety. In these embodiments, (b) optionally comprises detecting a detectable signal produced by the label, or amplifying a detectable signal produced by the label to produce an amplified signal and detecting the amplified signal.

In another aspect, the invention provides a method of determining a presence of Neisseria gonorrhoeae in a sample, which method comprises (a) contacting nucleic acids and/or amplicons thereof from the sample with one or more oligonucleotides that selectively bind to a nucleic acid with a sequence consisting of SEQ ID NO: 1, SEQ ID NO: 2, SEQ ID NO: 36, a substantially identical variant thereof in which the variant has at least 90% sequence identity to one of SEQ ID NOS: 1 or 2 or 36, or a complement of SEQ ID NO: 1, SEQ ID NO: 2, SEQ ID NO: 36 or the variant. The method also includes (b) monitoring (e.g., at a single time point, at multiple discrete time points, continuously over a selected time period, etc.) binding between the nucleic acids and/or amplicons thereof, and the oligonucleotides, in which detectable binding between the nucleic acids and/or amplicons thereof, and the oligonucleotides, determines the presence of Neisseria gonorrhoeae in the sample. In some embodiments, for example, the nucleic acids and/or the amplicons thereof comprise at least one sequence selected from the group consisting of: SEQ ID NOS: 28-33. The presence of Neisseria gonorrhoeae in the sample is generally unknown or unsubstantiated before (a). In certain embodiments, (a) comprises contacting the nucleic acids and/or amplicons thereof with the oligonucleotides in solution at a temperature of at least 42° C. for at least 15 minutes in which a total weight of the solution comprises about 50% formalin and comprises heparin at a concentration of about 1 mg/ml. Moreover, the method typically comprises a reaction other than a sequencing reaction. The sample is generally derived from a mammalian subject, such as a human subject. In certain embodiments, the nucleic acids and/or amplicons thereof and the oligonucleotides are contacted in solution. Optionally, a solid support comprises the nucleic acids and/or amplicons (e.g., arrayed on the solid support). As an additional option, a solid support comprises the oligonucleotides.

In certain embodiments of the invention, the method further includes contacting the nucleic acids and/or amplicons thereof from the sample with at least one additional oligonucleotide that detectably binds to a Chlamydia trachomatis nucleic acid. In these embodiments, the method also includes monitoring the binding between the nucleic acids and/or amplicons thereof and the additional oligonucleotide, thereby detecting Chlamydia trachomatis in the sample. In some embodiments, the method includes repeating (a) and (b) at least once using at least one additional sample (e.g., from the same subject) and comparing the binding between the nucleic acids and/or amplicons thereof, and the oligonucleotides, of (b) with at least one repeated (b) to monitor, e.g., the course of treatment for a subject diagnosed with a Neisseria gonorrhoeae and/or a Chlamydia trachomatis infection, the recurrence of the infection, or the like.

The nucleic acid detection reagents of the invention include various embodiments. To illustrate, at least one of the nucleic acid detection reagents may comprise an oligonucleotide (e.g., a probe nucleic acid, a primer nucleic acid, etc.). Typically, the oligonucleotide comprises at least 85% (e.g., about 90%, about 95%, etc.) sequence identity with a subsequence of SEQ ID NO: 1, SEQ ID NO: 2, SEQ ID NO: 36, a substantially identical variant thereof in which the variant has at least 90% sequence identity to one of SEQ ID NOS: 1 or 2 or 36, or a complement of SEQ ID NO: 1, SEQ ID NO: 2, SEQ ID NO: 36 or the variant. In some of these embodiments, (b) comprises monitoring binding between the oligonucleotide and the nucleic acid and/or amplicons thereof. Optionally, the oligonucleotide has a sequence between about 8 and about 100 nucleotides in length. In certain embodiments, the oligonucleotide has a sequence selected from the group consisting of: SEQ ID NOS: 3-27, 37-60, and 68-70, a substantially identical variant thereof in which the variant has at least 90% sequence identity to one of SEQ ID NOS: 3-27, 37-60, and 68-70, and complements of SEQ ID NOS: 3-27, 37-60, and 68-70, and the variant. Optionally, at least one nucleotide of the oligonucleotide is modified. In some embodiments, for example, the nucleotide is modified to alter nucleic acid hybridization stability relative to unmodified nucleotides.

To further illustrate, at least one of the nucleic acid detection reagents optionally detectably binds to a nucleic acid segment that comprises one or more nucleotide positions of SEQ ID NO: 1 selected from the group consisting of: 259, 260, 262, 264, 265, 266, 268, 269, 273, 275, 276, 277, 279, 297, 298, 300, 301, 302, 303, 304, 305, 306, 308, 313, 314, 315, 316, 317, 318, 320, 321, 325, 326, 428, 429, 431, 432, 433, 434, 435, 440, 441, and 447. As an additional option, at least one of the nucleic acid detection reagents detectably binds to a nucleic acid segment that comprises one or more nucleotide positions of SEQ ID NO: 2 selected from the group consisting of: 89, 90, 91, 92, 95, 98, 101, 105, 106, 107, 216, 217, 220, 222, 223, 225, 233, 235, 236, 238, 335, 336, 337, 338, 339, 342, 345, 346, and 351. In other embodiments, at least one of the nucleic acid detection reagents comprises, e.g., a sequence specific antibody.

In certain embodiments, the nucleic acids, the amplicons thereof, and/or the nucleic acid detection reagents comprise at least one label and/or at least one quencher moiety. For example, the label optionally comprises a fluorescent dye, a weakly fluorescent label, a non-fluorescent label, a colorimetric label, a chemiluminescent label, a bioluminescent label, an antibody, an antigen, biotin, a hapten, a mass-modifying group, a radioisotope, an enzyme, or the like. In these embodiments, (b) typically comprises detecting a detectable signal produced by the label. To illustrate, (b) optionally comprises (i) amplifying a detectable signal produced by the label to produce an amplified signal, and (ii) detecting the amplified signal.

In some embodiments, at least one segment of the nucleic acids is amplified prior to or during (a) using at least one nucleic acid amplification technique to produce the amplicons and (b) comprises monitoring the binding between the nucleic acids and/or amplicons thereof, and the nucleic acid detection reagents, during or after amplification. For example, the nucleic acid amplification technique typically comprises a polymerase chain reaction, a ligase chain reaction, and/or the like. In these embodiments, the segment is optionally amplified using at least one primer nucleic acid comprising a sequence selected from the group consisting of: SEQ ID NOS: 3-27, 37-60, and 68-70, a substantially identical variant thereof in which the variant has at least 90% sequence identity to one of SEQ ID NOS: 3-27, 37-60, and 68-70 and complements of SEQ ID NOS: 3-27, 37-60, and 68-70 and the variant. In some of these embodiments, the primer nucleic acid comprises at least one label, as described herein or otherwise known in the art. Optionally, the primer nucleic acid comprises a modified primer nucleic acid (e.g., a nucleic acid amplification specificity altering modification, a restriction site linker, and/or the like).

In another aspect, the invention relates to a method of detecting *Neisseria gonorrhoeae* in a sample. The method includes (a) contacting nucleic acids from the sample with at least a first pair of primer nucleic acids comprising at least one nucleic acid selected from the group consisting of: SEQ ID NOS: 3-27, 37-60, and 68-70, a substantially identical variant thereof in which the variant has at least 90% sequence identity to one of SEQ ID NOS: 3-27, 37-60, and 68-70, and complements of SEQ ID NOS: 3-27, 37-60, and 68-70, and the variant, in at least one nucleic acid amplification reaction. In addition, the method also includes (b) detecting the nucleic acids and/or one or more amplicons thereof from the nucleic acid amplification reaction during or after (a), thereby detecting the *Neisseria gonorrhoeae* in the sample. In certain embodiments, for example, the nucleic acids and/or the amplicons thereof comprise at least one sequence selected from the group consisting of: SEQ ID NOS: 28-33. The sample is typically derived from a mammalian subject, such as a human subject. Optionally, at least one of the primer nucleic acids comprises a modified primer nucleic acid. In some embodiments, for example, the modified primer nucleic acid comprises a nucleic acid amplification specificity altering modification and/or a restriction site linker modification. In certain embodiments, (a) comprises contacting the nucleic acids from the sample with at least a second pair of primer nucleic acids that are at least partially complementary to a *Chlamydia trachomatis* nucleic acid and (b) comprises detecting one or more additional amplicons from the nucleic acid amplification reaction during or after (a), thereby detecting *Chlamydia trachomatis* in the sample.

In some embodiments, at least one of the primer nucleic acids comprises at least one label. The label optionally comprises, e.g., a fluorescent dye, a weakly fluorescent label, a non-fluorescent label, a colorimetric label, a chemiluminescent label, a bioluminescent label, an antibody, an antigen, biotin, a hapten, a mass-modifying group, a radioisotope, an enzyme, etc. In these embodiments, (b) typically comprises detecting a detectable signal produced by the label. Optionally, (b) comprises (i) amplifying a detectable signal produced by the label to produce an amplified signal, and (ii) detecting the amplified signal.

In certain embodiments, (b) comprises monitoring binding between the amplicons and one or more nucleic acid detection reagents that specifically bind to a nucleic acid with a sequence consisting of SEQ ID NO: 1, SEQ ID NO: 2, SEQ ID NO: 36, a substantially identical variant thereof in which the variant has at least 90% sequence identity to one of SEQ ID NOS: 1 or 2 or 36, or a complement of SEQ ID NO: 1, SEQ ID NO: 2, SEQ ID NO: 36, or the variant. Optionally, at least one of the nucleic acid detection reagents comprises an oligonucleotide (e.g., a probe nucleic acid, etc.). In some of these embodiments, (b) comprises detecting hybridization between the oligonucleotide and the amplicons. Optionally, the oligonucleotide comprises a sequence between about 8 and about 100 nucleotides in length. In certain embodiments, at least one nucleotide of the oligonucleotide is modified (e.g., to alter nucleic acid hybridization stability relative to unmodified nucleotides or the like). For example, at least one of the nucleic acid detection reagents comprises a nucleic acid comprising a sequence selected from the group consisting of: SEQ ID NOS: 3-27, 37-60, and 68-70, a substantially identical variant thereof in which the variant has at least 90% sequence identity to one of SEQ ID NOS: 3-27, 37-60, and 68-70, and complements of SEQ ID NOS: 3-27, 37-60, and 68-70, and the variant. To further illustrate, at least one of the nucleic acid detection reagents optionally detectably binds to a nucleic acid segment that comprises one or more nucleotide positions of SEQ ID NO: 1 selected from the group consisting of: 259, 260, 262, 264, 265, 266, 268, 269, 273, 275, 276, 277, 279, 297, 298, 300, 301, 302, 303, 304, 305, 306, 308, 313, 314, 315, 316, 317, 318, 320, 321, 325, 326, 428, 429, 431, 432, 433, 434, 435, 440, 441, and 447. As an additional option, at least one of the nucleic acid detection reagents detectably binds to a nucleic acid segment that comprises one or more nucleotide positions of SEQ ID NO: 2 selected from the group consisting of: 89, 90, 91, 92, 95, 98, 101, 105, 106, 107, 216, 217, 220, 222, 223, 225, 233, 235, 236, 238, 335, 336, 337, 338, 339, 342, 345, 346, and 351. In some embodiments, at least one of the nucleic acid detection reagents comprises a sequence specific antibody or the like. Optionally, at least one of the nucleic acid detection reagents comprises at least one label and/or at least one quencher moiety. An exemplary label optionally comprises a fluorescent dye, a weakly fluorescent label, a non-fluorescent label, a colorimetric label, a chemiluminescent label, a bioluminescent label, an antibody, an antigen, biotin, a hapten, a mass-modifying group, a radioisotope, an enzyme, or the like. In these embodiments, (b) typically comprises detecting a detectable signal produced by the label. In some of these embodiments, (b) comprises (i) amplifying a detectable signal produced by the label to produce an amplified signal, and (ii) detecting the amplified signal.

In another aspect, the invention provides a method of detecting *Neisseria gonorrhoeae* in a sample in which the method includes (a) contacting nucleic acids from the sample with at least a first pair of primer nucleic acids in at least one nucleic acid amplification reaction, in which each of the primer nucleic acids have between 12 and 100 nucleotides, and in which at least one of the primer nucleic acids comprises at least 90% sequence identity with a subsequence of SEQ ID NO: 1, SEQ ID NO: 2, SEQ ID NO: 36, or a complement thereof. The method also includes (b) detecting the nucleic acids and/or one or more amplicons thereof from the nucleic acid amplification reaction during or after (a), thereby detecting the *Neisseria gonorrhoeae* in the sample. Typically, the presence of *Neisseria gonorrhoeae* in the sample is unknown or unsubstantiated before (a). In some embodiments, one or more of the primer nucleic acids has a sequence selected from the group consisting of: SEQ ID NOS: 3-27, 37-60, and 68-70, a substantially identical variant thereof wherein the variant has at least 90% sequence identity to one of SEQ ID NOS: 3-27, 37-60, and 68-70, and complements of SEQ ID NOS: 3-27, 37-60, and 68-70, and the variant.

In still another aspect, the invention relates to a method of determining a presence of *Neisseria gonorrhoeae* in a sample in which the method includes (a) contacting nucleic acids and/or amplicons thereof from the sample with at least one oligonucleotide that has between 12 and 100 nucleotides, which oligonucleotide comprises at least 90% sequence identity with a subsequence of SEQ ID NO: 1, SEQ ID NO: 2, SEQ ID NO: 36, or a complement thereof. In addition, the method also includes (b) monitoring binding between the nucleic acids and/or amplicons thereof, and the oligonucleotide, wherein detectable binding between the nucleic acids and/or amplicons thereof, and the oligonucleotide, determines the presence of *Neisseria gonorrhoeae* in the sample. Typically, the presence of *Neisseria gonorrhoeae* in the sample is unknown or unsubstantiated before (a). In certain embodiments, one or more of the primer nucleic acids has a sequence selected from the group consisting of: SEQ ID NOS: 3-27, 37-60, and 68-70, a substantially identical variant thereof wherein the variant has at least 90% sequence identity to one of SEQ ID NOS: 3-27, 37-60, and 68-70, and complements of SEQ ID NOS: 3-27, 37-60, and 68-70, and the variant.

In another aspect, the invention relates to a composition comprising a sample derived from a subject and one or more nucleic acid detection reagents that selectively bind to a nucleic acid with a sequence consisting of SEQ ID NO: 1, SEQ ID NO: 2, SEQ ID NO: 36, a substantially identical variant thereof in which the variant has at least 90% sequence identity to one of SEQ ID NOS: 1 or 2 or 36, or a complement of SEQ ID NO: 1, SEQ ID NO: 2, SEQ ID NO: 36, or the variant. A presence of *Neisseria gonorrhoeae* in the sample is generally unknown or unsubstantiated. Typically, the nucleic acid detection reagents comprise at least one chemically synthesized nucleic acid. In certain embodiments, at least one of the nucleic acid detection reagents comprises an oligonucleotide (e.g., a probe nucleic acid, a primer nucleic acid, or the like). Typically, the oligonucleotide comprises at least 85% (e.g., about 90%, about 95%, etc.) sequence identity with a subsequence of SEQ ID NO: 1, SEQ ID NO: 2, SEQ ID NO: 36, or the complement thereof. In some of these embodiments, the oligonucleotide has a sequence between about 8 and about 100 nucleotides in length (e.g., between about 12 and about 50 nucleotides in length). In certain embodiments, at least one nucleotide of the oligonucleotide is modified (e.g., to alter nucleic acid hybridization stability relative to unmodified nucleotides). For example, the nucleic acid detection reagents optionally comprise at least one nucleic acid having a sequence selected from the group consisting of: SEQ ID NOS: 3-27, 37-60, and 68-70, a substantially identical variant thereof in which the variant has at least 90% sequence identity to one of SEQ ID NOS: 3-27, 37-60, and 68-70, and complements of SEQ ID NOS: 3-27, 37-60, and 68-70, and the variant. To further illustrate, at least one of the nucleic acid detection reagents optionally detectably binds to a nucleic acid segment that comprises one or more nucleotide positions of SEQ ID NO: 1 selected from the group consisting of: 259, 260, 262, 264, 265, 266, 268, 269, 273, 275, 276, 277, 279, 297, 298, 300, 301, 302, 303, 304, 305, 306, 308, 313, 314, 315, 316, 317, 318, 320, 321, 325, 326, 428, 429, 431, 432, 433, 434, 435, 440, 441, and 447. As an additional option, at least one of the nucleic acid detection reagents detectably binds to a nucleic acid segment that comprises one or more nucleotide positions of SEQ ID NO: 2 selected from the group consisting of: 89, 90, 91, 92, 95, 98, 101, 105, 106, 107, 216, 217, 220, 222, 223, 225, 233, 235, 236, 238, 335, 336, 337, 338, 339, 342, 345, 346, and 351. In some embodiments, the nucleic acid detection reagents comprise at least one sequence specific antibody. In certain embodiments, the composition further includes at least one additional nucleic acid detection reagent that detectably binds to a *Chlamydia trachomatis* nucleic acid.

Typically, at least one of the nucleic acid detection reagents comprises at least one label and/or at least one quencher moiety. To illustrate, the label optionally comprises a fluorescent dye, a weakly fluorescent label, a non-fluorescent label, a colorimetric label, a chemiluminescent label, a bioluminescent label, an antibody, an antigen, biotin, a hapten, a mass-modifying group, a radioisotope, an enzyme, or the like.

The nucleic acid detection reagents of the compositions of the invention are provided in various formats. In some embodiments, for example, at least one of the nucleic acid detection reagents is in solution. In other embodiments, a solid support comprises at least one of the nucleic acid detection reagents. In these embodiments, the nucleic acid detection reagents are non-covalently or covalently attached to the solid support. Exemplary solid supports utilized in these embodiments are optionally selected from, e.g., a plate, a microwell plate, a bead, a microbead (e.g., a magnetic microbead, etc), a tube (e.g., a microtube, etc.), a fiber, a whisker, a comb, a hybridization chip, a membrane, a single crystal, a ceramic layer, a self-assembling monolayer, and the like.

To further illustrate, the nucleic acid detection reagents are optionally conjugated with biotin or a biotin derivative and the solid support is optionally conjugated with avidin or an avidin derivative, or streptavidin or a streptavidin derivative. In some embodiments, a linker attaches the nucleic acid detection reagents to the solid support. The linker is typically selected from, e.g., an oligopeptide, an oligonucleotide, an oligopolyamide, an oligoethyleneglycerol, an oligoacrylamide, an alkyl chain, and the like. Optionally, a cleavable attachment attaches the nucleic acid detection reagents to the solid support. The cleavable attachment is generally cleavable by, e.g., heat, an enzyme, a chemical agent, electromagnetic radiation, etc.

In other aspects, the invention provides a reaction mixture that includes a set of amplicons having sequences that correspond to subsequences of SEQ ID NO: 1, SEQ ID NO: 2, SEQ ID NO: 36, a substantially identical variant thereof in which the variant has at least 90% sequence identity to one of SEQ ID NOS: 1 or 2 or 36, or a complement of SEQ ID NO: 1, SEQ ID NO: 2, SEQ ID NO: 36, or the variant, which amplicons lack terminator nucleotides. Typically, at least a subset of the set of amplicons is produced using at least one primer nucleic acid having a sequence selected from the group consisting of: SEQ ID NOS: 3-27, 37-60, and 68-70, a substantially identical variant thereof in which the variant has at least 90% sequence identity to one of SEQ ID NOS: 3-27, 37-60, and 68-70, and complements of SEQ ID NOS: 3-27, 37-60, and 68-70, and the variant. In certain embodiments, the primer nucleic acid comprises a modified primer nucleic acid. For example, the modified primer nucleic acid optionally comprises a nucleic acid amplification specificity altering modification, a restriction site linker modification, and/or the like. In some embodiments, the reaction mixture further includes an additional set of amplicons that comprise sequences that correspond to a Chlamydia trachomatis nucleic acid sequence.

In another aspect, the invention provides a kit that includes (a) at least one oligonucleotide that has between 12 and 100 or few nucleotides, which oligonucleotide comprises at least 90% sequence identity with a subsequence of SEQ ID NO: 1, SEQ ID NO: 2, SEQ ID NO: 36, or a complement thereof; and one or more of: (b) instructions for determining a presence of Neisseria gonorrhoeae in a sample by monitoring binding between nucleic acids and/or amplicons thereof from the sample and the oligonucleotide in which the presence of Neisseria gonorrhoeae in the sample is unknown or unsubstantiated, or (c) at least one container for packaging at least the oligonucleotide. In some of these embodiments, the oligonucleotide has a sequence between about 8 and about 100 nucleotides in length. In certain embodiments, for example, the oligonucleotide has a sequence selected from the group consisting of: SEQ ID NOS: 3-27, 37-60, and 68-70, a substantially identical variant thereof in which the variant has at least 90% sequence identity to one of SEQ ID NOS: 3-27, 37-60, and 68-70, and complements of SEQ ID NOS: 3-27, 37-60, and 68-70, and the variant. To further illustrate, the oligonucleotide optionally detectably binds to a nucleic acid segment that comprises one or more nucleotide positions of SEQ ID NO: 1 selected from the group consisting of: 259, 260, 262, 264, 265, 266, 268, 269, 273, 275, 276, 277, 279, 297, 298, 300, 301, 302, 303, 304, 305, 306, 308, 313, 314, 315, 316, 317, 318, 320, 321, 325, 326, 428, 429, 431, 432, 433, 434, 435, 440, 441, and 447. As an additional option, the oligonucleotide detectably binds to a nucleic acid segment that comprises one or more nucleotide positions of SEQ ID NO: 2 selected from the group consisting of: 89, 90, 91, 92, 95, 98, 101, 105, 106, 107, 216, 217, 220, 222, 223, 225, 233, 235, 236, 238, 335, 336, 337, 338, 339, 342, 345, 346, and 351. In other embodiments, the nucleic acid detection reagent is a sequence specific antibody. In certain embodiments, the kit further includes one or more nucleic acid detection reagents that specifically bind to a Chlamydia trachomatis nucleic acid. In these embodiments, the kit typically further includes instructions for detecting Chlamydia trachomatis in the sample by monitoring binding between nucleic acids and/or amplicons thereof from the sample and the additional nucleic acid detection reagents, and/or one or more containers for packaging the additional nucleic acid detection reagents. In some embodiments, kit typically further includes at least one enzyme (e.g., a polymerase, etc.) and/or one or more nucleotides.

In some embodiments, the nucleic acid detection reagent is in solution, whereas in others, a solid support comprises the nucleic acid detection reagent. The solid support is optionally selected from, e.g., a plate, a microwell plate, a bead, a microbead, a tube, a fiber, a whisker, a comb, a hybridization chip, a membrane, a single crystal, a ceramic layer, a self-assembling monolayer, or the like.

Typically, the oligonucleotide comprises at least one label and/or at least one quencher moiety. Exemplary labels include, e.g., a fluorescent dye, a weakly fluorescent label, a non-fluorescent label, a colorimetric label, a chemiluminescent label, a bioluminescent label, an antibody, an antigen, biotin, a hapten, a mass-modifying group, a radioisotope, an enzyme, or the like.

In still other aspects, the invention provides a system (e.g., an automated system) for detecting Neisseria gonorrhoeae in a sample. The system includes (a) at least one oligonucleotide that has between 12 and 100 or few nucleotides, which oligonucleotide comprises at least 90% sequence identity with a subsequence of SEQ ID NO: 1, SEQ ID NO: 2, SEQ ID NO: 36, or a complement thereof. The system also includes (b) at least one detector that detects binding between nucleic acids and/or amplicons thereof from the sample and the oligonucleotide, and (c) at least one controller operably connected to the detector, which controller comprises one or more instructions sets that correlate the binding detected by the detector with a presence of Neisseria gonorrhoeae in the sample. The oligonucleotide typically has a sequence selected from the group consisting of: SEQ ID NOS: 3-27 and 37-60 or complements thereof. To further illustrate, the oligonucleotide optionally detectably binds to a nucleic acid segment that comprises one or more nucleotide positions of SEQ ID NO: 1 selected from the group consisting of: 259, 260, 262, 264, 265, 266, 268, 269, 273, 275, 276, 277, 279, 297, 298, 300, 301, 302, 303, 304, 305, 306, 308, 313, 314, 315, 316, 317, 318, 320, 321, 325, 326, 428, 429, 431, 432, 433, 434, 435, 440, 441, and 447. As an additional option, the oligonucleotide detectably binds to a nucleic acid segment that comprises one or more nucleotide positions of SEQ ID NO: 2 selected from the group consisting of: 89, 90, 91, 92, 95, 98, 101, 105, 106, 107, 216, 217, 220, 222, 223, 225, 233, 235, 236, 238, 335, 336, 337, 338, 339, 342, 345, 346, and 351. In addition, the oligonucleotide typically comprises at least one label and/or at least one quencher moiety. In certain embodiments, the system further includes one or more additional nucleic acid detection reagents that specifically bind to a Chlamydia trachomatis nucleic acid in which the detector detects binding between the nucleic acids and/or amplicons thereof from the sample and the additional nucleic acid detection reagents, and in which the controller comprises at least one instruction set that correlates the binding detected by the detector with a presence of Chlamydia trachomatis in the sample. In some embodiments, at least one container or solid support comprises the oligonucleotide. In these embodiments, the system optionally further includes (d) at least one thermal modulator operably connected to the container or solid support to modulate temperature in the container or on the solid support, and/or (e) at least one fluid transfer component that transfers fluid to and/or from the container or solid support, e.g., for performing one or more nucleic acid amplification techniques in the container or on the solid support, etc.

In another aspect, the invention provides a system that includes (a) computer or computer readable medium comprising a data set that comprises a plurality of character strings that correspond to a plurality of sequences that correspond to subsequences of SEQ ID NO: 1, SEQ ID NO: 2, SEQ ID NO: 36, a substantially identical variant thereof in which the variant has at least 90% sequence identity to one of SEQ ID NOS: 1 or 2 or 36, or a complement of SEQ ID NO: 1, SEQ ID NO: 2, SEQ ID NO: 36, or the variant. The system also includes (b) an automatic synthesizer coupled to an output of the computer or computer readable medium, which automatic synthesizer accepts instructions from the computer or computer readable medium, which instructions direct synthesis of one or more nucleic acids that correspond to one or more character strings in the data set. Typically, at least one of the character strings corresponds to a sequence selected from the group consisting of: SEQ ID NOS: 3-27, 37-60, and 68-70, or complements thereof.

BRIEF DESCRIPTION OF THE DRAWINGS

Figure 4:
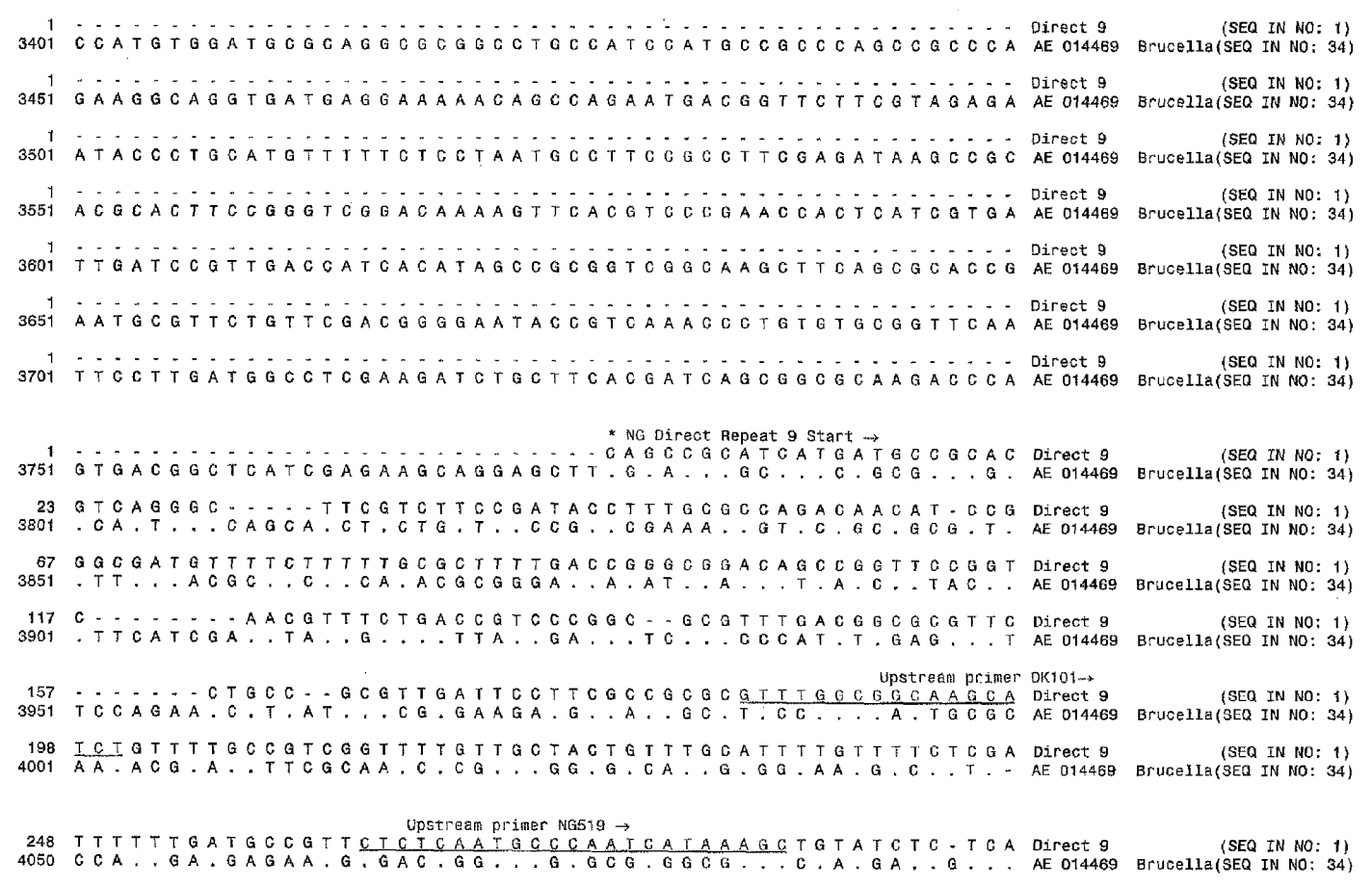
Figure 4:
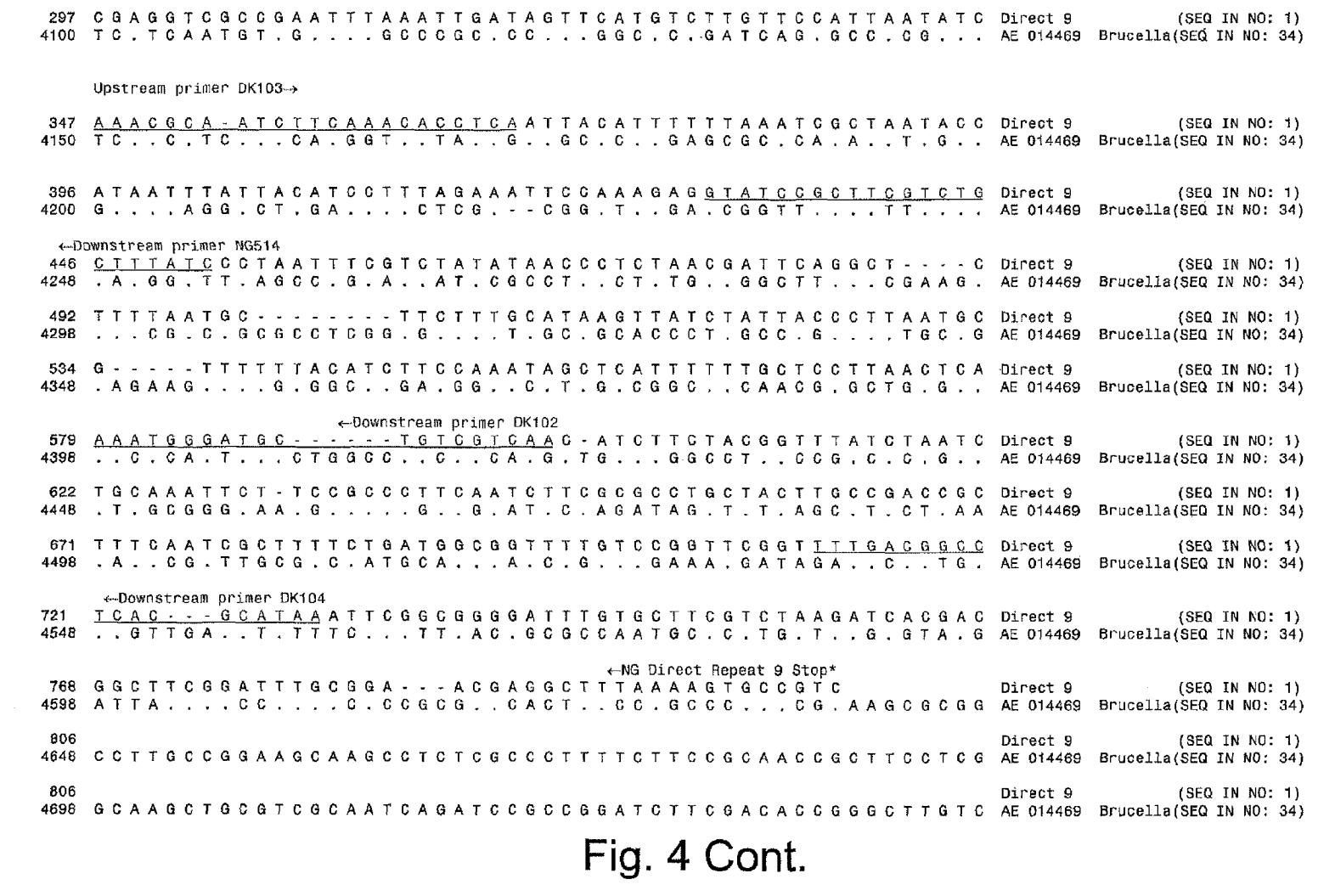

FIG. 4 shows a ClustalW alignment of the NGDR9 sequence (SEQ ID NO:1) with a portion (SEQ ID NO:34) of the sequence of *Brucella suis* 1330 chromosome I section 155 (GenBank® accession number AE014469).

FIG. 8 depicts a ClustalW alignment of the *Neisseria gonorrhoeae* Direct Repeat 33 (NGDR33) (SEQ ID NO:2) sequence with a portion (SEQ ID NO:35) of the sequence of *Neisseria meningitidis* serogroup B strain MC58 section 77 (GenBank® accession number AE002435).

FIGS. 12A and 12B are photographs of agarose gels that show the detection of a 215 base pair segment of NGDR9Var.

FIGS. 13A and 13B are photographs of agarose gels that show the simultaneous detection of a 473 base pair segment of NGDR9 and a 394 base pair segment of NGDR9Var.

DETAILED DESCRIPTION

I. Definitions

Figure 1:
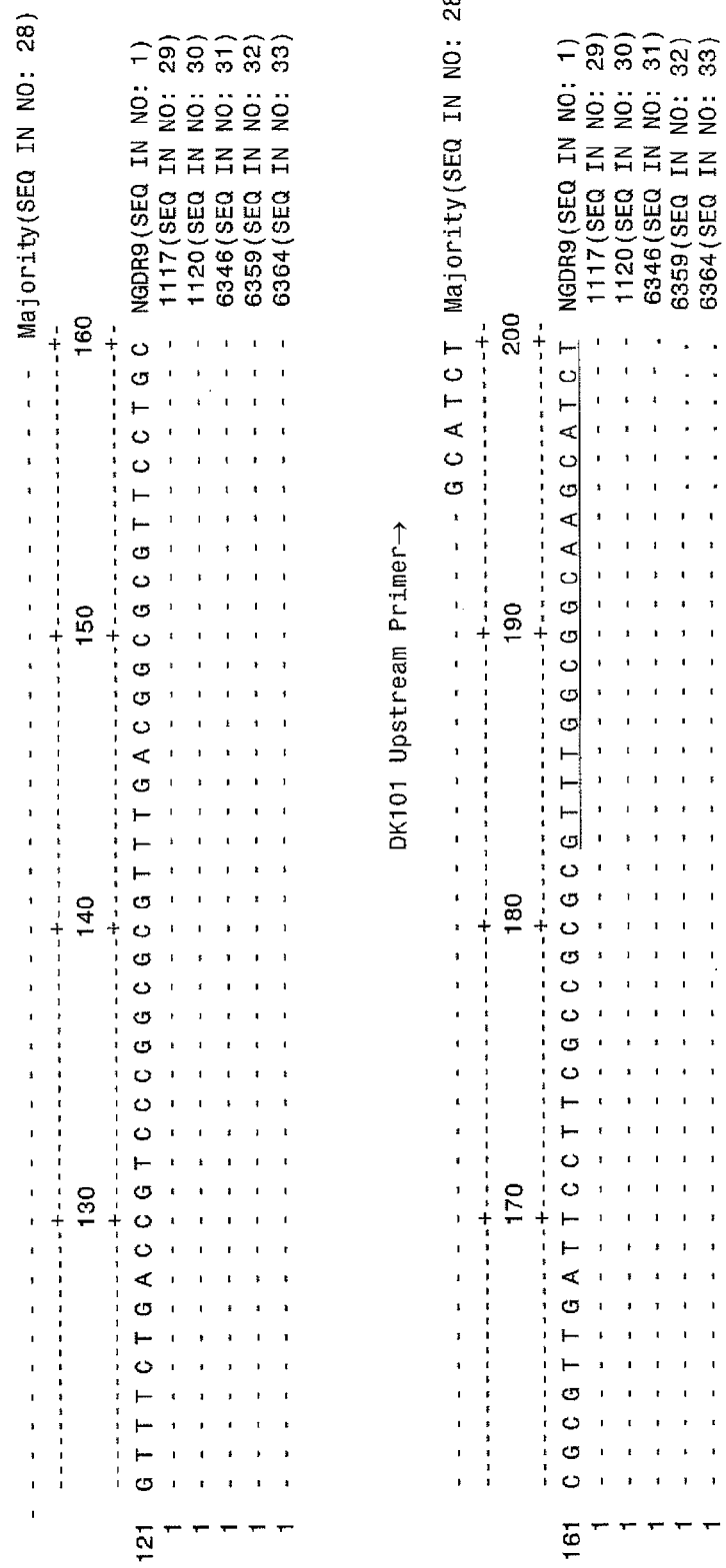
FIG. 1 shows a sequence alignment of a *Neisseria gonorrhoeae* Direct Repeat 9 (NGDR9) sequence (SEQ ID NO:1) with the sequences of amplicons of genomic DNA from various *N. gonorrhoeae* strains (strain 1117, SEQ ID NO:29; strain 1120, SEQ ID NO:30; strain 6346, SEQ ID NO:31; strain 6359, SEQ ID NO:32; and strain 6364, SEQ ID NO:33). The majority (consensus) sequence is SEQ ID NO:28.
Figure 1:
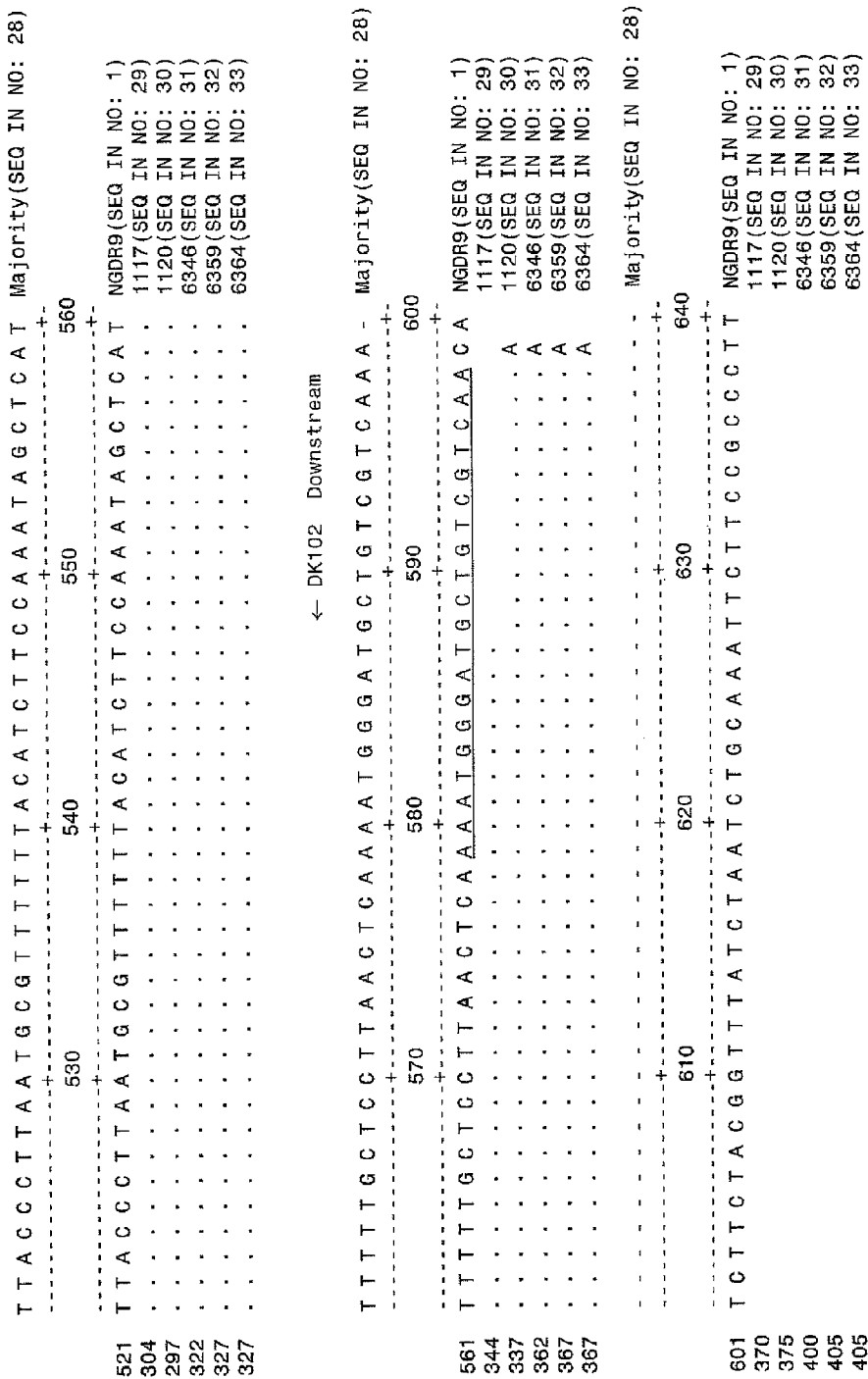

Before describing the present invention in detail, it is to be understood that this invention is not limited to particular oligonucleotide probes, methods, compositions, reaction mixtures, kits, systems, computers, or computer readable media, which can, of course, vary. It is also to be understood that the terminology used herein is for the purpose of describing particular embodiments only, and is not intended to be limiting. Further, unless defined otherwise, all technical and scientific terms used herein have the same meaning as commonly understood by one of ordinary skill in the art to which this invention pertains. In describing and claiming the present invention, the following terminology and grammatical variants will be used in accordance with the definitions set forth below.

A "5'-nuclease probe" refers to an oligonucleotide probe that comprises at least two labels and emits radiation of increased intensity after one of the two labels is cleaved or otherwise separated from the probe. In certain embodiments, for example, a 5'-nuclease probe is labeled with two different fluorescent dyes, e.g., a 5' terminus reporter dye and the 3' terminus quenching dye or moiety. When the probe is intact, energy transfer typically occurs between the two fluorophores such that fluorescent emission from the reporter dye is quenched. During an extension step of a polymerase chain reaction, for example, a 5'-nuclease probe bound to a template nucleic acid is cleaved by the 5' nuclease activity of, e.g., a Taq polymerase such that the fluorescent emission of the reporter dye is no longer quenched. Exemplary 5'-nuclease probes are described in, e.g., U.S. Pat. No. 5,210,015, entitled "HOMOGENEOUS ASSAY SYSTEM USING THE NUCLEASE ACTIVITY OF A NUCLEIC ACID POLYMERASE," issued May 11, 1993 to Gelfand et al., U.S. Pat. No. 5,994,056, entitled "HOMOGENEOUS METHODS FOR NUCLEIC ACID AMPLIFICATION AND DETECTION," issued Nov. 30, 1999 to Higuchi, and U.S. Pat. No. 6,171,785, entitled "METHODS AND DEVICES FOR HEMOGENEOUS NUCLEIC ACID AMPLIFICATION AND DETECTOR," issued Jan. 9, 2001 to Higuchi, which are each incorporated by reference.

The term "alteration" refers to a change in a nucleic acid sequence, including, but not limited to, a substitution, an insertion, and/or a deletion.

An "amplification reaction" refers to a primer initiated replication of one or more target nucleic acid sequences or complements thereto.

An "amplicon" refers to a molecule made by copying or transcribing another molecule, e.g., as occurs in transcription, cloning, and/or in a polymerase chain reaction ("PCR") (e.g., strand displacement PCR amplification (SDA), duplex PCR amplification, etc.) or other nucleic acid amplification technique. Typically, an amplicon is a copy of a selected nucleic acid (e.g., a template or target nucleic acid) or is complementary thereto.

An "amplified signal" refers to increased detectable signal that can be produced in the absence of, or in conjunction with, an amplification reaction. Exemplary signal amplification techniques are described in, e.g., Cao et al. (1995) "Clinical evaluation of branched DNA signal amplification for quantifying HIV type 1 in human plasma," *AIDS Res Hum Retroviruses* 11(3):353-361, and in U.S. Pat. No. 5,437,977 to Segev, U.S. Pat. No. 6,033,853 to Delair et al., and U.S. Pat. No. 6,180,777 to Horn, which are each incorporated by reference.

"Antibody" refers to a polypeptide substantially encoded by at least one immunoglobulin gene or fragments of at least one immunoglobulin gene, that can participate in detectable binding with a ligand. The term includes naturally-occurring forms, as well as fragments and derivatives. Fragments within the scope of the term as used herein include those produced by digestion with various peptidases, such as Fab, Fab' and F(ab)'2 fragments, those produced by chemical dissociation, by chemical cleavage, so long as the fragment remains capable of detectable binding to a target molecule, such as an antigen indicative of a disease.

An "array" refers to an assemblage of elements. The assemblage can be spatially ordered (a "patterned array") or disordered (a "randomly patterned" array). The array can form or comprise one or more functional elements (e.g., a probe region on a microarray) or it can be non-functional.

The term "attached" or "conjugated" refers to interactions and/or states in which material or compounds are connected or otherwise joined with one another. These interactions and/or states are typically produced by, e.g., covalent bonding, ionic bonding, chemisorption, physisorption, and combinations thereof. In certain embodiments, for example, oligonucleotide probes are attached to solid supports. In some of these embodiments, an oligonucleotide probe is conjugated with biotin (i.e., is biotinylated) and a solid support is conjugated with avidin such that the probe attaches to the solid support via the binding interaction of, e.g., biotin and avidin.

Molecular species "bind" when they associate with one another via covalent and/or non-covalent interactions. For example, two complementary single-stranded nucleic acids can hybridize with one another to form a nucleic acid with at least one double-stranded region. To further illustrate, antibodies and corresponding antigens can also non-covalently associate with one another.

The term "cleavage" refers to a process of releasing a material or compound from attachment to another material or compound. In certain embodiments, for example, oligonucleotides are cleaved from, e.g., a solid support to permit analysis of the oligonucleotides by solution-phase methods. See, e.g., Wells et al. (1998) "Cleavage and Analysis of Material from Single Resin Beads," *J. Org. Chem.* 63:6430, which is incorporated by reference.

A "character" when used in reference to a character of a character string refers to a subunit of the string. In one embodiment, the character of a character string encodes one subunit of an encoded biological molecule. Thus, for example, where the encoded biological molecule is a polynucleotide or oligonucleotide, a character of the string encodes a single nucleotide.

A "character string" is any entity capable of storing sequence information (e.g., the subunit structure of a biological molecule such as the nucleotide sequence of a nucleic acid, etc.). In one embodiment, the character string can be a simple sequence of characters (letters, numbers, or other symbols) or it can be a numeric or coded representation of such information in tangible or intangible (e.g., electronic, magnetic, etc.) form. The character string need not be "linear," but can also exist in a number of other forms, e.g., a linked list or other non-linear array (e.g., used as a code to generate a linear array of characters), or the like. Character strings are typically those which encode oligonucleotide or polynucleotide strings, directly or indirectly, including any encrypted strings, or images, or arrangements of objects which can be transformed unambiguously to character strings representing sequences of monomers or multimers in polynucleotides, or the like (whether made of natural or artificial monomers).

The term "*Chlamydia trachomatis*," "*C. trachomatis*," or "CT" refers the bacterial species *trachomatis* of the *Chlamydia* genus. See, e.g., Stephens et al. (1998) "Genome sequence of an obligate intracellular pathogen of humans: *Chlamydia trachomatis*," *Science* 282:754-759, Kalman et al. (1999) "Comparative genomes of *Chlamydia pneumoniae* and *C. trachomatis*," *Nature Genetics* 21:385-389, and Stephens, *Chlamydia: Intracellular Biology, Pathogenesis, and Immunity*, ASM Press (1999), which are each incorporated by reference. An exemplary GenBank® accession number for the complete sequence of the *Chlamydia trachomatis* genome is NC000117. See also, the *Chlamydia trachomatis* database, which is on the world wide web at stdgen.lanl.gov as of Mar. 12, 2004.

The term "*Chlamydia trachomatis* nucleic acid" or "*C. trachomatis* nucleic acid" refers to a nucleic acid (and/or an amplicon thereof) that is derived or isolated from *Chlamydia trachomatis*.

The term "complement thereof" refers to nucleic acid that is both the same length as, and exactly complementary to, a given nucleic acid.

A "composition" refers to a combination of two or more different components. In certain embodiments, for example, a composition includes a solid support that comprises one or more oligonucleotide probes, e.g., covalently or non-covalently attached to a surface of the support. In other embodiments, a composition includes one or more oligonucleotide probes in solution.

The term "deletion" in the context of a nucleic acid sequence refers to an alteration in which at least one nucleotide is removed from the nucleic acid sequence, e.g., from a 5'-terminus, from a 3'-terminus, and/or from an internal position of the nucleic acid sequence.

The term "derivative" refers to a chemical substance related structurally to another substance, or a chemical substance that can be made from another substance (i.e., the substance it is derived from), e.g., through chemical or enzymatic modification. To illustrate, oligonucleotide probes are optionally conjugated with biotin or a biotin derivative. To further illustrate, one nucleic acid can be "derived" from another through processes, such as chemical synthesis based on knowledge of the sequence of the other nucleic acid, amplification of the other nucleic acid, or the like.

The term "detectably bind" refers to binding between at least two molecular species (e.g., a probe nucleic acid and a target nucleic acid, a sequence specific antibody and a target nucleic acid, etc.) that is detectable above a background signal (e.g., noise) using one or more methods of detection.

Nucleic acids are "extended" or "elongated" when additional nucleotides (or other analogous molecules) are incorporated into the nucleic acids. For example, a nucleic acid is optionally extended by a nucleotide incorporating biocatalyst, such as a polymerase that typically adds nucleotides at the 3' terminal end of a nucleic acid.

An "extended primer nucleic acid" refers to a primer nucleic acid to which one or more additional nucleotides have been added or otherwise incorporated (e.g., covalently bonded thereto).

Nucleic acids "hybridize" or "bind" when they associate with one another, typically in solution. Nucleic acids hybridize due to a variety of well characterized physico-chemical forces, such as hydrogen bonding, solvent exclusion, base stacking and the like. An extensive guide to the hybridization of nucleic acids is found in Tijssen (1993) *Laboratory Techniques in Biochemistry and Molecular Biology—Hybridization with Nucleic Acid Probes* part I chapter 2, "Overview of principles of hybridization and the strategy of nucleic acid probe assays," (Elsevier, New York), as well as in Ausubel (Ed.) *Current Protocols in Molecular Biology*, Volumes I, II, and III, 1997, which is incorporated by reference. Hames and Higgins (1995) *Gene Probes* 1 IRL Press at Oxford University Press, Oxford, England, (Hames and Higgins 1) and Hames and Higgins (1995) *Gene Probes* 2 IRL Press at Oxford University Press, Oxford, England (Hames and Higgins 2) provide details on the synthesis, labeling, detection and quantification of DNA and RNA, including oligonucleotides. Both Hames and Higgins 1 and 2 are incorporated by reference.

"Stringent hybridization wash conditions" in the context of nucleic acid hybridization assays or experiments, such as nucleic acid amplification reactions, Southern and northern hybridizations, or the like, are sequence dependent, and are different under different environmental parameters. An extensive guide to the hybridization of nucleic acids is found in Tijssen (1993), supra. and in Hames and Higgins, 1 and 2.

For purposes of the present invention, generally, "highly stringent" hybridization and wash conditions are selected to be at least about 5° C. lower than the thermal melting point ($T_m$) for the specific sequence at a defined ionic strength and pH. The $T_m$ is the temperature (under defined ionic strength and pH) at which 50% of the test sequence hybridizes to a perfectly matched probe. Very stringent conditions are selected to be equal to the $T_m$ for a particular probe.

An example of stringent hybridization conditions for hybridization of complementary nucleic acids on a filter in a Southern or northern blot is 50% formalin with 1 mg of heparin at 42° C., with the hybridization being carried out overnight. An example of stringent wash conditions is a 0.2× SSC wash at 65° C. for 15 minutes (see, Sambrook et al., *Molecular Cloning: A Laboratory Manual,* 3rd Ed., Cold Spring Harbor Laboratory Press, Cold Spring Harbor, N.Y. (2001), which is incorporated by reference, for a description of SSC buffer). Often the high stringency wash is preceded by a low stringency wash to remove background probe signal. An example low stringency wash is 2×SSC at 40° C. for 15 minutes. In general, a signal to noise ratio of 5× (or higher) than that observed for an unrelated probe in the particular hybridization assay indicates detection of a specific hybridization.

Comparative hybridization can be used to identify nucleic acids of the invention.

In particular, detection of stringent hybridization in the context of the present invention indicates strong structural similarity to, e.g., the nucleic acids provided in the sequence listing herein. For example, it is desirable to identify test nucleic acids that hybridize to the exemplar nucleic acids herein under stringent conditions. One measure of stringent hybridization is the ability to detectably hybridize to one of the listed nucleic acids (e.g., nucleic acids with sequences selected from SEQ ID NOS: 3-27 and complements thereof) under stringent conditions. Stringent hybridization and wash conditions can easily be determined empirically for any test nucleic acid.

For example, in determining highly stringent hybridization and wash conditions, the stringency of the hybridization and wash conditions are gradually increased (e.g., by increasing temperature, decreasing salt concentration, increasing detergent concentration and/or increasing the concentration of organic solvents such as formalin in the hybridization or wash), until a selected set of criteria is met. For example, the stringency of the hybridization and wash conditions are gradually increased until a probe consisting of or comprising one or more nucleic acid sequences selected from SEQ ID NOS: 3-27 and 37-60 and complementary polynucleotide sequences thereof, binds to a perfectly matched complementary target (again, a nucleic acid comprising one or more nucleic acid sequences selected from SEQ ID NOS: 3-27 and 37-60 and complementary polynucleotide sequences thereof), with a signal to noise ratio that is at least 5× as high as that observed for hybridization of the probe to a non-target nucleic acid. In this case, non-target nucleic acids are those from organisms other than *N. gonorrhoeae* and in certain embodiments, *C. trachomatis*. Examples of such non-target nucleic acids include, e.g., those with GenBank® accession numbers, such as AE01469 (*Brucella suis* 1330 chromosome I section 155) and AE002435 (*Neisseria meningitidis* serogroup B strain MC58 section 77). Additional such sequences can be identified in, e.g., GenBank® by one of skill in the art.

A test nucleic acid is said to specifically hybridize to a probe nucleic acid when it hybridizes at least one-half as well to the probe as to the perfectly matched complementary target, i.e., with a signal to noise ratio at least one-half as high as hybridization of the probe to the target under conditions in which the perfectly matched probe binds to the perfectly matched complementary target with a signal to noise ratio that is at least about 5×-10× as high as that observed for hybridization to the non-target nucleic acids AE01469 (*Brucella suis* 1330 chromosome I section 155) or AE002435 (*Neisseria meningitidis* serogroup B strain MC58 section 77).

Ultra high-stringency hybridization and wash conditions are those in which the stringency of hybridization and wash conditions are increased until the signal to noise ratio for binding of the probe to the perfectly matched complementary target nucleic acid is at least 10× as high as that observed for hybridization to the non-target nucleic acids AE01469 (*Brucella suis* 1330 chromosome I section 155) or AE002435 (*Neisseria meningitidis* serogroup B strain MC58 section 77). A target nucleic acid which hybridizes to a probe under such conditions, with a signal to noise ratio of at least one-half that of the perfectly matched complementary target nucleic acid is said to bind to the probe under ultra-high stringency conditions.

Similarly, even higher levels of stringency can be determined by gradually increasing the stringency of hybridization and/or wash conditions of the relevant hybridization assay. For example, those in which the stringency of hybridization and wash conditions are increased until the signal to noise ratio for binding of the probe to the perfectly matched complementary target nucleic acid is at least 10×, 20×, 50×, 100×, or 500× or more as high as that observed for hybridization to the non-target nucleic acids AE01469 (*Brucella suis* 1330 chromosome I section 155) or AE002435 (*Neisseria meningitidis* serogroup B strain MC58 section 77) can be identified. A target nucleic acid which hybridizes to a probe under such conditions, with a signal to noise ratio of at least one-half that of the perfectly matched complementary target nucleic acid is said to bind to the probe under ultra-ultra-high stringency conditions.

The detection of target nucleic acids which hybridize to the nucleic acids represented by SEQ ID NOS: 3-27 and 37-60 under high, ultra-high and ultra-ultra high stringency conditions are a feature of the invention. Examples of such nucleic acids include those with one or a few silent or conservative nucleic acid substitutions as compared to a given nucleic acid sequence.

The terms "identical" or percent "identity" in the context of two or more nucleic acid or polypeptide sequences, refer to two or more sequences or subsequences that are the same or have a specified percentage of amino acid residues or nucleotides that are the same, when compared and aligned for maximum correspondence, e.g., as measured using one of the sequence comparison algorithms available to persons of skill or by visual inspection. Exemplary algorithms that are suitable for determining percent sequence identity and sequence similarity are the BLAST programs, which are described in, e.g., Altschul et al. (1990) "Basic local alignment search tool" *J. Mol. Biol.* 215:403-410, Gish et al. (1993) "Identification of protein coding regions by database similarity search" *Nature Genet.* 3:266-272, Madden et al. (1996) "Applications of network BLAST server" *Meth. Enzymol.* 266:131-141, Altschul et al. (1997) "Gapped BLAST and PSI-BLAST: a new generation of protein database search programs" *Nucleic Acids Res.* 25:3389-3402, and Zhang et al. (1997) "Power-BLAST: A new network BLAST application for interactive or automated sequence analysis and annotation" *Genome Res.*

7:649-656, which are each incorporated by reference. Many other optimal alignment algorithms are also known in the art and are optionally utilized to determine percent sequence identity.

The phrase "in solution" refers to an assay or reaction condition in which the components of the assay or reaction are not attached to a solid support and are present in a liquid medium. Exemplary liquid mediums include aqueous and organic fluids. For example, certain assays of the invention include incubating oligonucleotide probes together with *N. gonorrhoeae* nucleic acids and *N. gonorrhoeae* nucleic acid amplicons in solution to allow hybridization to occur.

The term "insertion" in the context of a nucleic acid sequence refers to an alteration in which at least one nucleotide is added to the nucleic acid sequence, e.g., at a 5'-terminus, at a 3'-terminus, and/or at an internal position of the nucleic acid sequence.

A "label" refers to a moiety attached (covalently or non-covalently), or capable of being attached, to a molecule, which moiety provides or is capable of providing information about the molecule (e.g., descriptive, identifying, etc. information about the molecule) or another molecule with which the labeled molecule interacts (e.g., hybridizes, etc.). Exemplary labels include fluorescent labels (including, e.g., quenchers or absorbers), weakly fluorescent labels, non-fluorescent labels, colorimetric labels, chemiluminescent labels, bioluminescent labels, radioactive labels, mass-modifying groups, antibodies, antigens, biotin, haptens, enzymes (including, e.g., peroxidase, phosphatase, etc.), and the like.

A "linker" refers to a chemical moiety that covalently or non-covalently attaches a compound or substituent group to another moiety, e.g., a nucleic acid, an oligonucleotide probe, a primer nucleic acid, an amplicon, a solid support, or the like. For example, linkers are optionally used to attach oligonucleotide probes to a solid support (e.g., in a linear or other logic probe array). To further illustrate, a linker optionally attaches a label (e.g., a fluorescent dye, a radioisotope, etc.) to an oligonucleotide probe, a primer nucleic acid, or the like. Linkers are typically at least bifunctional chemical moieties and in certain embodiments, they comprise cleavable attachments, which can be cleaved by, e.g., heat, an enzyme, a chemical agent, electromagnetic radiation, etc. to release materials or compounds from, e.g., a solid support. A careful choice of linker allows cleavage to be performed under appropriate conditions compatible with the stability of the compound and assay method. Generally a linker has no specific biological activity other than to, e.g., join chemical species together or to preserve some minimum distance or other spatial relationship between such species. However, the constituents of a linker may be selected to influence some property of the linked chemical species such as three-dimensional conformation, net charge, hydrophobicity, etc. Exemplary linkers include, e.g., oligopeptides, oligonucleotides, oligopolyamides, oligoethyleneglycerols, oligoacrylamides, alkyl chains, or the like. Additional description of linker molecules is provided in, e.g., Hermanson, *Bioconjugate Techniques*, Elsevier Science (1996), Lyttle et al. (1996) *Nucleic Acids Res.* 24(14):2793, Shchepino et al. (2001) *Nucleosides, Nucleotides, & Nucleic Acids* 20:369, Doronina et al (2001) *Nucleosides, Nucleotides, & Nucleic Acids* 20:1007, Trawick et al. (2001) *Bioconjugate Chem.* 12:900, Olejnik et al. (1998) *Methods in Enzymology* 291:135, and Pljevaljcic et al. (2003) *J. Am. Chem. Soc.* 125(12):3486, all of which are incorporated by reference.

A "mass modifying" group modifies the mass, typically measured in terms of molecular weight as daltons, of a molecule that comprises the group. For example, mass modifying groups that increase the discrimination between at least two nucleic acids with single base differences in size or sequence can be used to facilitate sequencing using, e.g., molecular weight determinations.

A "mixture" refers to a combination of two or more different components. A "reaction mixture" refers a mixture that comprises molecules that can participate in and/or facilitate a given reaction. An "amplification reaction mixture" refers to a solution containing reagents necessary to carry out an amplification reaction, and typically contains primers, a thermostable DNA polymerase, dNTP's, and a divalent metal cation in a suitable buffer. A reaction mixture is referred to as complete if it contains all reagents necessary to carry out the reaction, and incomplete if it contains only a subset of the necessary reagents. It will be understood by one of skill in the art that reaction components are routinely stored as separate solutions, each containing a subset of the total components, for reasons of convenience, storage stability, or to allow for application-dependent adjustment of the component concentrations, and, that reaction components are combined prior to the reaction to create a complete reaction mixture. Furthermore, it will be understood by one of skill in the art that reaction components are packaged separately for commercialization and that useful commercial kits may contain any subset of the reaction components, which includes the modified primers of the invention.

A "modified primer nucleic acid" refers to a primer nucleic acid that comprises a moiety or sequence of nucleotides that provides a desired property to the primer nucleic acid. In certain embodiments, for example, modified primer nucleic acids comprise "nucleic acid amplification specificity altering modifications" that, e.g., reduce non-specific nucleic acid amplification (e.g., minimize primer dimer formation or the like), increase the yield of an intended target amplicon, and/or the like. Examples of nucleic acid amplification specificity altering modifications are described in, e.g., U.S. Pat. No. 6,001,611, entitled "MODIFIED NUCLEIC ACID AMPLIFICATION PRIMERS," issued Dec. 14, 1999 to Will, which is incorporated by reference. Other exemplary primer nucleic acid modifications include a "restriction site linker modification" in which a nucleotide sequence comprising a selected restriction site is attached, e.g., at 5'-terminus of a primer nucleic acid. Restriction site linkers are typically attached to primer nucleic acids to facilitate subsequent amplicon cloning or the like.

A "moiety" or "group" refers to one of the portions into which something, such as a molecule, is divided (e.g., a functional group, substituent group, or the like). For example, an oligonucleotide probe optionally comprises a quencher moiety, a labeling moiety, or the like.

The term "*Neisseria gonorrhoeae*," "*N. gonorrhoeae*," or "NG" refers to the bacterial species *gonorrhoeae* of the *Neisseria* genus. See, e.g., Schoolnik (Ed.) *Pathogenic Neisseriae: Proceedings of the Fourth International Symposium*, Asilomar, Calif., 21-25 Oct. 1984, Amer. Society for Microbiology (1986), which is incorporated by reference. Additional general description of *N. gonorrhoeae* and *C. trachomatis* is provided in, e.g., Struthers and Westran, *Clinical Bacteriology*, ASM Press and Manson Publishing (2003), Persing et al., *Molecular Microbiology: Diagnostic Principles and Practice*, ASM Press (2003), Murray, *Manual of Clinical Microbiology*, 8th Ed., ASM Press (2003), which are each incorporated by reference. See also, the *Neisseria gonorrhoeae* database provided on the world wide web at stdgen.lanl.gov as of Mar. 12, 2004.

The term "*Neisseria gonorrhoeae* nucleic acid" or "*N. gonorrhoeae* nucleic acid" refers to a nucleic acid (and/or an amplicon thereof) that is derived or isolated from *Neisseria gonorrhoeae*.

The term "nucleic acid" refers to nucleotides (e.g., ribonucleotides, deoxyribonucleotides, dideoxynucleotides, etc.) and polymers that comprise such nucleotides covalently linked together, either in a linear or branched fashion. Exemplary nucleic acids include deoxyribonucleoic acids (DNAs), ribonucleic acids (RNAs), DNA-RNA hybrids, oligonucleotides, polynucleotides, genes, cDNAs, aptamers, antisense nucleic acids, interfering RNAs (RNAis), molecular beacons, nucleic acid probes, peptide nucleic acids (PNAs), locked nucleic acids (LNA™s), PNA-DNA conjugates, PNA-RNA conjugates, LNA™-DNA conjugates, LNA™-RNA conjugates, etc.

A nucleic acid is typically single-stranded or double-stranded and will generally contain phosphodiester bonds, although in some cases, as outlined, herein, nucleic acid analogs are included that may have alternate backbones, including, for example and without limitation, phosphoramide (Beaucage et al. (1993) *Tetrahedron* 49(10):1925 and references therein; Letsinger (1970) *J. Org. Chem.* 35:3800; Sprinzl et al. (1977) *Eur. J. Biochem.* 81:579; Letsinger et al. (1986) *Nucl. Acids Res.* 14: 3487; Sawai et al. (1984) *Chem. Lett.* 805; Letsinger et al. (1988) *J. Am. Chem. Soc.* 110:4470; and Pauwels et al. (1986) *Chemica Scripta* 26: 1419, which are each incorporated by reference), phosphorothioate (Mag et al. (1991) *Nucleic Acids Res.* 19:1437; and U.S. Pat. No. 5,644,048, which are both incorporated by reference), phosphorodithioate (Briu et al. (1989) *J. Am. Chem. Soc.* 111: 2321, which is incorporated by reference), O-methylphosphoroamidite linkages (see Eckstein, *Oligonucleotides and Analogues: A Practical Approach*, Oxford University Press (1992), which is incorporated by reference), and peptide nucleic acid backbones and linkages (see, Egholm (1992) *J. Am. Chem. Soc.* 114:1895; Meier et al. (1992) *Chem. Int. Ed. Engl.* 31:1008; Nielsen (1993) *Nature* 365:566; and Carlsson et al. (1996) *Nature* 380:207, which are each incorporated by reference). Other analog nucleic acids include those with positively charged backbones (Denpcy et al. (1995) *Proc. Natl. Acad. Sci. USA* 92:6097, which is incorporated by reference); non-ionic backbones (U.S. Pat. Nos. 5,386,023, 5,637,684, 5,602,240, 5,216,141 and 4,469,863; Angew (1991) *Chem. Intl. Ed. English* 30: 423; Letsinger et al. (1988) *J. Am. Chem. Soc.* 110:4470; Letsinger et al. (1994) *Nucleoside & Nucleotide* 13:1597; Chapters 2 and 3, ASC Symposium Series 580, "Carbohydrate Modifications in Antisense Research", Ed. Y. S. Sanghvi and P. Dan Cook; Mesmaeker et al. (1994) *Bioorganic & Medicinal Chem: Lett.* 4: 395; Jeffs et al. (1994) *J. Biomolecular NMR* 34:17; and *Tetrahedron Lett.* 37:743 (1996), which are each incorporated by reference) and non-ribose backbones, including those described in U.S. Pat. Nos. 5,235,033 and 5,034,506, and Chapters 6 and 7, ASC Symposium Series 580, Carbohydrate Modifications in Antisense Research, Ed. Y. S. Sanghvi and P. Dan Cook, which references are each incorporated by reference. Nucleic acids containing one or more carbocyclic sugars are also included within the definition of nucleic acids (see Jenkins et al. (1995) *Chem. Soc. Rev.* pp 169-176, which is incorporated by reference). Several nucleic acid analogs are also described in, e.g., Rawls, C & E News Jun. 2, 1997 page 35, which is incorporated by reference. These modifications of the ribose-phosphate backbone may be done to facilitate the addition of additional moieties such as labels, or to alter the stability and half-life of such molecules in physiological environments.

In addition to these naturally occurring heterocyclic bases that are typically found in nucleic acids (e.g., adenine, guanine, thymine, cytosine, and uracil), nucleic acid analogs also include those having non-naturally occurring heterocyclic or modified bases, many of which are described, or otherwise referred to, herein. In particular, many non-naturally occurring bases are described further in, e.g., Seela et al. (1991) *Helv. Chim. Acta* 74:1790, Grein et al. (1994) *Bioorg. Med. Chem. Lett.* 4:971-976, and Seela et al. (1999) *Helv. Chim. Acta* 82:1640, which are each incorporated by reference. To further illustrate, certain bases used in nucleotides that act as melting temperature (TO modifiers are optionally included. For example, some of these include 7-deazapurines (e.g., 7-deazaguanine, 7-deazaadenine, etc.), pyrazolo[3,4-d]pyrimidines, propynyl-dN (e.g., propynyl-dU, propynyl-dC, etc.), and the like. See, e.g., U.S. Pat. No. 5,990,303, entitled "SYNTHESIS OF 7-DEAZA-2'-DEOXYGUANOSINE NUCLEOTIDES," which issued Nov. 23, 1999 to Seela, which is incorporated by reference. Other representative heterocyclic bases include, e.g., hypoxanthine, inosine, xanthine; 8-aza derivatives of 2-aminopurine, 2,6-diaminopurine, 2-amino-6-chloropurine, hypoxanthine, inosine and xanthine; 7-deaza-8-aza derivatives of adenine, guanine, 2-aminopurine, 2,6-diaminopurine, 2-amino-6-chloropurine, hypoxanthine, inosine and xanthine; 6-azacytosine; 5-fluorocytosine; 5-chlorocytosine; 5-iodocytosine; 5-bromocytosine; 5-methylcytosine; 5-propynylcytosine; 5-bromovinyluracil; 5-fluorouracil; 5-chlorouracil; 5-iodouracil; 5-bromouracil; 5-trifluoromethyluracil; 5-methoxymethyluracil; 5-ethynyluracil; 5-propynyluracil, and the like.

Examples of modified bases and nucleotides are also described in, e.g., U.S. Pat. No. 5,484,908, entitled "OLIGO-NUCLEOTIDES CONTAINING 5-PROPYNYL PYRIMIDINES," issued Jan. 16, 1996 to Froehler et al., U.S. Pat. No. 5,645,985, entitled "ENHANCED TRIPLE-HELIX AND DOUBLE-HELIX FORMATION WITH OLIGOMERS CONTAINING MODIFIED PYRIMIDINES," issued Jul. 8, 1997 to Froehler et al., U.S. Pat. No. 5,830,653, entitled "METHODS OF USING OLIGOMERS CONTAINING MODIFIED PYRIMIDINES," issued Nov. 3, 1998 to Froehler et al., U.S. Pat. No. 6,639,059, entitled "SYNTHESIS OF [2.2.1]BICYCLO NUCLEOSIDES," issued Oct. 28, 2003 to Kochkine et al., U.S. Pat. No. 6,303,315, entitled "ONE STEP SAMPLE PREPARATION AND DETECTION OF NUCLEIC ACIDS IN COMPLEX BIOLOGICAL SAMPLES," issued Oct. 16, 2001 to Skouv, and U.S. Pat. Application Pub. No. 2003/0092905, entitled "SYNTHESIS OF [2.2.1]BICYCLO NUCLEOSIDES," by Kochkine et al. that published May 15, 2003, which are each incorporated by reference.

The term "nucleic acid detection reagent" refers to a reagent that detectably binds (e.g., hydrogen bonds in nucleic acid hybridization, in antibody-antigen recognition, or the like, or other types of binding interactions) to a nucleic acid that comprises SEQ ID NO: 1, SEQ ID NO: 2, SEQ ID NO: 36, a substantially identical variant thereof in which the variant has at least 90% sequence identity to one of SEQ ID NOS: 1 or 2 or 36, or a complement of SEQ ID NO: 1, SEQ ID NO: 2, SEQ ID NO: 36, or the variant. For example, nucleic acids (e.g., probe nucleic acids, primer nucleic acids, etc.) that comprise sequences selected from SEQ ID NOS: 3-27 and 37-60 or complements thereof specifically bind to nucleic acids having these sequences. Other exemplary nucleic acid detection reagents include sequence specific antibodies that specifically bind to nucleic acids comprising SEQ ID NO: 1, SEQ ID NO: 2, SEQ ID NO: 36, a substantially identical variant thereof in which the variant has at least 90% sequence identity to one of SEQ ID NOS: 1 or 2 or 36, or a complement of SEQ ID NO: 1, SEQ ID NO: 2, SEQ ID NO: 36, or the variant.

A "nucleotide" refers to an ester of a nucleoside, e.g., a phosphate ester of a nucleoside. For example, a nucleotide can include 1, 2, 3, or more phosphate groups covalently linked to a 5' position of a sugar moiety of the nucleoside.

A "nucleotide incorporating biocatalyst" refers to a catalyst that catalyzes the incorporation of nucleotides into a nucleic acid. Nucleotide incorporating biocatalysts are typically enzymes. An "enzyme" is a protein-and/or nucleic acid-based catalyst that acts to reduce the activation energy of a chemical reaction involving other compounds or "substrates." A "nucleotide incorporating enzyme" refers to an enzyme that catalyzes the incorporation of nucleotides into a nucleic acid, e.g., during nucleic acid amplification or the like. Exemplary nucleotide incorporating enzymes include, e.g., polymerases, terminal transferases, reverse transcriptases, telomerases, polynucleotide phosphorylases, and the like.

An "oligonucleotide" refers to a nucleic acid that includes at least two nucleic acid monomer units (e.g., nucleotides), typically more than three monomer units, and more typically greater than ten monomer units. The exact size of an oligonucleotide generally depends on various factors, including the ultimate function or use of the oligonucleotide. Oligonucleotides are optionally prepared by any suitable method, including, but not limited to, isolation of an existing or natural sequence, DNA replication or amplification, reverse transcription, cloning and restriction digestion of appropriate sequences, or direct chemical synthesis by a method such as the phosphotriester method of Narang et al. (1979) *Meth. Enzymol.* 68:90-99; the phosphodiester method of Brown et al. (1979) *Meth. Enzymol.* 68:109-151; the diethylphosphoramidite method of Beaucage et al. (1981) *Tetrahedron Lett.* 22:1859-1862; the triester method of Matteucci et al. (1981) *J. Am. Chem. Soc.* 103:3185-3191; automated synthesis methods; or the solid support method of U.S. Pat. No. 4,458,066, or other methods known in the art. All of these references are incorporated by reference.

The term "oligonucleotide probe," "probe nucleic acid," or "probe" refers to a labeled or unlabeled oligonucleotide capable of selectively hybridizing to a target nucleic acid under suitable conditions. Typically, a probe is sufficiently complementary to a specific target sequence (e.g., an *N. gonorrhoeae* nucleic acid that comprises SEQ ID NO: 1, SEQ ID NO: 2, SEQ ID NO: 36, a substantially identical variant thereof in which the variant has at least, 90% sequence identity to one of SEQ ID NOS: 1 or 2 or 36, or a complement of SEQ ID NO: 1, SEQ ID NO: 2, SEQ ID NO: 36, or the variant), a *C. trachomatis* nucleic acid sequence, etc.) contained in a nucleic acid sample to form a stable hybridization duplex with the target sequence under a selected hybridization condition, such as, but not limited to, a stringent hybridization condition. A hybridization assay carried out using the probe under sufficiently stringent hybridization conditions permits the selective detection of a specific target sequence. The term "hybridizing region" refers to that region of a nucleic acid that is exactly or substantially complementary to, and therefore hybridizes to, the target sequence. For use in a hybridization assay for the discrimination of single nucleotide differences in sequence, the hybridizing region is typically from about 8 to about 100 nucleotides in length. Although the hybridizing region generally refers to the entire oligonucleotide, the probe may include additional nucleotide sequences that function, for example, as linker binding sites to provide a site for attaching the probe sequence to a solid support or the like. In certain embodiments, an oligonucleotide probe of the invention comprises one or more labels (e.g., a reporter dye, a quencher moiety, etc.), such as a FRET probe, a molecular beacon, or the like, which can also be utilized to detect hybridization between the probe and target nucleic acids in a sample. In some embodiments, the hybridizing region of the oligonucleotide probe is completely complementary to the target sequence. However, in general, complete complementarity is not necessary; stable duplexes may contain mismatched bases or unmatched bases. Modification of the stringent conditions may be necessary to permit a stable hybridization duplex with one or more base pair mismatches or unmatched bases. Sambrook et al., *Molecular Cloning: A Laboratory Manual,* 3rd Ed., Cold Spring Harbor Laboratory Press, Cold Spring Harbor, N.Y. (2001), which is incorporated by reference, provides guidance for suitable modification. Stability of the target/probe duplex depends on a number of variables including length of the oligonucleotide, base composition and sequence of the oligonucleotide, temperature, and ionic conditions. One of skill in the art will recognize that, in general, the exact complement of a given probe is similarly useful as a probe. Exemplary probes of the invention, which bind to an *N. gonorrhoeae* nucleic acid with a sequence consisting of SEQ ID NO: 1, SEQ ID NO: 2, SEQ ID NO: 36, a substantially identical variant thereof in which the variant has at least 90% sequence identity to one of SEQ ID NOS: 1 or 2 or 36, or a complement of SEQ ID NO: 1, SEQ ID NO: 2, SEQ ID NO: 36, or the variant, comprise sequences selected from SEQ ID NOS: 3-27 and 37-60 and complements thereof. One of skill in the art will also recognize that, in certain embodiments, probe nucleic acids can also be used as primer nucleic acids.

A "primer nucleic acid" or "primer" is a nucleic acid that can hybridize to a template nucleic acid (e.g., an *N. gonorrhoeae* nucleic acid that comprises SEQ ID NO: 1, SEQ ID NO: 2, SEQ ID NO: 36, a substantially identical variant thereof in which the variant has at least 90% sequence identity to one of SEQ ID NOS: 1 or 2 or 36, or a complement of SEQ ID NO: 1, SEQ ID NO: 2, SEQ ID NO: 36, or the variant, a *C. trachomatis* nucleic acid, etc.) and permit chain extension or elongation using, e.g., a nucleotide incorporating biocatalyst, such as a polymerase under appropriate reaction conditions. A primer nucleic acid is typically a natural or synthetic oligonucleotide (e.g., a single-stranded oligodeoxyribonucleotide, etc.). Although other primer nucleic acid lengths are optionally utilized, they typically comprise hybridizing regions that range from about 8 to about 100 nucleotides in length. Short primer nucleic acids generally utilize cooler temperatures to form sufficiently stable hybrid complexes with template *N. gonorrhoeae* or *C. trachomatis* nucleic acid. A primer nucleic acid that is at least partially complementary to a subsequence of a template *N. gonorrhoeae* or *C. trachomatis* nucleic acid is typically sufficient to hybridize with the template for extension to occur. A primer nucleic acid can be labeled, if desired, by incorporating a label detectable by, e.g., spectroscopic, photochemical, biochemical, immunochemical, chemical, or other techniques. To illustrate, useful labels include radioisotopes, fluorescent dyes, electron-dense reagents, enzymes (as commonly used in ELISAs), biotin, or haptens and proteins for which antisera or monoclonal antibodies are available. Many of these and other labels are described further herein and/or are otherwise known in the art. Exemplary primer nucleic acids of the invention, which bind to an *N. gonorrhoeae* nucleic acid with a sequence consisting of SEQ ID NO: 1, SEQ ID NO: 2, SEQ ID NO: 36, a substantially identical variant thereof in which the variant has at least 90% sequence identity to one of SEQ ID NOS: 1 or 2 or 36, or a complement of SEQ ID NO: 1, SEQ ID NO: 2, SEQ ID NO: 36, or the variant, comprise sequences selected from SEQ ID NOS: 3-27 and 37-60 and complements thereof. One of skill in the art will recognize that, in certain embodiments, primer nucleic acids can also be used as probe nucleic acids.

A "quencher moiety" or "quencher" refers to a moiety that reduces and/or is capable of reducing the detectable emission of radiation, e.g., fluorescent or luminescent radiation, from a source that would otherwise have emitted this radiation. A quencher typically reduces the detectable radiation emitted by the source by at least 50%, typically by at least 80%, and more typically by at least 90%. Exemplary quenchers are provided in, e.g., U.S. Pat. No. 6,465,175, entitled "OLIGONUCLEOTIDE PROBES BEARING QUENCHABLE FLUORESCENT LABELS, AND METHODS OF USE THEREOF," which issued Oct. 15, 2002 to Horn et al., which is incorporated by reference.

The term "sample" refers to any substance containing or presumed to contain N. gonorrhoeae and/or C. trachomatis nucleic acid including, but not limited to, tissue or fluid isolated from one or more subjects or individuals, in vitro cell culture constituents, as well as clinical samples. Exemplary samples include blood, plasma, serum, urine, synovial fluid, seminal fluid, seminal plasma, prostatic fluid, vaginal fluid, cervical fluid, uterine fluid, cervical scrapings, amniotic fluid, anal scrapings, mucus, sputum, tissue, and the like.

The phrase "sample derived from a subject" refers to a sample obtained from the subject, whether or not that sample undergoes one or more processing steps (e.g., cell lysis, debris removal, stabilization, etc.) prior to analysis. To illustrate, samples can be derived from subjects by scraping, venipuncture, swabbing, biopsy, or other techniques known in the art.

The term "selectively bind" or "selective binding" in the context of nucleic acid detection reagents refers to a nucleic acid detection reagent that binds to an N. gonorrhoeae nucleic acid with a sequence consisting of SEQ ID NO: 1, SEQ ID NO: 2, SEQ ID NO: 36, a substantially identical variant thereof in which the variant has at least 90% sequence identity to one of SEQ ID NOS: 1 or 2 or 36, or a complement of SEQ ID NO: 1, SEQ ID NO: 2, SEQ ID NO: 36, or the variant to a greater extent than the nucleic acid detection reagent binds, under the same hybridization conditions, to nucleic acids from at least three organisms selected from each of Tables X and XI.

The term "selectively detect" refers to the ability to detect an N. gonorrhoeae nucleic acid with a sequence consisting of SEQ ID NO: 1, SEQ ID NO: 2, SEQ ID NO: 36, a substantially identical variant thereof in which the variant has at least 90% sequence identity to one of SEQ ID NOS: 1 or 2 or 36, or a complement of SEQ ID NO: 1, SEQ ID NO: 2, SEQ ID NO: 36, or the variant to a greater extent than nucleic acids from other organisms.

"Selectively hybridizing" or "selective hybridization" occurs when a nucleic acid sequence hybridizes to a specified nucleic acid target sequence to a detectably greater degree than its hybridization to non-target nucleic acid sequences. Selectively hybridizing sequences have at least 50%, or 60%, or 70%, or 80%, or 90% sequence identity or more, e.g., typically 95-100% sequence identity (i.e., complementarity) with each other.

A "sequence" of a nucleic acid refers to the order and identity of nucleotides in the nucleic acid. A sequence is typically read in the 5' to 3' direction.

A "sequence specific antibody" refers to an antibody that detectably binds to nucleic acids with sequences that consist of SEQ ID NO: 1, SEQ ID NO: 2, SEQ ID NO: 36, a substantially identical variant thereof in which the variant has at least 90% sequence identity to one of SEQ ID NOS: 1 or 2 or 36, or a complement of SEQ ID NO: 1, SEQ ID NO: 2, SEQ ID NO: 36, or the variant.

A "sequencing reaction" refers to a reaction that includes, e.g., the use of terminator nucleotides and which is designed to elucidate the sequence of nucleotides in a given nucleic acid.

A "set" refers to a collection of at least two things. For example, a set may include 2, 3, 4, 5, 10, 20, 50, 100, 1,000 or other number of molecule or sequence types. For example, certain aspects of the invention include reaction mixtures having sets of amplicons. A "subset" refers to any portion of a set.

A "solid support" refers to a solid material that can be derivatized with, or otherwise attached to, a chemical moiety, such as an oligonucleotide probe or the like. Exemplary solid supports include plates, beads, microbeads, tubes, fibers, whiskers, combs, hybridization chips (including microarray substrates, such as those used in GeneChip® probe arrays (Affymetrix, Inc., Santa Clara, Calif., USA) and the like), membranes, single crystals, ceramic layers, self-assembling monolayers, and the like.

An oligonucleotide probe is "specific" for a target sequence if the number of mismatches present between the oligonucleotide and the target sequence is less than the number of mismatches present between the oligonucleotide and non-target sequences that might be present in a sample. Hybridization conditions can be chosen under which stable duplexes are formed only if the number of mismatches present is no more than the number of mismatches present between the oligonucleotide and the target sequence. Under such conditions, the target-specific oligonucleotide can form a stable duplex only with a target sequence. Thus, the use of target-specific primers under suitably stringent amplification conditions enables the specific amplification of those sequences, which contain the target primer binding sites. Similarly, the use of target-specific probes under suitably stringent hybridization conditions enables the detection of a specific target sequence.

A "subject" refers to an organism. Typically, the organism is a mammalian organism, particularly a human organism. In certain embodiments, for example, a subject is a patient suspected of having an NG and/or a CT infection.

A "subsequence" or "segment" refers to any portion of an entire nucleic acid sequence.

A "substantially identical variant" in the context of nucleic acids or polypeptides, refers to two or more sequences that have at least 85%, typically at least 90%, more typically at least 95% nucleotide or sequence identity to one another when compared and aligned for maximum correspondence, as measured using, e.g., a sequence comparison algorithm or by visual inspection. The substantial identity generally exists over a region of the sequences that is at least about 15 nucleotides or amino acids in length, more typically over a region that is at least about 20 nucleotides or amino acids in length, and even more typically the sequences are substantially identical over a region of at least about 25 nucleotides or amino acids in length. In some embodiments, for example, the sequences are substantially identical over the entire length of the nucleic acids or polypeptides being compared. SEQ ID NO: 36 can be considered as an exemplary variant of SEQ ID NO: 1.

The term "substitution" in the context of a nucleic acid sequence refers to an alteration in which at least one nucleotide of the nucleic acid sequence is replaced by a different nucleotide.

The terms "target sequence," "target region," and "target nucleic acid" refer to a region of a nucleic acid, which is to be amplified, detected, or otherwise analyzed.

A "terminator nucleotide" refers to a nucleotide, which upon incorporation into a nucleic acid prevents further extension of the nucleic acid, e.g., by at least one nucleotide incorporating biocatalyst.

A "thermostable enzyme" refers to an enzyme that is stable to heat, is heat resistant and retains sufficient catalytic activity when subjected to elevated temperatures for selected periods of time. For example, a thermostable polymerase retains sufficient activity to effect subsequent primer extension reactions when subjected to elevated temperatures for the time necessary to effect denaturation of double-stranded nucleic acids. Heating conditions necessary for nucleic acid denaturation are well known in the art and are exemplified in U.S. Pat. Nos. 4,683,202 and 4,683,195, which are both incorporated by reference. As used herein, a thermostable polymerase is typically suitable for use in a temperature cycling reaction such as the polymerase chain reaction ("PCR"). For a thermostable polymerase, enzymatic activity refers to the catalysis of the combination of the nucleotides in the proper manner to form primer extension products that are complementary to a template nucleic acid (e.g., selected subsequences of an *N. gonorrhoeae* or *C. trachomatis* genome).

II. Overview

The invention relates to the selective detection of *Neisseria gonorrhoeae*. In particular, based on new detection strategies utilizing at least one of two target regions of the *N. gonorrhoeae* genome, *N. gonorrhoeae* infections can be diagnosed using the methods and reagents described herein. Each of these target regions has multiple copies in the *N. gonorrhoeae* genome. Accordingly, this typically facilitates the detection of *N. gonorrhoeae* in samples utilizing the approaches described herein relative to techniques that target single copy regions of the genome. In addition, the nucleic acid detection reagents described herein generally detectably bind, under selected assay conditions, to nucleotide sequences that are present in *N. gonorrhoeae*, but which are not present in other species, thereby minimizing the occurrence of, e.g., false positives. This specificity is illustrated in, for example, FIGS. 5-7, 9, and 10, and the related description in the examples provided below. Many other features of the invention are also described herein.

To further illustrate, certain methods of the invention include contacting or incubating nucleic acid detection reagents with nucleic acids in or from samples derived from subjects (e.g., human patients suspected of having *N. gonorrhoeae* infections, etc.). In certain embodiments, target regions of the nucleic acids in the sample are amplified prior to or simultaneously with being contacted with the nucleic acid detection reagents. Nucleic acid detection reagents detectably bind to a nucleic acid with a sequence consisting SEQ ID NO: 1, SEQ ID NO: 2, SEQ ID NO: 36, a substantially identical variant thereof in which the variant has at least 90% sequence identity to one of SEQ ID NOS: 1 or 2 or 36, or a complement of SEQ ID NO: 1, SEQ ID NO: 2, SEQ ID NO: 36, or the variant. As described further below, SEQ ID NO: 1 and SEQ ID NO: 2 are consensus sequences that correspond to two regions of the *N. gonorrhoeae* genome that are targeted in the methods of the invention; SEQ ID NO: 36 is a variant of SEQ ID NO: 1. These methods also include monitoring (e.g., at a single time point, at multiple discrete time points, continuously over a selected time period, etc.) binding between the nucleic acids and/or amplicons, and the nucleic acid detection reagents to determine whether *Neisseria gonorrhoeae* is present in the samples, e.g., to diagnose patients from which the samples were derived, to monitor courses of treatment for patients diagnosed with *Neisseria gonorrhoeae* infections, and/or the like.

In some embodiments, these methods further include contacting the nucleic acids and/or amplicons of the target regions with additional nucleic acid detection reagents that detectably bind to *Chlamydia trachomatis* nucleic acids. In these embodiments, the methods also include monitoring binding between the nucleic acids and/or the amplicons, and the additional nucleic acid detection reagents to determine whether *Chlamydia trachomatis* is also present in the samples. Optionally, these methods are also repeated one or more times using additional samples (e.g., from the same subject) to monitor, e.g., courses of treatment for subjects diagnosed with *Neisseria gonorrhoeae* and/or *Chlamydia trachomatis* infections, the recurrence of infections, and/or the like.

Other methods of the invention include contacting or incubating nucleic acids from samples with at least a first pair of primer nucleic acids that include at least one nucleic acid selected from the group consisting of: SEQ ID NOS: 3-27, 37-60, and 68-70, or complements thereof, in nucleic acid amplification reactions. As described further below, SEQ ID NOS: 3-27, 37-60, and 68-70, are oligonucleotides that include subsequences of SEQ ID NO: 1 or SEQ ID NO: 2 or SEQ ID NO: 36. In addition, these methods also include detecting amplicons during or after the amplification reactions are performed to detect whether *Neisseria gonorrhoeae* is present in the samples. Optionally, these methods further include contacting the nucleic acids from the samples with at least a second pair of primer nucleic acids that are at least partially complementary to a *Chlamydia trachomatis* nucleic acid and detecting additional amplicons during or after the amplification reactions are performed to determine whether *Chlamydia trachomatis* is present in the samples. These methods are also optionally repeated at selected time points.

In addition to compositions and reaction mixtures, the invention also relates to kits and systems for detecting these pathogenic agents, and to related computers and computer readable media.

III. Nucleic Acid Detection Reagents

The nucleic acid detection reagents of the invention include various embodiments, including probe nucleic acids, primer nucleic acids, and sequence specific antibodies. Some of these nucleic acid detection reagents target repeat 130 (also referred to herein as "NGDR9"), which is an 806 base pair direct repeat in the *N. gonorrhoeae* genome that is thought to encode a protein. The *N. gonorrhoeae* genome includes two copies of NGDR9, one located at nucleotide positions 458182-458988 and the other located at nucleotide positions 1586504-1587310. A consensus sequence of NGDR9 corresponds to SEQ ID NO: 1, which is shown in Table I. Although only one strand of the NGDR9 locus is shown in Table I, those of skill in the art will appreciate that SEQ ID NO: 1 identifies a region of double stranded genomic nucleic acid, and that the sequences of both strands are fully specified by the sequence information provided.

TABLE I

SEQ ID NO: 1

```
CAGCCGCATC ATGATGCCGC ACGTCAGGGC TTCGTCTTCC    40
GATACCTTTG CGCCAGACAA CATCCGGGCG ATGTTTTCTT    80
TTTGCGCTTT TGACCGGGCG GACAGCCGGT TCCGGTCAAC   120
GTTTCTGACC GTCCCGGCGC GTTTGACGGC GCGTTCCTGC   160
CGCGTTGATT CCTTCGCCGC GCGTTTGGCG GCAAGCATCT   200
GTTTTGCCGT CGGTTTTGTT GCTACTGTTT GCATTTTGTT   240
TTCTCGATTT TTTGATGCCG TTCTCTCAAT GCCCAATCAT   280
AAAGCTGTAT CTCTCACGAG GTCGCCGAAT TTAAATTGAT   320
AGTTCATGTC TTGTTCCATT AATATCAAAC GCAATCTTCA   360
AACACCTCAA TTACATTTTT TAAATGCTA ATACCATAAT    400
TTATTACATC CTTTAGAAAT TCCAAAGAGG TATCCGCTTC   440
GTCTGCTTTA TCCCTAATTT CGTCTATATA ACCCTCTAAC   480
GATTCAGGCT CTTTTAATGC TTCTTTGCAT AAGTTATCTA   520
TTACCCTTAA TGCGTTTTTT ACATCTTCCA AATAGCTCAT   540
TTTTTGCTCC TTAACTCAAA ATGGGATGCT GTCGTCAACA   580
TCTTCTACGG TTTATCTAAT CTGCAAATTC TTCCGCCCTT   620
CAATCTTCGC GCCTGCTACT TGCCGACCGC TTTCAATCGC   680
TTTTCTGATG GCGGTTTTGT CCGGTTCGGT TTTGACGGCC   720
TCACGCATAA ATTCGGCGGG GATTTGTGCT TCGTCTAAGA   760
TCACGACGGC TTCGGATTTG CGGAACGAGG CTTTAAAAGT   800
GCCGTC                                         806
```

To illustrate, nucleic acid detection reagents comprising SEQ ID NOS: 3-12, 17-20, 24-26, or complements thereof, target NGDR9 or complements thereof SEQ ID NOS: 3-12, 17-20, and 24-26 are shown in Table II.

TABLE II

| | |
|---|---|
| SEQ ID NO: 3 | 5'-CGTTCTCTCAATGCCCAATCA-3' |
| SEQ ID NO: 4 | 5'-AGCAGACGAAGCGGATACCTC-3' |
| SEQ ID NO: 5 | 5'-CTCTCAATGCCCAATCATAAAGC-3' |
| SEQ ID NO: 6 | 5'-GTATCCGCTTCGTCTGCTTTATC-3' |
| SEQ ID NO: 7 | 5'-GTTTGGCGGCAAGCATCT-3' |
| SEQ ID NO: 8 | 5'-AAATGGGATGCTGTCGTCAA-3' |
| SEQ ID NO: 9 | 5'-GGCAAGCTTGTTTGGCGGCAAGCATCT-3' |
| SEQ ID NO: 10 | 5'-GGCGGATCCTTGACGACAGCATCCCATTT-3' |
| SEQ ID NO: 11 | 5'-AAACGCAATCTTCAAACACCTCA-3' |
| SEQ ID NO: 12 | 5'-TTTGACGGCCTCACGCATAA-3' |
| SEQ ID NO: 17 | 5'-CGAGGTCGCCGAATTTAAATTGATAGTT-3' |
| SEQ ID NO: 18 | 5'-AACTATCAATTTAAATTCGGCGACCTCG-3' |
| SEQ ID NO: 19 | 5'-CGAGGTCGCCGAATTTAAATTGATAGTTCA-3' |
| SEQ ID NO: 20 | 5'-TGAACTATCAATTTAAATTCGGCGACCTCG-3' |
| SEQ ID NO: 24 | 5'-GATAAAGCAGACGAAGCGGATAC-3' |
| SEQ ID NO: 25 | 5'-TTGACGACAGCATCCCATTT-3' |
| SEQ ID NO: 26 | 5'-TTATGCGTGAGGCCGTCAAA-3' |

Other nucleic acid detection reagents of the invention target repeat 116 (also referred to herein as "NGDR33"), which is an 1142 base pair direct repeat in the *N. gonorrhoeae* genome that is thought to encode a polypeptides. The *N. gonorrhoeae* genome includes two copies of NGDR33, one located at nucleotide positions 491768-492910 and the other located at nucleotide positions 1606987-1608129. A consensus sequence of NGDR33 corresponds to SEQ ID NO: 2, which is shown in Table III. Although only one strand of the NGDR33 locus is shown in Table III, those of skill in the art will appreciate that SEQ ID NO: 2 identifies a region of double stranded genomic nucleic acid, and that the sequences of both strands are fully specified by the sequence information specified.

TABLE III

| SEQ ID NO: 2 | | | | |
|---|---|---|---|---|
| ACGCCGTGGT | GCGGCCTGTT | TGTCGGATAC | TGCCTGGGCA | 40 |
| AAAGCGGACG | CGCGGTCATC | AGGGACTGGT | ATCGCGCCAA | 80 |
| AGCCTGGTCA | ATGTCGGGTT | TGACGAAACT | CGAAGCCCCC | 120 |
| GCATACGGCT | GCATCGCGGT | CAAACCGCGC | CGGGGCGGCG | 160 |
| GACACGTGTT | CTTCGTTGTC | GGCAAAGACG | CGGAAGGCAG | 200 |
| AATCTTGGGC | TTGGGCGGCA | ATCAGGGCAA | TATGGTATCC | 240 |
| ATCATCCCGT | TTGACCCTGC | GGACATTGAC | GGCTACTTCT | 280 |
| GGCCGTCCAA | GCTGATTGGC | GGCAAAGCCG | TGCCTTCGTC | 320 |
| CCCCGCCGAA | GGGCGTTACC | GGTTGTCGGA | CGTTGCCGCC | 360 |
| ACGGCGAAAC | AGGGCGCGGG | CGAGGCGTAA | ATGATTGGGG | 400 |
| CTTTGCTGAA | AAATTGGAAG | CCGCTGCTTA | TTTTGTCCGC | 440 |
| AATCGCGTTC | TTCGCCGTTT | CTTGGCAGCT | GGACAGGGCG | 480 |
| GCGCAATACC | GTCGCGGATA | CGGTGCGGCG | GTGTCGGAGG | 520 |
| TTTCGGAACG | CCTCAAAGCC | GCCGCGGTCG | AACACGCCGA | 560 |
| ACACGCCCGC | AAATCGTCCG | CCGCGTATCA | GGCGCAAAAG | 600 |
| GCGGCGCGCG | AGGAAAAAGA | AAGGGTGCGC | TATGTGCAAA | 640 |
| CGCTTAAAAT | CATTGAAAAA | CCTGTGTACC | GCAATGCCTG | 680 |
| TTTTGATGCT | GACGGCGTGC | GCGAACTCAA | CGCCGCCGTT | 720 |
| GACGACGGCG | GTTAAGCCGC | CCGCCGATTT | GGTGCGGCCC | 760 |
| TGCCCGAAAC | TGCCGCACCT | TGAAGGGAAC | ACGGGCGCGG | 800 |
| ACGTGCTGCC | GTGGGCCCTG | AAGGCGGCCG | GTATGTATAA | 840 |
| CGACTGCAGG | GCGCGGCACG | GCGCGCTGGT | ACGGGCGTTG | 880 |
| GGCGCGGATT | GAGTTGTCAA | CCGGAAGTTT | GCAACCGAAC | 920 |
| CGTCGGTTCC | GGGTTGGCGG | CCGCATCGGG | GGAAGTGTCG | 960 |
| GCATTCCCCC | CGATTTTTTA | CATATCGGGC | GGACGCGGCA | 1000 |
| AATTTTTGCC | GTTTTGTTTG | CGCGAAGGGG | GCGTTATACA | 1040 |
| AAATTATCAG | GCGCACCAAT | AATGGGCGGA | AATGAAAATG | 1080 |
| CCGTACCGAT | CCGGACAACA | ACCGATGCCG | CACCCTGCGG | 1120 |
| GCAGGCTTCG | CACTCTGAAA | GG | | 1142 |

For example, nucleic acid detection reagents corresponding to SEQ ID NOS: 13-16, 21-23, 27, or complements thereof, target NGDR33 or complements thereof. SEQ ID NOS: 13-16, 21-23, and 27 are shown in Table IV.

TABLE IV

| | |
|---|---|
| SEQ ID NO: 13 | 5'-TCAATGTCGGGTTTGACGAA-3' |
| SEQ ID NO: 14 | 5'-AACGTCCGACAACCGGTAAC-3' |
| SEQ ID NO: 15 | 5'-AATGTCGGGTTTGACGAAACTC-3' |
| SEQ ID NO: 16 | 5'-GTTACCGGTTGTCGGACGTT-3' |
| SEQ ID NO: 21 | 5'-GCGGCAATCAGGGCAATATGGTAT-3' |
| SEQ ID NO: 22 | 5'-ATACCATATTGCCCTGATTGCCGC-3' |
| SEQ ID NO: 23 | 5'-GGCGGCAATCAGGGCAATATGGTAT-3' |
| SEQ ID NO: 27 | 5'-AACGTCCGACAACCGGTAAC-3' |

In certain embodiments where NGDR9 is targeted, probes and/or primers optionally detectably bind to a nucleic acid segment that comprises one or more nucleotide positions of SEQ ID NO: 1 selected from the group consisting of: 259, 260, 262, 264, 265, 266, 268, 269, 273, 275, 276, 277, 279, 297, 298, 300, 301, 302, 303, 304, 305, 306, 308, 313, 314, 315, 316, 317, 318, 320, 321, 325, 326, 428, 429, 431, 432, 433, 434, 435, 440, 441, and 447. These nucleotide positions, which are highlighted and underlined in Table V, denote certain exemplary mismatches with the sequence of *Brucella suis* 1330 chromosome I section 155 (GenBank® accession number AE014469) that were identified in an alignment of the sequences of NGDR9 and *B. suis* 1330 chromosome I section 155. Other mismatches with this sequence from the *Brucella suis* genome are illustrated in FIG. 4. This sequence of the *B. suis* genome has a higher level of identity with NGDR9 than sequences from other bacterial species. An alignment of the sequence of NGDR9 with this *B. suis* sequence is described further in an example provided below.

TABLE V

SEQ ID NO: 1

| | | | | |
|---|---|---|---|---|
| CAGCCGCATC | ATGATGCCGC | ACGTCAGGGC | TTCGTCTTCC | 40 |
| GATACCTTTG | CGCCAGACAA | CATCCGGGCG | ATGTTTTCTT | 80 |
| TTTGCGCTTT | TGACCGGGCG | GACAGCCGGT | TCCGGTCAAC | 120 |
| GTTTCTGACC | GTCCCGGCGC | GTTTGACGGC | GCGTTCCTGC | 160 |
| CGCGTTGATT | CCTTCGCCGC | GCGTTTGGCG | GCAAGCATCT | 200 |
| GTTTTGCCGT | CGGTTTTGTT | GCTACTGTTT | GCATTTTGTT | 240 |
| TTCTCGATTT | TTTGATGCCG | TTCTCTCAAT | GCCCAATCAT | 280 |
| AAAGCTGTAT | CTCTCACGAG | GTCGCCGAAT | TTAAATTGAT | 320 |
| AGTTCATGTC | TTGTTCCATT | AATATCAAAC | GCAATCTTCA | 360 |
| AACACCTCAA | TTACATTTTT | TAAATCGCTA | ATACCATAAT | 400 |
| TTATTCATC | CTTTAGAAAT | TCCAAAGAGG | TATCCGCTTC | 440 |
| GTCTGCTTTA | TCCCTAATTT | CGTCTATATA | ACCCTCTAAC | 480 |
| GATTCAGGCT | CTTTTAATGC | TTCTTTGCAT | AAGTTATCTA | 520 |
| TTACCCTTAA | TGCGTTTTTT | ACATCTTCCA | AATAGCTCAT | 540 |
| TTTTTGCTCC | TTAACTCAAA | ATGGGATGCT | GTCGTCAACA | 580 |
| TCTTCTACGG | TTTATCTAAT | CTGCAAATTC | TTCCGCCCTT | 620 |
| CAATCTTCGC | GCCTGCTACT | TGCCGACCGC | TTTCAATCGC | 680 |
| TTTTCTGATG | GCGGTTTTGT | CCGGTTCGGT | TTTGACGGCC | 720 |
| TCACGCATAA | ATTCGGCGGG | GATTTGTGCT | TCGTCTAAGA | 760 |
| TCACGACGGC | TTCGGATTTG | CGGAACGAGG | CTTTAAAAGT | 800 |
| GCCGTC | | | | 806 |

Figure 8:
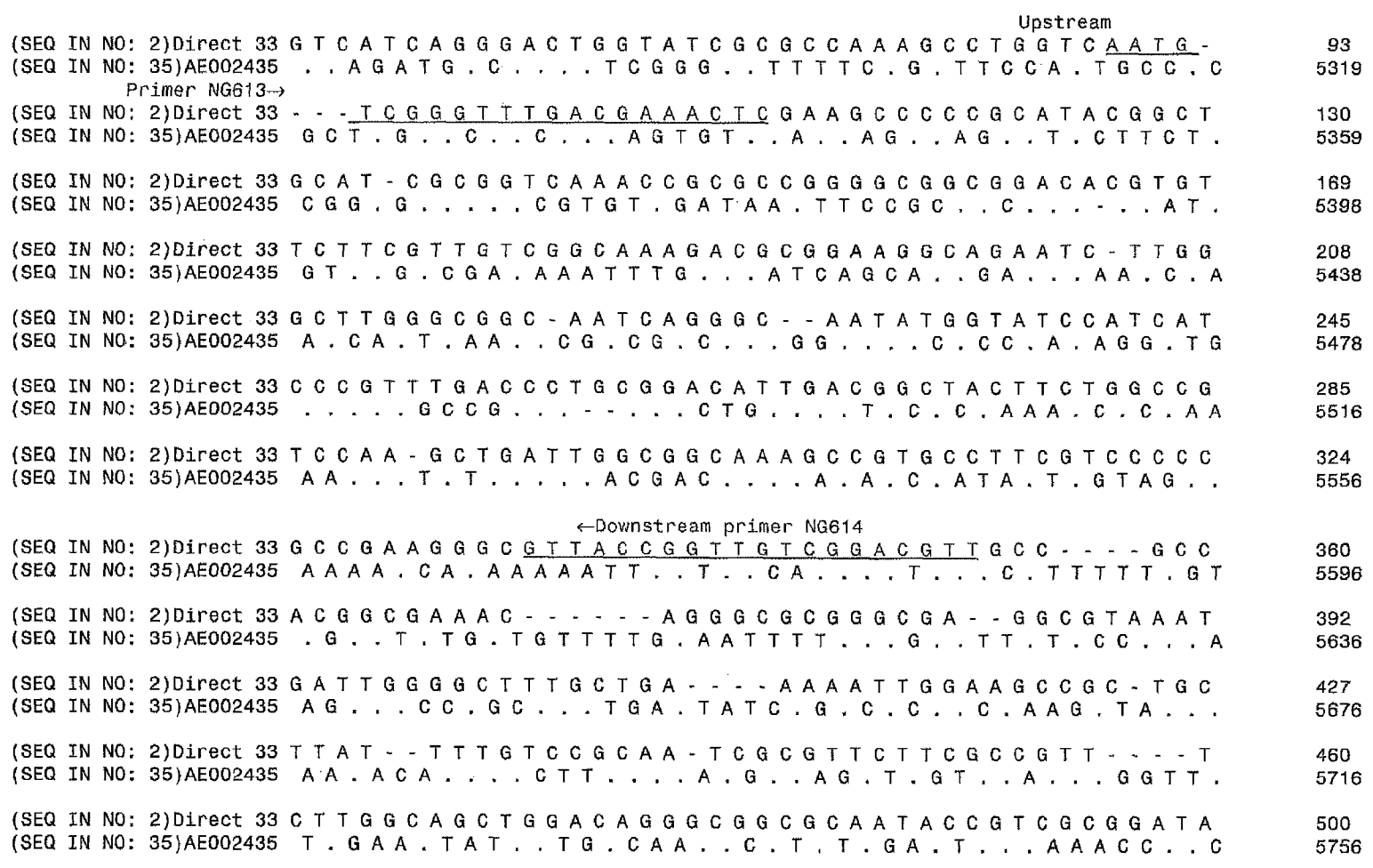
Figure 8:
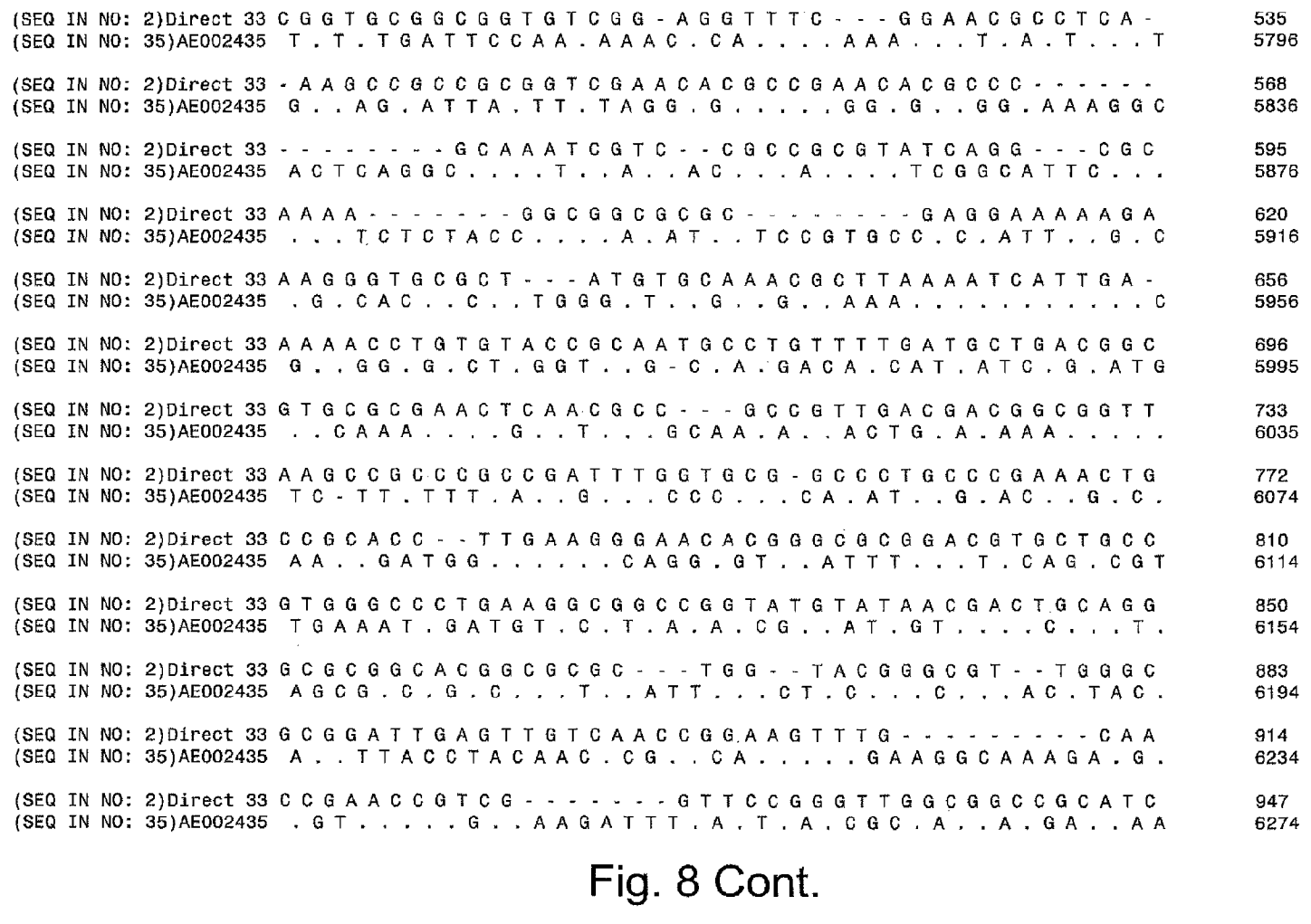

In some embodiments were NGDR33 is targeted, probes and/or primers optionally detectably bind to a nucleic acid segment that comprises one or more nucleotide positions of SEQ ID NO: 2 selected from the group consisting of: 89, 90, 91, 92, 95, 98, 101, 105, 106, 107, 216, 217, 220, 222, 223, 225, 233, 235, 236, 238, 335, 336, 337, 338, 339, 342, 345, 346, and 351. These nucleotide positions, which are highlighted and underlined in Table VI, denote some exemplary mismatches with the sequence of *Neisseria meningitidis* serogroup B strain MC58 section 77 (GenBank® accession number AE002435) that were identified in an alignment of the sequences of NGDR33 and *N. meningitidis* serogroup B strain MC58 section 77. Other mismatches with this sequence from the *N. meningitidis* genome are illustrated in FIG. 8. This sequence of the *N. meningitidis* genome has a higher level of identity with NGDR33 than sequences from other bacterial species. An alignment of the sequence of NGDR33 with this *N. meningitidis* sequence is described further in an example provided below.

TABLE VI

SEQ ID NO: 2

| | | | | |
|---|---|---|---|---|
| ACGCCGTGGT | GCGGCCTGTT | TGTCGGATAC | TGCCTGGGCA | 40 |
| AAAGCGACG | CGCGGTCATC | AGGGACTGGT | ATCGCGCCAA | 80 |
| AGCCTGGTCA | ATGTCGGGTT | TGACGAAACT | CGAAGCCCCC | 120 |
| GCATACGGCT | GCATCGCGGT | CAAACCGCGC | CGGGGCGGCG | 160 |
| GACACGTGTT | CTTCGTTGTC | GGCAAAGACG | CGGAAGGCAG | 200 |
| AATCTTGGGC | TTGGGCGGCA | ATCAGGGCAA | TATGGTATCC | 240 |
| ATCATCCCGT | TTGACCCTGC | GGACATTGAC | GGCTACTTCT | 280 |
| GGCCGTCCAA | GCTGATTGGC | GGCAAAGCCG | TGCCTTCGTC | 320 |
| CCCCGCCGAA | GGGCGTTACC | GGTTGTCGGA | CGTTGCCGCC | 360 |
| ACGGCGAAAC | AGGGCGCGGG | CGAGGCGTAA | ATGATTGGGG | 400 |
| CTTTGCTGAA | AAATTGGAAG | CCGCTGCTTA | TTTTGTCCGC | 440 |
| AATCGCGTTC | TTCGCCGTTT | CTTGGCAGCT | GGACAGGGCG | 480 |
| GCGCAATACC | GTCGCGGATA | CGGTGCGGCG | GTGTCGGAGG | 520 |
| TTTCGGAACG | CCTCAAAGCC | GCCGCGGTCG | AACACGCCGA | 560 |
| ACACGCCCGC | AAATCGTCCG | CCGCGTATCA | GGCGCAAAAG | 600 |
| GCGGCGCGCG | AGGAAAAAGA | AAGGGTGCGC | TATGTGCAAA | 640 |
| CGCTTAAAAT | CATTGAAAAA | CCTGTGTACC | GCAATGCCTG | 680 |

TABLE VI-continued

SEQ ID NO: 2

| | | | | |
|---|---|---|---|---|
| TTTTGATGCT | GACGGCGTGC | GCGAACTCAA | CGCCGCCGTT | 720 |
| GACGACGGCG | GTTAAGCCGC | CCGCCGATTT | GGTGCGGCCC | 760 |
| TGCCCGAAAC | TGCCGCACCT | TGAAGGGAAC | ACGGGCGCGG | 800 |
| ACGTGCTGCC | GTGGGCCCTG | AAGGCGGCCG | GTATGTATAA | 840 |
| CGACTGCAGG | GCGCGGCACG | GCGCGCTGGT | ACGGGCGTTG | 880 |
| GGCGCGGATT | GAGTTGTCAA | CCGGAAGTTT | GCAACCGAAC | 920 |
| CGTCGGTTCC | GGGTTGGCGG | CCGCATCGGG | GGAAGTGTCG | 960 |
| GCATTCCCCC | CGATTTTTTA | CATATCGGGC | GGACGCGGCA | 1000 |
| AATTTTTGCC | GTTTTGTTTG | CGCGAAGGGG | GCGTTATACA | 1040 |
| AAATTATCAG | GCGCACCAAT | AATGGGCGGA | AATGAAAATG | 1080 |
| CCGTACCGAT | CCGGACAACA | ACCGATGCCG | CACCCTGCGG | 1120 |
| GCAGGCTTCG | CACTCTGAAA | GG | | 1142 |

Other nucleic acid detection reagents of the invention target a variation sequence of repeat 130 (also referred to herein as "NGDR9Var"). A consensus sequence of NGDR9Var corresponds to SEQ ID NO: 36, which is shown in Table A. Although only one strand of the NGDR9Var locus is shown in Table A, those of skill in the art will appreciate that SEQ ID NO: 36 identifies a region of double stranded genomic nucleic acid, and that the sequences of both strands are fully specified by the sequence information specified.

TABLE A

SEQ ID NO: 36

| | | | | |
|---|---|---|---|---|
| CAGCCGCATC | ATGATGCCGC | ACGTCAGGGC | TTCGTCTTCC | 40 |
| GATACCTTTG | CGCCCGACAA | CATCCGGGCG | ATGTTTTCTT | 80 |
| TTTGCGCTTT | TGACCGGGCG | GACAGCCGGT | TCCGGTCAAC | 120 |
| GTTTCTGACC | GTCCCGGCGC | GTTTGACGGC | GCGTTCCTGC | 160 |
| CGCGTTGATT | CCTTCGCCGC | GCGTTTGGCG | GCAAGCATCT | 200 |
| GTTTTGCCGT | CGGTTTTGTT | GTTGCCGTTT | GCATTTTTAC | 240 |
| CTCCTTTTAA | AACTGTTTCG | ACAGGCTTGC | GAACGGCCTT | 280 |
| CCCGTTCACT | TCCCGCGCCT | GCCTGATTCC | TACGGTGCGG | 320 |
| ATGTCGGGAT | TGCCCGGCGG | CAGCCTGACA | AACCCTTCGG | 360 |
| CGGCCCCTAT | GGTTGGATAT | CCGGGGCTGA | TTCGGCAGCG | 400 |
| GCTGTTGCTT | GGCCGCTCCC | GTCCGCGCCG | GTCTGCGTAC | 440 |
| CGCTTGGAAT | CCTCTTTGTC | GCAAACAGGC | CGCCGCCGTT | 480 |
| TTTCTTCTTC | GGGACGATGT | TTTCCAAAGG | CTGCGAACAT | 520 |
| GGCGGCCCCT | GTTTATCTAA | TCTGCAAATT | CTTCCGCTCT | 540 |
| TCAATCTTCG | CGCCTGCTAC | TTGCCGACCG | CTTTCAATCG | 580 |
| CTTTTCTGAT | GGCGGTTTTG | TCCGGTTCGG | TTTTGACGGC | 620 |
| CTCACGCATA | AATTCGGCGG | GGATTTGTGC | TTCGTCTAAG | 680 |
| ATCACGACGG | CTTCGGATTT | GCGGAACGAG | GCTTTAAAAG | 720 |
| TGCCGTC | | | | 760 |

To illustrate, nucleic acid detection reagents comprising SEQ ID NOS: 37-45, or complements thereof, target NGDR9Var or complements thereof SEQ ID NOS: 37-45 are shown in Table B:

TABLE B

| | |
|---|---|
| SEQ ID NO: 37 | 5'-GTTTCGACAGGCTTGCGAAC-3' |
| SEQ ID NO: 38 | 5'-GTTTCGACAGGCTTGCGAA-3' |
| SEQ ID NO: 39 | 5'-TTTGTTGTTGCCGTTTGCA-3' |
| SEQ ID NO: 40 | 5'-CCTGTTTGCGACAAAGAGGA-3' |
| SEQ ID NO: 41 | 5'-TGCGACAAAGAGGATTCCAA-3' |
| SEQ ID NO: 42 | 5'-TTCCCGCGCCTGCCTGATTCCTA-3' |
| SEQ ID NO: 43 | 5'-ACATCCGCACCGTAGGAATCAGGCA-3' |
| SEQ ID NO: 44 | 5'-AATCCCGACATCCGCACCGTAGGAATCA-3' |
| SEQ ID NO: 45 | 5'-AATCCCGACATCCGCACCGTAGGAAT-3' |

Other nucleic acid detection reagents of the invention target both NGDR9 and NGDR9Var. To illustrate, nucleic acid detection reagents comprising SEQ ID NOS: 46-60, 68-70, or complements thereof, target NGDR9 and NGDR9Var or complements thereof. These sequences can also be termed "universal" sequences. SEQ ID NOS: 46-60 and 68-70 are shown in Table C:

TABLE C

| SEQ ID NO: 46 | 5'-CGTTTGGCGGCAAGCATC-3' |
| --- | --- |
| SEQ ID NO: 47 | 5'-GCGGCAAGCATCTGTTTTGC-3' |
| SEQ ID NO: 48 | 5'-GTAGCAGGCGCGAAGATTGAA-3' |
| SEQ ID NO: 49 | 5'-AGTAGCAGGCGCGAAGATTGA-3' |
| SEQ ID NO: 50 | 5'-GGGCGGAAGAATTTGCAGATTA-3' |
| SEQ ID NO: 51 | 5'-GCCATCAGAAAGCGATTGAAA-3' |
| SEQ ID NO: 52 | 5'-GGACAAAACCGCCATCAGAAA-3' |
| SEQ ID NO: 53 | 5'-TAATCTGCAAATTCTTCCGCCCTTCAATCTT-3' |
| SEQ ID NO: 54 | 5'-TTTATCTAATCTGCAAATTCTTCCGCCCTTCA-3' |
| SEQ ID NO: 55 | 5'-CAAATTCTTCCGCCCTTCAATCTTCGC-3' |
| SEQ ID NO: 56 | 5'-CTTCAATCTTCGCGCCTGCTACTTGCC-3' |
| SEQ ID NO: 57 | 5'-AAGATTGAAGGGCGGAAGAATTTGCAGATTA-3' |
| SEQ ID NO: 58 | 5'-GCGAAGATTGAAGGGCGGAAGAATTTG-3' |
| SEQ ID NO: 59 | 5'-TCAGGGCTTCGTCTTCCGA-3' |
| SEQ ID NO: 60 | 5'-TTTAAAGCCTCGTTCCGCAA-3' |
| SEQ ID NO: 68 | 5'-TCAATCTTCGCGCCTGCTAC-3' |
| SEQ ID NO: 69 | 5'-AAAGCCTCGTTCCGCAAATC-3' |
| SEQ ID NO: 70 | 5'-AAACCGAACCGGACAAAACCGCCAT-3' |

As mentioned above, nucleic acid detection reagents comprise oligonucleotides (e.g., probe nucleic acids, primer nucleic acids, etc.) in certain embodiments of the invention. Although other lengths are optionally utilized, oligonucleotides generally comprise sequences that are typically between about 8 and about 100 nucleotides in length, more typically between about 10 and about 75 nucleotides in length, still more typically between about 12 and about 50 nucleotides in length, and even more typically between about 15 and about 35 nucleotides in length (e.g., about 20, about 25, or about 30 nucleotides in length). Methods of preparing oligonucleotides, such as nucleic acid synthesis, are described further below.

Various approaches can be utilized by one of skill in the art to design oligonucleotides (e.g., substantially identical variants of nucleic acids having sequences selected from SEQ ID NOS: 3-27, 37-60, and 68-70, or complements thereof) that selectively bind to NGDR9 and/or NGDG9Var, or NGDR33, which oligonucleotides can be used to detect *N. gonorrhoeae*. To illustrate, the DNAstar software package available from DNASTAR, Inc. (Madison, Wis.) can be used for sequence alignments. For example, nucleic acid sequences for NGDR9 and *B. suis* or NGDR33 and *N. meningitidis* can be uploaded into DNAstar EditSeq program as individual files. Pairs of sequence files (e.g., NGDR9 and *B. suis*) can be opened in the DNAstar MegAlign sequence alignment program and the Clustal W method of alignment can be applied. The parameters used for Clustal W alignments are optionally the default settings in the software. MegAlign typically does not provide a summary of the percent identity between two sequences. This is generally calculated manually. From the alignments, regions having, e.g., less than 85% identity with one another are typically identified and oligonucleotide sequences in these regions can be selected. Many other sequence alignment algorithms and software packages are also optionally utilized. Sequence alignment algorithms are also described in, e.g., Mount, *Bioinformatics: Sequence and Genome Analysis*, Cold Spring Harbor Laboratory Press (2001), and Durbin et al., *Biological Sequence Analysis: Probabilistic Models of Proteins and Nucleic Acids*, Cambridge University Press (1998), which are both incorporated by reference.

To further illustrate, optimal alignment of sequences for comparison can be conducted, e.g., by the local homology algorithm of Smith & Waterman (1981) *Adv. Appl. Math.* 2:482, by the homology alignment algorithm of Needleman & Wunsch (1970) *J. Mol. Biol.* 48:443, by the search for similarity method of Pearson & Lipman (1988) *Proc. Nat'l. Acad. Sci. USA* 85:2444, which are each incorporated by reference, and by computerized implementations of these algorithms (GAP, BESTFIT, FASTA, and TFASTA in the Wisconsin Genetics Software Package, Genetics Computer Group (Madison, Wis.), or by even by visual inspection.

Another example algorithm that is suitable for determining percent sequence identity is the BLAST algorithm, which is described in, e.g., Altschul et al. (1990) *J. Mol. Biol.* 215:403-410, which is incorporated by reference. Software for performing versions of BLAST analyses is publicly available through the National Center for Biotechnology Information on the world wide web at ncbi.nlm.nih.gov/ as of Mar. 12, 2004. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see, Henikoff & Henikoff (1989) *Proc. Natl. Acad. Sci. USA* 89:10915, which is incorporated by reference).

In addition to calculating percent sequence identity, the BLAST algorithm also performs a statistical analysis of the similarity between two sequences (see, e.g., Karlin & Altschul (1993) *Proc. Nat'l. Acad. Sci. USA* 90:5873-5787, which is incorporated by reference). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence (and, therefore, homologous) if the smallest sum probability in a comparison of the test nucleic acid to the reference nucleic acid is less than about 0.1, or less than about 0.01, and or even less than about 0.001.

An additional example of a useful sequence alignment algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle (1987) *J. Mol. Evol.* 35:351-360, which is incorporated by reference. The method used is similar to the method described by Higgins & Sharp (1989) *CABIOS* 5:151-153, which is incorporated by reference. The program can align, e.g., up to 300 sequences of a maximum length of 5,000 letters. The multiple alignment procedure begins with the pairwise alignment of the two most similar sequences, producing a cluster of two aligned sequences. This cluster can then be aligned to the next most related sequence or cluster of aligned sequences. Two clusters of sequences can be aligned by a simple extension of the pairwise alignment of two individual sequences. The final alignment is achieved by a series of progressive, pairwise alignments. The program can also be used to plot a dendogram or tree representation of clustering relationships. The program is run by designating specific sequences and their amino acid or nucleotide coordinates for regions of sequence comparison.

The probes and primers of the invention optionally include one or more labels, which are described further below. In addition, probes and primers optionally include various other modifications, such as modified nucleotides that alter hybridization melting temperatures, restriction site linkers to facilitate amplicon cloning, modifier groups that increase the specificity of nucleic acid amplification reactions, and/or the like. For example, certain modified nucleotides that increase nucleic acid hybridization melting temperatures are optionally included to permit the use of smaller probes and primers, such as those including between about 8 and about 14 nucleotides. Examples of these modified oligonucleotides include those having one or more LNA™ monomers. Nucleotide analogs such as these are described further in, e.g., U.S. Pat. No. 6,639,059, entitled "SYNTHESIS OF [2.2.1]BICYCLO NUCLEOSIDES," issued Oct. 28, 2003 to Kochkine et al., U.S. Pat. No. 6,303,315, entitled "ONE STEP SAMPLE PREPARATION AND DETECTION OF NUCLEIC ACIDS IN COMPLEX BIOLOGICAL SAMPLES," issued Oct. 16, 2001 to Skouv, and U.S. Pat. Application Pub. No. 2003/0092905, entitled "SYNTHESIS OF [2.2.1]BICYCLO NUCLEOSIDES," by Kochkine et al. that published May 15, 2003, which are each incorporated by reference. Oligonucleotides comprising LNA™ monomers are commercially available through, e.g., Exiqon A/S (Vedbæk, DK). Additional probe and primer modifications are referred to herein, including in the definitions provided above.

In certain embodiments, the nucleic acid detection reagents utilized as described herein are sequence specific antibodies that target SEQ ID NO: 1, SEQ ID NO: 2, SEQ ID NO: 36, a substantially identical variant thereof in which the variant has at least 90% sequence identity to one of SEQ ID NOS: 1 or 2 or 36, or a complement of SEQ ID NO: 1, SEQ ID NO: 2, SEQ ID NO: 36, or the variant. SEQ ID NO: 1 and SEQ ID NO: 2 and SEQ ID NO: 36 are described further above and are provided in Tables I and II and A, respectively. Antibodies suitable for use in these embodiments of invention may be prepared by conventional methodology and/or by genetic engineering. Antibody fragments may be genetically engineered, e.g., from the variable regions of the light and/or heavy chains ($V_H$ and $V_L$), including the hypervariable regions, or from both the $V_H$ and $V_L$ regions. For example, the term "antibodies" as used herein includes polyclonal and monoclonal antibodies and biologically active fragments thereof including among other possibilities "univalent" antibodies (Glennie et al. (1982) *Nature* 295:712); Fab proteins including Fab' and F(ab')$_2$ fragments whether covalently or non-covalently aggregated; light or heavy chains alone, typically variable heavy and light chain regions ($V_H$ and $V_L$ regions), and more typically including the hypervariable regions (otherwise known as the complementarity determining regions (CDRs) of the $V_H$ and $V_L$ regions); $F_c$ proteins; "hybrid" antibodies capable of binding more than one antigen; constant-variable region chimeras; "composite" immunoglobulins with heavy and light chains of different origins; "altered" antibodies with improved specificity and other characteristics as prepared by standard recombinant techniques, by mutagenic techniques, or other directed evolutionary techniques known in the art.

The sequence specific antibodies utilized as described herein may be labeled or unlabeled. Suitable labels include, e.g., radionuclides, enzymes, coenzymes, fluorescent dyes, chemiluminescent dyes, chromogens, enzyme substrates or co-factors, enzyme inhibitors, free radicals, and the like. Such labeled reagents may be used in a variety of well known assays, such as radioimmunoassays, enzyme immunoassays, e.g., ELISA, fluorescent immunoassays, and the like. See, e.g., U.S. Pat. Nos. 3,766,162; 3,791,932; 3,817,837; and 4,233,402, which are each incorporated by reference. Additional labels are described further herein.

In some embodiments, transcribed RNAs and/or translated proteins encoded by NGDR9 and NGDR33 and NGDR9Var are targeted for detection. Many techniques for detecting RNAs and/or proteins are known in the art. For example, probe and primer nucleic acids of the invention can be adapted for use in reverse transcription-polymerase chain reaction (RT-PCR) assays for the detection of NGDR9 and/or NGDR9Var, or NGDR33 transcription products. Moreover, various electrophoretic assays (e.g., SDS-PAGE or the like), immunoassays, mass spectrometric assays (e.g., matrix assisted laser desorption/ionization (MALDI)-based analyses, surface enhanced laser desorption/ionization (SELDI)-based assays, etc.), and/or other approaches can be used to detect proteins encoded by NGDR9 and/or NGDR9Var, or NGDR33. Many of these and other suitable RNA and protein detection methods are described in the references cited herein.

In practicing the present invention, many conventional techniques in molecular biology and recombinant DNA are optionally used. These techniques are well known and are explained in, for example, *Current Protocols in Molecular Biology*, Volumes I, II, and III, 1997 (F. M. Ausubel ed.); Sambrook et al., *Molecular Cloning: A Laboratory Manual*, 3rd Ed., Cold Spring Harbor Laboratory Press, Cold Spring Harbor, N.Y., 2001; Berger and Kimmel, *Guide to Molecular Cloning Techniques, Methods in Enzymology* volume 152 Academic Press, Inc., San Diego, Calif. (Berger), *DNA Cloning: A Practical Approach*, Volumes I and II, 1985 (D. N. Glover ed.); *Oligonucleotide Synthesis*, 1984 (M. L. Gait ed.); *Nucleic Acid Hybridization*, 1985, (Hames and Higgins); *Transcription and Translation*, 1984 (Hames and Higgins eds.); *Animal Cell Culture*, 1986 (Freshney ed.); *Immobilized Cells and Enzymes*, 1986 (IRL Press); Perbal, 1984, *A Practical Guide to Molecular Cloning*; the series, *Methods in Enzymology* (Academic Press, Inc.); *Gene Transfer Vectors for Mammalian Cells*, 1987 (J. H. Miller and M. P. Calos eds., Cold Spring Harbor Laboratory); *Methods in Enzymology* Vol. 154 and Vol. 155 (Wu and Grossman, and Wu, eds., respectively), all of which are incorporated by reference.

IV. Sequence Variations

Numerous nucleic acid and polypeptide sequences are within the scope of the present invention. To illustrate, FIG. 1 shows a sequence alignment of the *Neisseria gonorrhoeae* Direct Repeat 9 (NGDR9) sequence with the sequences of at least portions of amplicons of genomic DNA from various *N. gonorrhoeae* strains. More specifically, genomic DNA from 5 *N. gonorrhoea* strains (i.e., NG strains 1117, 1120, 6346, 6359, and 6364) was amplified and sequenced with primer nucleic acids corresponding to DK101 (SEQ ID NO: 7) and DK102R (SEQ ID NO: 25). The location of the oligonucleotides DK101 and the complement to DK102R (i.e., DK102 (SEQ ID NO: 8)) and the oligonucleotides NG519 (SEQ ID NO: 5) and NG514 (SEQ ID NO: 6) are underlined in the sequence of NGDR9 shown in FIG. 1. In addition, the majority or consensus sequence between the DR9 sequence and the five *N. gonorrhoeae* strains is also indicated.

To further illustrate, certain exemplary NGDR9-related nucleic acid sequence variations are associated with Gene ID numbers NG0465, NG0466, NG0467, IGR0389, IGR0390, NG1616, NG1617, NG1618, IGR1318, and IGR1319, and certain exemplary NGDR33-related nucleic acid sequence variations are associated with Gene ID numbers NG0518, NG0519, NG0520, IGR0430, IGR0431, NG1649, NG1650, IGR1345, and IGR1346, all of which are provided on the world wide web at stdgen.lanl.gov as of Mar. 12, 2004. However, the NGDR9Var sequence (SEQ ID NO: 36) has not been found in any publicly accessible databases as of Aug. 1, 2007. SEQ ID NO: 36 was surprisingly identified during an extensive sequence analysis study of the NGDR9 Region.

Silent Variations

It will be appreciated by those skilled in the art that due to the degeneracy of the genetic code, a multitude of nucleic acids sequences encoding NGDR9 and NGDR33 and NGDR9Var polypeptides may be produced, some of which may bear minimal sequence homology to the nucleic acid sequences explicitly disclosed herein. Exemplary NGDR9 polypeptides are associated with Gene ID numbers NG0465, NG0466, NG0467, NG1616, NG1617, and NG1618, and exemplary NGDR33 polypeptides are associated with Gene ID numbers NG0518, NG0519, NG0520, NG1649, and NG1650, all of which are provided on the world wide web at stdgen.lanl.gov as of Mar. 12, 2004.

TABLE VII

Codon Table

| Amino acids | | | Codon | | | | | |
|---|---|---|---|---|---|---|---|---|
| Alanine | Ala | A | GCA | GCC | GCG | GCU | | |
| Cysteine | Cys | C | UGC | UGU | | | | |
| Aspartic acid | Asp | D | GAC | GAU | | | | |
| Glutamic acid | Glu | E | GAA | GAG | | | | |
| Phenylalanine | Phe | F | UUC | UUU | | | | |
| Glycine | Gly | G | GGA | GGC | GGG | GGU | | |
| Histidine | His | H | CAC | CAU | | | | |
| Isoleucine | Ile | I | AUA | AUC | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

For instance, inspection of the codon table (Table VII) shows that codons AGA, AGG, CGA, CGC, CGG, and CGU all encode the amino acid arginine. Thus, at every position in the nucleic acids of the invention where an arginine is specified by a codon, the codon can be altered to any of the corresponding codons described above without altering the encoded polypeptide. It is understood that U in an RNA sequence corresponds to T in a DNA sequence.

Such "silent variations" are one species of "conservatively modified variations", discussed below. One of skill will recognize that each codon in a nucleic acid (except AUG, which is ordinarily the only codon for methionine) can be modified by standard techniques to encode a functionally identical polypeptide. Accordingly, each silent variation of a nucleic acid which encodes a polypeptide is implicit in any described sequence. The invention provides each and every possible variation of nucleic acid sequence encoding NGDR9 and NGDR33 and NGDR9Var polypeptides that could be made by selecting combinations based on possible codon choices. These combinations are made in accordance with the standard triplet genetic code (e.g., as set forth in Table 1) as applied to the nucleic acid sequences encoding NGDR9 and NGDR33 and NGDR9Var polypeptides. All such variations of every nucleic acid herein are specifically provided and described by consideration of the sequence in combination with the genetic code.

Conservative Variations

"Conservatively modified variations" or, simply, "conservative variations" of a particular nucleic acid sequence refers to those nucleic acids, which encode identical or essentially identical amino acid sequences, or, where the nucleic acid does not encode an amino acid sequence, to essentially identical sequences. One of skill will recognize that individual substitutions, deletions or additions which alter, add or delete a single amino acid or a small percentage of amino acids (typically less than 5%, more typically less than 4%, 2% or 1%) in an encoded sequence are "conservatively modified variations" where the alterations result in the deletion of an amino acid, addition of an amino acid, or substitution of an amino acid with a chemically similar amino acid.

Conservative substitution tables providing functionally similar amino acids are well known in the art. Table VIII sets forth six groups, which contain amino acids that are "conservative substitutions" for one another.

TABLE VIII

Conservative Substitution Groups

| | | |
|---|---|---|
| 1 Alanine (A) | Serine (S) | Threonine (T) |
| 2 Aspartic acid (D) | Glutamic acid (E) | |
| 3 Asparagine (N) | Glutamine (Q) | |
| 4 Arginine (R) | Lysine (K) | |
| 5 Isoleucine (I) | Leucine (L) | Methionine (M) Valine (V) |
| 6 Phenylalanine (F) | Tyrosine (Y) | Tryptophan (W) |

Thus, "conservatively substituted variations" of a NGDR9 or a NGDR33 or a NGDR9Var polypeptide referred to herein include substitutions of a small percentage, typically less than 5%, more typically less than 2% or 1%, of the amino acids of the polypeptide sequence, with a conservatively selected amino acid of the same conservative substitution group.

The addition of sequences that do not alter the encoded activity of a nucleic acid molecule, such as the addition of a non-functional sequence, is a conservative variation of the basic nucleic acid.

One of skill will appreciate that many conservative variations of the nucleic acids described herein yield a functionally identical nucleic acid. For example, as discussed above, owing to the degeneracy of the genetic code, "silent substitutions" (i.e., substitutions in a nucleic acid sequence which do not result in an alteration in an encoded polypeptide) are an implied feature of every nucleic acid sequence, which encodes an amino acid. Similarly, "conservative amino acid substitutions," in one or a few amino acids in an amino acid sequence are substituted with different amino acids with highly similar properties, are also readily identified as being highly similar to a disclosed construct. Such conservative variations of each disclosed sequence are a feature of the present invention.

V. Probe and Primer Synthesis

The oligonucleotide probes and primers of the invention are optionally prepared using essentially any technique known in the art. In certain embodiments, for example, the oligonucleotide probes and primers described herein are synthesized chemically using essentially any nucleic acid synthesis method, including, e.g., according to the solid phase phosphoramidite triester method described by Beaucage and Caruthers (1981), *Tetrahedron Letts.* 22(20):1859-1862, which is incorporated by reference, or another synthesis technique known in the art, e.g., using an automated synthesizer, as described in Needham-VanDevanter et al. (1984) *Nucleic Acids Res.* 12:6159-6168, which is incorporated by reference. A wide variety of equipment is commercially available for automated oligonucleotide synthesis. Multi-nucleotide synthesis approaches (e.g., tri-nucleotide synthesis, etc.) are also optionally utilized. Moreover, the primer nucleic acids described herein optionally include various modifications. In certain embodiments, for example, primers include restriction site linkers, e.g., to facilitate subsequent amplicon cloning or the like. To further illustrate, primers are also optionally modified to improve the specificity of amplification reactions as described in, e.g., U.S. Pat. No. 6,001,611, entitled "MODIFIED. NUCLEIC ACID AMPLIFICATION PRIMERS," issued Dec. 14, 1999 to Will, which is incorporated by reference. Primers and probes can also be synthesized with various other modifications as described herein or as otherwise known in the art.

Essentially any label is optionally utilized to label the nucleic acid detection reagents of the invention. In some embodiments, for example, the label comprises a fluorescent dye (e.g., a rhodamine dye (e.g., R6G, R110, TAMRA, ROX, etc.), a fluorescein dye (e.g., JOE, VIC, TET, HEX, FAM, etc.), a halofluorescein dye, a cyanine dye (e.g., CY3, CY3.5, CY5, CY5.5, etc.), a BODIPY® dye (e.g., FL, 530/550, TR, TMR, etc.), an ALEXA FLUOR® dye (e.g., 488, 532, 546, 568, 594, 555, 653, 647, 660, 680, etc.), a dichlororhodamine dye, an energy transfer dye (e.g., BIGDYE™ v 1 dyes, BIGDYE™ v 2 dyes, BIGDYE™ v 3 dyes, etc.), Lucifer dyes (e.g., Lucifer yellow, etc.), CASCADE BLUE®, Oregon Green, and the like. Additional examples of fluorescent dyes are provided in, e.g., Haugland, *Molecular Probes Handbook of Fluorescent Probes and Research Products*, Ninth Ed. (2003) and the updates thereto, which are each incorporated by reference. Fluorescent dyes are generally readily available from various commercial suppliers including, e.g., Molecular Probes, Inc. (Eugene, Oreg.), Amersham Biosciences Corp. (Piscataway, N.J.), Applied Biosystems (Foster City, Calif.), etc. Other labels include, e.g., biotin, weakly fluorescent labels (Yin et al. (2003) *Appl Environ Microbiol.* 69(7):3938, Babendure et al. (2003) *Anal. Biochem.* 317(1):1, and Jankowiak et al. (2003) *Chem Res Toxicol.* 16(3):304), non-fluorescent labels, colorimetric labels, chemiluminescent labels (Wilson et al. (2003) *Analyst.* 128(5):480 and Roda et al. (2003) *Luminescence* 18(2):72), Raman labels, electrochemical labels, bioluminescent labels (Kitayama et al. (2003) *Photochem Photobiol.* 77(3):333, Arakawa et al. (2003) *Anal. Biochem.* 314(2):206, and Maeda (2003) *J. Pharm. Biomed. Anal.* 30(6):1725), and an alpha-methyl-PEG labeling reagent as described in, e.g., U.S. Provisional Patent Application No. 60/428,484, filed on Nov. 22, 2002, which references are each incorporated by reference. Nucleic acid labeling is also described further below.

In addition, essentially any nucleic acid (and virtually any labeled nucleic acid, whether standard or non-standard) can be custom or standard ordered from any of a variety of commercial sources, such as The Midland Certified Reagent Company, The Great American Gene Company, ExpressGen Inc., Operon Technologies Inc., Proligo LLC, and many others.

VI. Sample Preparation and Nucleic Acid Amplification

Samples are generally derived or isolated from subjects, typically mammalian subjects, more typically human subjects, suspected of having an *N. gonorrhoeae* and/or *C. trachomatis* infections. Exemplary samples or specimens include blood, plasma, serum, urine, synovial fluid, seminal fluid, seminal plasma, prostatic fluid, vaginal fluid, cervical fluid, uterine fluid, cervical scrapings, amniotic fluid, anal scrapings, mucus, sputum, tissue, and the like. Essentially any technique for acquiring these samples is optionally utilized including, e.g., scraping, venipuncture, swabbing, biopsy, or other techniques known in the art. To further illustrate, throat swabs are taken from subjects in certain embodiments, e.g., as part of screens for gonococcal pharyngitis or the like.

Methods of storing specimens, culturing cells, isolating and preparing nucleic acids from these sources are generally known in the art and many of these are described further in the references and/or examples provided herein.

To further illustrate, prior to analyzing the target nucleic acids described herein, those nucleic acids may be purified or isolated from samples that typically include complex mixtures of different components. Cells in collected samples are typically lysed to release the cell contents. For example, *N. gonorrhoeae* and other cells in the particular sample can be lysed by contacting them with various enzymes, chemicals, and/or lysed by other approaches known in the art, which degrade, e.g., bacterial cell walls. In some embodiments, nucleic acids are analyzed directly in the cell lysate. In other embodiments, nucleic acids are further purified or extracted from cell lysates prior to detection. Essentially any nucleic acid extraction methods can be used to purify nucleic acids in the samples utilized in the methods of the present invention. Exemplary techniques that can be used to purifying nucleic acids include, e.g., affinity chromatography, hybridization to probes immobilized on solid supports, liquid-liquid extraction (e.g., phenol-chloroform extraction, etc.), precipitation (e.g., using ethanol, etc.), extraction with filter paper, extraction with micelle-forming reagents (e.g., cetyl-trimethyl-ammonium-bromide, etc.), binding to immobilized intercalating dyes (e.g., ethidium bromide, acridine, etc.), adsorption to silica gel or diatomic earths, adsorption to magnetic glass particles or organo silane particles under chaotropic conditions, and/or the like. Sample processing is also described in, e.g., U.S. Pat. Nos. 5,155,018, 6,383,393, and 5,234,809, which are each incorporated by reference.

To further exemplify, unmodified nucleic acids can bind to a material with a silica surface. Many of these processes that are optionally adapted for use in the performing the methods of the present invention are described in the art. To illustrate, Vogelstein et al. (1979) *Proc. Natl. Acad. Sci. USA* 76:615-619, which is incorporated by reference, describes the purification of nucleic acids from agarose gels in the presence of sodium iodide using ground flint glass. Marko et al. (1982) *Anal. Biochem.* 121:382-387, which is incorporated by reference, describes the purification of nucleic acids from bacteria on glass dust in the presence of sodium perchlorate. In DE-A 3734442, which is incorporated by reference, nucleic acids are isolated on glass fiber filters. The nucleic acids bound to these glass fiber filters are washed and then eluted with a methanol-containing Tris/EDTA buffer. A similar procedure is described in Jakobi et al. (1988) *Anal. Biochem.* 175:196-201, which is incorporated by reference. In particular, Jakobi et al. describes the selective binding of nucleic acids to glass surfaces in chaotropic salt solutions and separating the nucleic acids from contaminants, such as agarose, proteins, and cell residue. To separate the glass particles from the contaminants, the particles can be centrifuged or fluids can be drawn through the glass fiber filters. In addition, the use of magnetic particles to immobilize nucleic acids after precipitation by adding salt and ethanol is described in, e.g., Alderton et al. (1992) *Anal. Biochem.* 201:166-169 and PCT/GB91/00212, which are both incorporated by reference. In this procedure, the nucleic acids are agglutinated along with the magnetic particles. The agglutinate is separated from the original solvent by applying a magnetic field and performing one or more washing steps. After at least one wash step, the nucleic acids are typically dissolved in a Tris buffer.

Magnetic particles in a porous glass matrix that is covered with a layer that includes, e.g., streptavidin can also be utilized in certain embodiments of the invention. These particles can be used, e.g., to isolate biotin-conjugated nucleic acids and proteins. Ferrimagnetic, ferromagnetic, and superparamagnetic particles are also optionally utilized. Magnetic glass particles and related methods that can be adapted for using in performing the methods described herein are also described in, e.g., WO 01/37291, which is incorporated by reference.

One of the most powerful and basic technologies for deriving and detecting nucleic acids is nucleic acid amplification. In the present invention, amplification of nucleic acids of interest typically precedes or is concurrent with the detection of that DNA. In addition, the oligonucleotide probes described herein are also optionally amplified, e.g., following chemical synthesis or the like. In some embodiments, detectable signals are amplified, e.g., using branched nucleic acid or other signal amplification formats known in the art.

Amplification methods that are optionally utilized or adapted for use with the oligonucleotides and methods described herein include, e.g., various polymerase or ligase mediated amplification methods, such as the polymerase chain reaction (PCR), the ligase chain reaction (LCR), strand displacement amplification (SDA), nucleic acid sequence-based amplification (NASBA), rolling circle amplification (RCA), and/or the like. Details regarding the use of these and other amplification methods can be found in various articles and/or any of a variety of standard texts, including, e.g., Berger, Sambrook, Ausubel, and *PCR Protocols A Guide to Methods and Applications* (Innis et al. eds) Academic Press, Inc., San Diego, Calif. (1990) (Innis), Schweitzer et al. (2001) "Combining nucleic acid amplification and detection," *Curr Opin Biotechnol.* 12(1):21-27, all of which are incorporated by reference. Many available biology texts also have extended discussions regarding PCR and related amplification methods. Nucleic acid amplification is also described in, e.g., Mullis et al., (1987) U.S. Pat. No. 4,683,202 and Sooknanan and Malek (1995) *Biotechnology* 13:563, which are both incorporated by reference. Improved methods of amplifying large nucleic acids by PCR are summarized in Cheng et al. (1994) *Nature* 369:684, which is incorporated by reference. In certain embodiments, duplex PCR is utilized to amplify target nucleic acids. Duplex PCR amplification is described further in, e.g., Gabriel et al. (2003) "Identification of human remains by immobilized sequence-specific oligonucleotide probe analysis of mtDNA hypervariable regions I and II," *Croat. Med. J.* 44(3)293 and La et al. (2003) "Development of a duplex PCR assay for detection of *Brachyspira hyodysenteriae* and *Brachyspira pilosicoli* in pig feces," *J. Clin. Microbiol.* 41(7):3372, which are both incorporated by reference. Optionally, labeled primers (e.g., biotinylated primers, Scorpion primers, etc.) are utilized to amplify nucleic acids in a sample, e.g., to facilitate the detection of amplicons and the like. Scorpion primers are also described in, e.g., Whitcombe et al. (1999) "Detection of PCR products using self-probing amplicons and fluorescence" *Nat. Biotechnol.* 17(8):804-807, which is incorporated by reference. Labeling is described further herein.

Amplicons are optionally recovered and purified from other reaction components by any of a number of methods well known in the art, including electrophoresis, chromatography, precipitation, dialysis, filtration, and/or centrifugation. Aspects of nucleic acid purification are described in, e.g., Douglas et al., *DNA Chromatography*, Wiley, John & Sons, Inc. (2002), and Schott, *Affinity Chromatography: Template Chromatography of Nucleic Acids and Proteins*, Chromatographic Science Series, #27, Marcel Dekker (1984), all of which are incorporated by reference. In certain embodiments, amplicons are not purified prior to detection. The detection of amplicons is described further below.

VII. Probe Arrays

In certain embodiments of the invention, the oligonucleotide probes described herein are covalently or noncovalently attached to solid supports which are then contacted with samples comprising amplified and labeled nucleic acid from a subject. In other embodiments, the probes of the invention are provided free in solution. Essentially any substrate material is optionally adapted for use in these aspects of the invention. In certain embodiments, for example, substrates are fabricated from silicon, glass, or polymeric materials (e.g., glass or polymeric microscope slides, silicon wafers, etc.). Suitable glass or polymeric substrates, including microscope slides, are available from various commercial suppliers, such as Fisher Scientific (Pittsburgh, Pa.) or the like. In some embodiments, solid supports utilized in the invention are membranes. Suitable membrane materials are optionally selected from, e.g. polyaramide membranes, polycarbonate membranes, porous plastic matrix membranes (e.g., POREX® Porous Plastic, etc.), porous metal matrix membranes, polyethylene membranes, poly(vinylidene difluoride) membranes, polyamide membranes, nylon membranes, ceramic membranes, polyester membranes, polytetrafluoroethylene (TEFLON®) membranes, woven mesh membranes, microfiltration membranes, nanofiltration membranes, ultrafiltration membranes, dialysis membranes, composite membranes, hydrophilic membranes, hydrophobic membranes, polymer-based membranes, a non-polymer-based membranes, powdered activated carbon membranes, polypropylene membranes, glass fiber membranes, glass membranes, nitrocellulose membranes, cellulose membranes, cellulose nitrate membranes, cellulose acetate membranes, polysulfone membranes, polyethersulfone membranes, polyolefin membranes, or the like. Many of these membranous materials are widely available from various commercial suppliers, such as, P.J. Cobert Associates, Inc. (St. Louis, Mo.), Millipore Corporation (Bedford, Mass.), or the like. Other exemplary solid supports that are optionally utilized include, e.g., ceramics, metals, resins, gels, plates, beads, microbeads (e.g., magnetic microbeads, etc.), tubes (e.g., microtubes, etc.), whiskers, fibers, combs, single crystals, and self-assembling monolayers.

The oligonucleotide probes of the invention are directly or indirectly (e.g., via linkers, such as bovine serum albumin (BSA) or the like) attached to the supports, e.g., by any available chemical or physical method. A wide variety of linking chemistries are available for linking molecules to a wide variety of solid supports. More specifically, nucleic acids may be attached to the solid support by covalent binding such as by conjugation with a coupling agent or by non-covalent binding such as electrostatic interactions, hydrogen bonds or antibody-antigen coupling, or by combinations thereof. Typical coupling agents include biotin/avidin, biotin/streptavidin, *Staphylococcus aureus* protein A/IgG antibody $F_c$ fragment, and streptavidin/protein A chimeras (Sano et al. (1991) *Bio/Technology* 9:1378, which is incorporated by reference), or derivatives or combinations of these agents. Nucleic acids may be attached to the solid support by a photocleavable bond, an electrostatic bond, a disulfide bond, a peptide bond, a diester bond or a combination of these bonds. Nucleic acids are also optionally attached to solid supports by a selectively releasable bond such as 4,4'-dimethoxytrityl or its derivative. Derivatives which have been found to be useful include 3 or 4 [bis-(4-methoxyphenyl)]-methyl-benzoic acid, N-succinimidyl-3 or 4 [bis-(4-methoxyphenyl)]-methyl-benzoic acid, N-succinimidyl-3 or 4 [bis-(4-methoxyphenyl)]-hydroxymethyl-benzoic acid, N-succinimidyl-3 or 4 [bis-(4-methoxyphenyl)]-chloromethyl-benzoic acid, and salts of these acids.

As referred to above, oligonucleotide probes are optionally attached to solid supports via linkers between the nucleic acids and the solid support. Useful linkers include a coupling agent, as described above for binding to other or additional coupling partners, or to render the attachment to the solid support cleavable.

Cleavable attachments can be created by attaching cleavable chemical moieties between the probes and the solid support including, e.g., an oligopeptide, oligonucleotide, oligopolyamide, oligoacrylamide, oligoethylene glycerol, alkyl chains of between about 6 to 20 carbon atoms, and combinations thereof. These moieties may be cleaved with, e.g., added chemical agents, electromagnetic radiation, or enzymes. Exemplary attachments cleavable by enzymes include peptide bonds which can be cleaved by proteases, and phosphodiester bonds which can be cleaved by nucleases.

Chemical agents such as β-mercaptoethanol, dithiothreitol (DTT) and other reducing agents cleave disulfide bonds. Other agents which may be useful include oxidizing agents, hydrating agents and other selectively active compounds. Electromagnetic radiation such as ultraviolet, infrared and visible light cleave photocleavable bonds. Attachments may also be reversible, e.g., using heat or enzymatic treatment, or reversible chemical or magnetic attachments. Release and reattachment can be performed using, e.g., magnetic or electrical fields.

Array based hybridization is particularly suitable for detecting *N. gonorrhoeae* and/or *C. trachomatis* nucleic acids, as it can be used to detect the presence of many amplicons simultaneously. A number of array systems have been described and can be adapted for use with the present invention, including those available from commercial suppliers such as Affymetrix, Inc. (Santa Clara, Calif., USA) and the like. Aspects of array construction and use are also described in, e.g., Sapolsky et al. (1999) "High-throughput polymorphism screening and genotyping with high-density oligonucleotide arrays." *Genetic Analysis: Biomolecular Engineering* 14:187-192; Lockhart (1998) "Mutant yeast on drugs" *Nature Medicine* 4:1235-1236; Fodor (1997) "Genes, Chips and the Human Genome." *FASEB Journal* 11:A879; Fodor (1997) "Massively Parallel Genomics" *Science* 277: 393-395; and Chee et al. (1996) "Accessing Genetic Information with High-Density DNA Arrays" *Science* 274:610-614, all of which are incorporated by reference.

Other probes and primers for detecting *N. gonorrhoeae* and/or *C. trachomatis* nucleic acids, which are optionally utilized in addition to the probes and primer described above to perform the methods and other aspects of the invention, are described in, e.g., U.S. Pat. No. 5,550,040 to Purohit et al., and U.S. Pat. No. 6,090,557 to Weiss, which are both incorporated by reference.

VIII. Nucleic Acid Hybridization

Hybridization of oligonucleotide probes to their target *N. gonorrhoeae* and/or *C. trachomatis* nucleic acids can be accomplished by choosing the appropriate hybridization conditions. The stability of the probe:target nucleic acid hybrid is typically selected to be compatible with the assay and washing conditions so that stable, detectable hybrids form only between the probes and target *N. gonorrhoeae* and/or *C. trachomatis* nucleic acids. Manipulation of one or more of the different assay parameters determines the exact sensitivity and specificity of a particular hybridization assay.

More specifically, hybridization between complementary bases of DNA, RNA, PNA, or combinations of DNA, RNA and PNA, occurs under a wide variety of conditions that vary in temperature, salt concentration, electrostatic strength, buffer composition, and the like. Examples of these conditions and methods for applying them are described in, e.g., Tijssen (1993), supra, and Hames and Higgins, supra. Hybridization generally takes place between about 0° C. and about 70° C., for periods of from about one minute to about one hour, depending on the nature of the sequence to be hybridized and its length. However, it is recognized that hybridizations can occur in seconds or hours, depending on the conditions of the reaction. To illustrate, typical hybridization conditions for a mixture of two 20-mers is to bring the mixture to 68° C., followed by cooling to room temperature (22° C.) for five minutes or at very low temperatures such as 2° C. in 2 microliters. Hybridization between nucleic acids may be facilitated using buffers such as Tris-EDTA (TE), Tris-HCl and HEPES, salt solutions (e.g. NaCl, KCl, $CaCl_2$), or other aqueous solutions, reagents and chemicals. Examples of these reagents include single-stranded binding proteins such as RecA protein, T4 gene 32 protein, *E. coli* single-stranded binding protein and major or minor nucleic acid groove binding proteins. Other examples of such reagents and chemicals include divalent ions, polyvalent ions and intercalating substances such as ethidium bromide, actinomycin D, psoralen, and angelicin. An exemplary hybridization procedure of use in the present invention follows similar conditions as specified in the COBAS AMPLICOR® *Chlamydia trachomatis* (CT)/*Neisseria gonorrhoeae* (NG) Test protocol (Roche Diagnostics Corporation, Indianapolis, Ind.).

IX. Detection and Probe Variations

As referred to above, amplified target *N. gonorrhoeae* and/or *C. trachomatis* nucleic acid in the samples utilized in the methods of the invention is optionally labeled to permit detection of oligonucleotide probe-target hybridization duplexes. In general, a label can be any moiety that can be attached, e.g., to a primer utilized for amplification and provide a detectable signal (e.g., a quantifiable signal). Labels may be attached to a primer directly or indirectly by a variety of techniques known in the art. Depending on the type of label used, the label can be attached to a terminal (5' or 3' end of the primer) or a non-terminal nucleotide, and can be attached indirectly through linkers or spacer arms of various sizes and compositions. Using commercially available phosphoramidite reagents, one can produce oligomers containing functional groups (e.g., thiols or primary amines) at either the 5' or 3' terminus via an appropriately protected phosphoramidite, and can label such oligonucleotides using protocols described in, for example, *PCR Protocols: A Guide to Methods and Applications* (Innis et al, eds. Academic Press, Inc. (1990)). In one embodiment, the label consists of a biotin molecule covalently bound to the primer at the 5' end. The term "biotinylated primer" refers to a primer with one or more biotin molecules bound either directly to the primer or indirectly through intervening linker molecules.

To further illustrate, detection of oligonucleotide probe-target hybridization duplexes is optionally by a chemiluminescent assay using a luminol-based reagent as described in, e.g., Whitehead, et al. (1983) *Nature* 30(5):158, which is incorporated by reference, and available commercially. Following hybridization of the probe with the labeled target DNA, the biotin molecule attached to the target DNA is conjugated, e.g., to streptavidin-horseradish peroxidase (SA-HRP). Alternatively, the target DNA can be labeled with horseradish peroxidase directly, thereby eliminating the separate conjugation step. In either case, subsequent oxidation of luminol by the horseradish peroxidase enzyme results in the emission of photons, which is then detected, e.g., on standard autoradiography film. The intensity of the signal is a function of DNA quantity. A series of DNA standards containing known amounts of DNA are typically assayed along with one or more unknown samples. The signal intensities of the known DNA standards allow an empirical determination of the functional relationship between signal intensity and DNA quantity, which enables the quantitation of the unknown samples. Many other methods of detection are also optionally utilized to perform the methods of the invention and are referred to in the references cited herein and/or generally known in the art.

Any available method for detecting *N. gonorrhoeae* and/or *C. trachomatis* amplicons can be used in the present invention. Common approaches include real time amplification detection with molecular beacons or 5'-nuclease probes, detection of intercalating dyes, detection of labels incorporated into the amplification probes or the amplified nucleic acids themselves, e.g., following electrophoretic separation of the amplification products from unincorporated label), hybridization based assays (e.g., array based assays) and/or detection of secondary reagents that bind to the nucleic acids. For example, NG and/or CT is detected using the oligonucleotides described herein in an AMPLICOR® testing format in certain embodiments of the invention.

To further illustrate, a molecular beacon or a 5'-nuclease probe is optionally designed to include a oligonucleotide probe of the invention (i.e., is selected from SEQ ID NOS: 3-27) or complements thereto), which molecular beacon or 5'-nuclease probe can be used to detect *N. gonorrhoeae* and/or *C. trachomatis* amplicons. Molecular beacons or 5'-nuclease probes are described further below. Details on these general approaches are found in the references cited herein, e.g., Sambrook and Ausubel. Additional labeling strategies for labeling nucleic acids and corresponding detection strategies can be found, e.g., in Haugland (2003) *Handbook of Fluorescent Probes and Research Chemicals Ninth Edition* by Molecular Probes, Inc. (Eugene, Oreg.), which is incorporated by reference.

Molecular beacons (MBs) are oligonucleotides designed for real time detection and quantification of target nucleic acids (e.g., target *N. gonorrhoeae* and/or *C. trachomatis* amplicons). The 5' and 3' termini of MBs collectively comprise a pair of moieties which confers the detectable properties of the MB. One of the termini is attached to a fluorophore and the other is attached to a quencher molecule capable of quenching a fluorescent emission of the fluorophore. For example, one example fluorophore-quencher pair can use a fluorophore such as EDANS or fluorescein, e.g., on the 5'-end and a quencher such as Dabcyl, e.g., on the 3'-end. When the MB is present free in solution, i.e., not hybridized to a second nucleic acid, the stem of the MB is stabilized by complementary base pairing. This self-complementary pairing results in a "hairpin loop" structure for the MB in which the fluorophore and the quenching moieties are proximal to one another. In this confirmation, the fluorescent moiety is quenched by the fluorophore. The loop of the molecular beacon typically comprises an oligonucleotide probe described herein (i.e., is selected from SEQ ID NOS: 3-27, 37-60, and 68-70, or complements thereto) and is accordingly complementary to a sequence to be detected in the target *N. gonorrhoeae* and/or *C. trachomatis* nucleic acid, such that hybridization of the loop to its complementary sequence in the target forces disassociation of the stem, thereby distancing the fluorophore and quencher from each other. This results in unquenching of the fluorophore, causing an increase in fluorescence of the MB.

Details regarding standard methods of making and using MBs are well established in the literature and MBs are available from a number of commercial reagent sources. Further details regarding methods of MB manufacture and use are found, e.g., in Leone et al. (1995) "Molecular beacon probes combined with amplification by NASBA enable homogenous real-time detection of RNA," *Nucleic Acids Res.* 26:2150-2155; Hsuih et al. (1997) "Novel, ligation-dependent PCR assay for detection of hepatitis C in serum" *J Clin Microbiol* 34:501-507; Kostrikis et al. (1998) "Molecular beacons: spectral genotyping of human alleles" *Science* 279:1228-1229; Sokol et al. (1998) "Real time detection of DNA:RNA hybridization in living cells" *Proc. Natl. Acad. Sci. U.S.A.* 95:11538-11543; Tyagi et al. (1998) "Multicolor molecular beacons for allele discrimination" *Nature Biotechnology* 16:49-53; Fang et al. (1999) "Designing a novel molecular beacon for surface-immobilized DNA hybridization studies"

*J. Am. Chem. Soc.* 121:2921-2922; and Marras et al. (1999) "Multiplex detection of single-nucleotide variation using molecular beacons" *Genet. Anal. Biomol. Eng.* 14:151-156, all of which are incorporated by reference. Aspects of MB construction and use are also found in patent literature, such as U.S. Pat. No. 5,925,517 (Jul. 20, 1999) to Tyagi et al. entitled "Detectably labeled dual conformation oligonucleotide probes, assays and kits;" U.S. Pat. No. 6,150,097 to Tyagi et al (Nov. 21, 2000) entitled "Nucleic acid detection probes having non-FRET fluorescence quenching and kits and assays including such probes" and U.S. Pat. No. 6,037,130 to Tyagi et al (Mar. 14, 2000), entitled "Wavelength-shifting probes and primers and their use in assays and kits," all of which are incorporated by reference.

MB components (e.g., oligos, including those labeled with fluorophores or quenchers) can be synthesized using conventional methods. Some of these methods are described further above. For example, oligonucleotides or peptide nucleic acids (PNAs) can be synthesized on commercially available automated oligonucleotide/PNA synthesis machines using standard methods. Labels can be attached to the oligonucleotides or PNAs either during automated synthesis or by post-synthetic reactions which have been described before see, e.g., Tyagi and Kramer (1996), supra. Aspects relating to the synthesis of functionalized oligonucleotides can also be found in Nelson, et al. (1989) "Bifunctional Oligonucleotide Probes Synthesized Using A Novel CPG Support Are Able To Detect Single Base Pair Mutations" *Nucleic Acids Res.* 17:7187-7194, which is incorporated by reference. Labels/quenchers can be introduced to the oligonucleotides or PNAs, e.g., by using a controlled-pore glass column to introduce, e.g., the quencher (e.g., a 4-dimethylaminoazobenzene-4'-sulfonyl moiety (DABSYL). For example, the quencher can be added at the 3' end of oligonucleotides during automated synthesis; a succinimidyl ester of 4-(4'-dimethylaminophenylazo)benzoic acid (DABCYL) can be used when the site of attachment is a primary amino group; and 4-dimethylaminophenylazophenyl-4'-maleimide (DABMI) can be used when the site of attachment is a sulphydryl group. Similarly, fluorescein can be introduced in the oligonucleotides, either using a fluorescein phosphoramadite that replaces a nucleoside with fluorescein, or by using a fluorescein dT phosphoramadite that introduces a fluorescein moiety at a thymidine ring via a linker. To link a fluorescein moiety to a terminal location, iodoacetoamidofluorescein can be coupled to a sulphydryl group. Tetrachlorofluorescein (TET) can be introduced during automated synthesis using a 5'-tetrachloro-fluorescein phosphoramadite. Other reactive fluorophore derivatives and their respective sites of attachment include the succinimidyl ester of 5-carboxyrhodamine-6G (RHD) coupled to an amino group; an iodoacetamide of tetramethylrhodamine coupled to a sulphydryl group; an isothiocyanate of tetramethylrhodamine coupled to an amino group; or a sulfonylchloride of Texas red coupled to a sulphydryl group. During the synthesis of these labeled components, conjugated oligonucleotides or PNAs can be purified, if desired, e.g., by high pressure liquid chromatography or other methods.

A variety of commercial suppliers produce standard and custom molecular beacons, including Cruachem (cruachem.com), Oswel Research Products Ltd. (UK; oswel.com), Research Genetics (a division of Invitrogen, Huntsville Ala. (resgen.com)), the Midland Certified Reagent Company (Midland, Tex. mcrc.com) and Gorilla Genomics, LLC (Alameda, Calif.). A variety of kits, which utilize molecular beacons are also commercially available, such as the Sentinel™ Molecular Beacon Allelic Discrimination Kits from Stratagene (La Jolla, Calif.) and various kits from Eurogentec SA (Belgium, eurogentec.com) and Isogen Bioscience BV (The Netherlands, isogen.com).

In certain embodiments, a real time PCR assay system that includes one or more 5'-nuclease probes is used for detecting amplified *N. gonorrhoeae* and/or *C. trachomatis* nucleic acids. These systems operate by using the endogenous nuclease activity of certain polymerases to cleave a quencher or label free from an oligonucleotide of the invention that comprises the quencher and label, resulting in unquenching of the label. The polymerase only cleaves the quencher or label upon initiation of replication, i.e., when the oligonucleotide is bound to the template and the polymerase extends the primer. Thus, an appropriately labeled oligonucleotide probe and polymerase comprising the appropriate nuclease activity can be used to detect an *N. gonorrhoeae* and/or *C. trachomatis* nucleic acid of interest. Real time PCR product analysis by, e.g., FRET or the like (and related real time reverse-transcription PCR) provides a well-known technique for real time PCR monitoring that has been used in a variety of contexts, which can be adapted for use with the probes and methods described herein (see, Laurendeau et al. (1999) "TaqMan PCR-based gene dosage assay for predictive testing in individuals from a cancer family with INK4 locus haploinsufficiency" *Clin Chem* 45(7):982-6; Laurendeau et al. (1999) "Quantitation of MYC gene expression in sporadic breast tumors with a real-time reverse transcription-PCR assay" *Clin Chem* 59(12): 2759-65; and Kreuzer et al. (1999) "LightCycler technology for the quantitation of bcr/abl fusion transcripts" *Cancer Research* 59(13):3171-4, all of which are incorporated by reference).

X. Systems

The invention also provides a system for detecting *N. gonorrhoeae* and/or *C. trachomatis* in a sample. The system includes one or more nucleic acid detection reagents as described herein (e.g., probe nucleic acids, sequence specific antibodies, etc.). In certain embodiments, the nucleic acid detection reagents are arrayed on a solid support, whereas in others, they are provided in one or more containers, e.g., for assays performed in solution. The system also includes at least one detector (e.g., a spectrometer, etc.) that detects binding between nucleic acids and/or amplicons thereof from the sample and the nucleic acid detection reagent. Other detectors are described further below. In addition, the system also includes at least one controller operably connected to the detector. The controller includes one or more instructions sets that correlate the binding detected by the detector with a presence of *Neisseria gonorrhoeae* and/or *C. trachomatis* in the sample.

In some embodiments, at least one container the nucleic acid detection reagent. In these embodiments, the system optionally further includes at least one thermal modulator operably connected to the container to modulate temperature in the container, and/or at least one fluid transfer component (e.g., an automated pipettor, etc.) that transfers fluid to and/or from the container, e.g., for performing one or more nucleic acid amplification techniques in the container, etc.

Exemplary commercially available systems that are optionally utilized to detect *N. gonorrhoeae* and/or *C. trachomatis* nucleic acids using the nucleic acid detection reagents described herein (e.g., oligonucleotide probes comprising sequences selected from the group consisting of: SEQ ID NOS: 3-27 and 37-60 or complements thereto, sequence specific antibodies, etc.) include, e.g., a COBAS AMPLICOR® Analyzer, which is available from Roche Diagnostics Corporation (Indianapolis, Ind.), a LUMINEX 100™ system, which is available from the Luminex Corporation (Austin, Tex.), an ABI PRISM® Sequence Detection System, which is available from Applied Biosystems (Foster City, Calif.), and the like.

The invention further provides a computer or computer readable medium that includes a data set that comprises a plurality of character strings that correspond to a plurality of sequences that correspond to subsequences of SEQ ID NO: 1, SEQ ID NO: 2, SEQ ID NO: 36, a substantially identical variant thereof in which the variant has at least 90% sequence identity to one of SEQ ID NOS: 1 or 2 or 36, or a complement of SEQ ID NO: 1, SEQ ID NO: 2, SEQ ID NO: 36, or the variant. Typically, at least one of the character strings corresponds to a sequence selected from the group consisting of: SEQ ID NOS: 3-27, 37-60, and 68-70, or complements thereof. Typically, the computer or computer readable medium further includes an automatic synthesizer coupled to an output of the computer or computer readable medium. The automatic synthesizer accepts instructions from the computer or computer readable medium, which instructions direct synthesis of, e.g., one or more probe nucleic acids that correspond to one or more character strings in the data set. Exemplary systems and system components are described further below.

Detectors are structured to detect detectable signals produced, e.g., in or proximal to another component of the system (e.g., in container, on a solid support, etc.). Suitable signal detectors that are optionally utilized, or adapted for use, in these systems detect, e.g., fluorescence, phosphorescence, radioactivity, absorbance, refractive index, luminescence, or the like. Detectors optionally monitor one or a plurality of signals from upstream and/or downstream of the performance of, e.g., a given assay step. For example, the detector optionally monitors a plurality of optical signals, which correspond in position to "real time" results. Example detectors or sensors include photomultiplier tubes, CCD arrays, optical sensors, temperature sensors, pressure sensors, pH sensors, conductivity sensors, scanning detectors, or the like. Each of these as well as other types of sensors is optionally readily incorporated into the systems described herein. Optionally, the systems of the present invention include multiple detectors.

More specific exemplary detectors that are optionally utilized in these systems include, e.g., a resonance light scattering detector, an emission spectroscope, a fluorescence spectroscope, a phosphorescence spectroscope, a luminescence spectroscope, a spectrophotometer, a photometer, and the like. Various synthetic components are also utilized, or adapted for, use in the systems of the invention including, e.g., automated nucleic acid synthesizers, e.g., for synthesizing the oligonucleotides probes described herein. Detectors and synthetic components that are optionally included in the systems of the invention are described further in, e.g., Skoog et al., *Principles of Instrumental Analysis,* 5$^{th}$ Ed., Harcourt Brace College Publishers (1998) and Currell, *Analytical Instrumentation: Performance Characteristics and Quality,* John Wiley & Sons, Inc. (2000), both of which are incorporated by reference.

The systems of the invention also typically include controllers that are operably connected to one or more components (e.g., detectors, synthetic components, thermal modulator, fluid transfer components, etc.) of the system to control operation of the components. More specifically, controllers are generally included either as separate or integral system components that are utilized, e.g., to receive data from detectors, to effect and/or regulate temperature in the containers, to effect and/or regulate fluid flow to or from selected containers, or the like. Controllers and/or other system components is/are optionally coupled to an appropriately. programmed processor, computer, digital device, or other information appliance (e.g., including an analog to digital or digital to analog converter as needed), which functions to instruct the operation of these instruments in accordance with preprogrammed or user input instructions, receive data and information from these instruments, and interpret, manipulate and report this information to the user. Suitable controllers are generally known in the art and are available from various commercial sources.

Any controller or computer optionally includes a monitor, which is often a cathode ray tube ("CRT") display, a flat panel display (e.g., active matrix liquid crystal display, liquid crystal display, etc.), or others. Computer circuitry is often placed in a box, which includes numerous integrated circuit chips, such as a microprocessor, memory, interface circuits, and others. The box also optionally includes a hard disk drive, a floppy disk drive, a high capacity removable drive such as a writeable CD-ROM, and other common peripheral elements. Inputting devices such as a keyboard or mouse optionally provide for input from a user. These components are illustrated further below.

The computer typically includes appropriate software for receiving user instructions, either in the form of user input into a set of parameter fields, e.g., in a GUI, or in the form of preprogrammed instructions, e.g., preprogrammed for a variety of different specific operations. The software then converts these instructions to appropriate language for instructing the operation of one or more controllers to carry out the desired operation. The computer then receives the data from, e.g., sensors/detectors included within the system, and interprets the data, either provides it in a user understood format, or uses that data to initiate further controller instructions, in accordance with the programming, e.g., such as controlling fluid flow regulators in response to fluid weight data received from weight scales or the like.

The computer can be, e.g., a PC (Intel x86 or Pentium chip-compatible DOS™, OS2™, WINDOWS™, WINDOWS NT™, WINDOWS95™, WINDOWS98™, WINDOWS2000™, WINDOWS XP™, LINUX-based machine, a MACINTOSH™, Power PC, or a UNIX-based (e.g., SUN™ work station) machine) or other common commercially available computer which is known to one of skill. Standard desktop applications such as word processing software (e.g., Microsoft Word™ or Corel WordPerfect™) and database software (e.g., spreadsheet software such as Microsoft Excel™, Corel Quattro Pro™, or database programs such as Microsoft Access™ or Paradox™) can be adapted to the present invention. Software for performing, e.g., controlling temperature modulators and fluid flow regulators is optionally constructed by one of skill using a standard programming language such as Visual basic, Fortran, Basic, Java, or the like.

Figure 2:
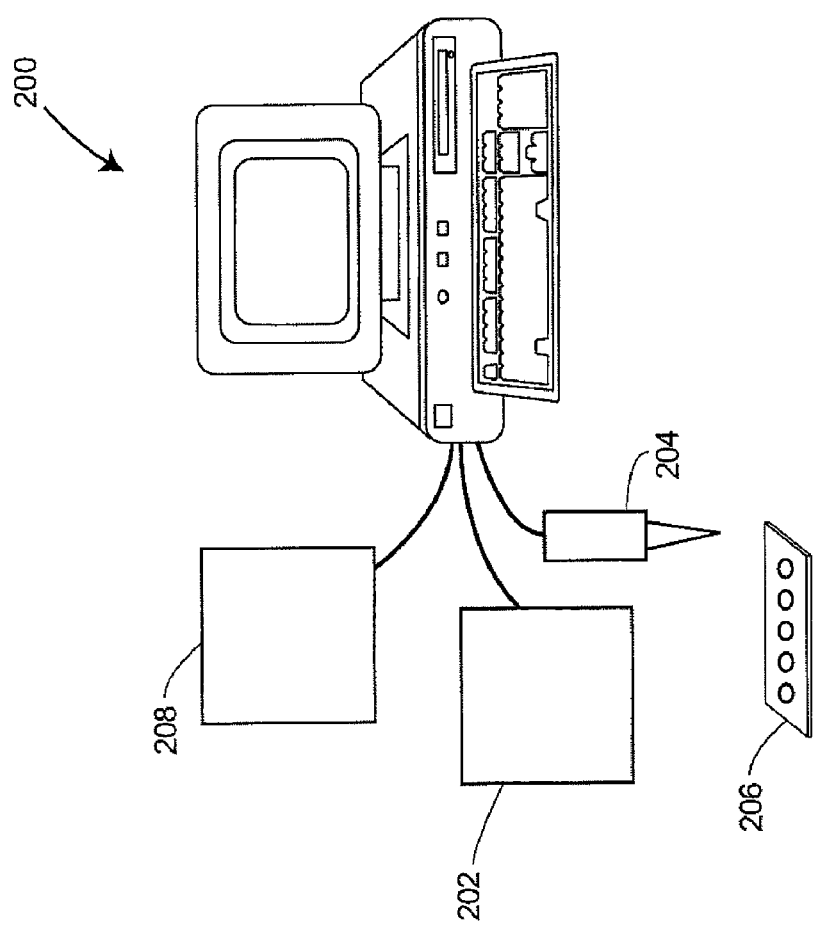
FIG. 2 is a block diagram showing a representative example system for detecting *N. gonorrhoeae* in a sample.
Figure 3:
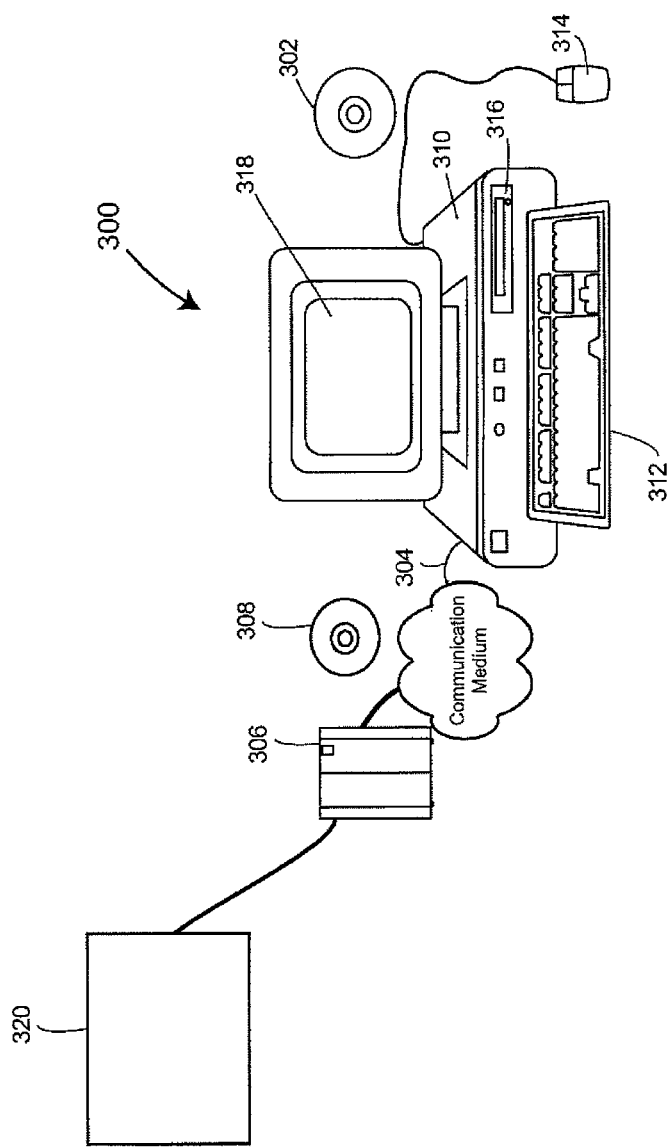
FIG. 3 is a block diagram showing a representative example system including a computer and a computer readable medium in which various aspects of the present invention may be embodied.

FIGS. 2 and 3 are schematics showing representative example systems that include logic devices in which various aspects of the present invention may be embodied. As will be understood by practitioners in the art from the teachings provided herein, the invention is optionally implemented in hardware and/or software. In some embodiments, different aspects of the invention are implemented in either client-side logic or server-side logic. As will be understood in the art, the invention or components thereof may be embodied in a media program component (e.g., a fixed media component) containing logic instructions and/or data that, when loaded into an appropriately configured computing device, cause that device to perform according to the invention. As will also be understood in the art, a fixed media containing logic instructions may be delivered to a viewer on a fixed media for physically loading into a viewer's computer or a fixed media containing logic instructions may reside on a remote server that a viewer accesses through a communication medium in order to download a program component.

In particular, FIG. 2 schematically illustrate computer 200 to which detector 202 and fluid transfer component 204 are operably connected. Optionally, detector 202 and/or fluid transfer component 204 is operably connected to computer 200 via a server (not shown in FIG. 2). During operation, fluid transfer component 204 typically transfers fluids, such as sample aliquots comprising labeled *N. gonorrhoeae* and/or *C. trachomatis* amplicons to nucleic acid detection reagent array 206, e.g., comprising oligonucleotide probes, sequence specific antibodies, etc., as described herein, arrayed thereon. Thereafter, detector 202 typically detects detectable signals (e.g., fluorescent emissions, etc.) produced by labeled amplicons that hybridize with probes attached to nucleic acid detection reagent array 206 after one or more washing steps are performed to wash away non-hybridized nucleic acids from nucleic acid detection reagent array 206 using fluid transfer component 204. As additionally shown, thermal modulator 208 is also operably connected to computer 200. Prior to performing a hybridization assay, target *N. gonorrhoeae* and/or *C. trachomatis* nucleic acids can be amplified using labeled primer nucleic acids (e.g., primers comprising sequences selected from SEQ ID NOS: 3-27 and 37-60). The amplicons of these amplification reactions are then typically transferred to nucleic acid detection reagent array 206 using fluid transfer component 204, as described above, to perform the binding assay. In some embodiments, binding assays are performed concurrently with *N. gonorrhoeae* and/or *C. trachomatis* nucleic acid amplification in thermal modulator 208 using, e.g., molecular beacons, 5'-nuclease probes, or the like that comprise sequences selected from SEQ ID NOS: 3-27 and 37-60. In these embodiments, detector 202 detects detectable signals produced as the amplification reactions are performed using thermal modulator 208.

FIG. 3 schematically shows information appliance or digital device 300 that may be understood as a logical apparatus that can read instructions from media 302 and/or network port 304, which can optionally be connected to server 306 having fixed media 308. Digital device 300 can thereafter use those instructions to direct server or client logic, as understood in the art, to embody aspects of the invention. One type of logical apparatus that may embody the invention is a computer system as illustrated in 300, containing CPU 310, optional input devices 312 and 314, disk drives 316 and optional monitor 318. Fixed media 302, or fixed media 308 over port 304, may be used to program such a system and may represent a disk-type optical or magnetic media, magnetic tape, solid state dynamic or static memory, or the like. In specific embodiments, the invention may be embodied in whole or in part as software recorded on this fixed media. Communication port 304 may also be used to initially receive instructions that are used to program such a system and may represent any type of communication connection. Optionally, the invention is embodied in whole or in part within the circuitry of an application specific integrated circuit (ACIS) or a programmable logic device (PLD). In such a case, the invention may be embodied in a computer understandable descriptor language, which may be used to create an ASIC, or PLD.

FIG. 3 also includes automatic synthesizer 320, which is operably connected to digital device 300 via server 306. Optionally, automatic synthesizer 320 is directly connected to digital device 300. During operation, automatic synthesizer 320 typically receives instructions to synthesize one or more primers or probes that comprise a sequence selected from the group consisting of: SEQ ID NOS: 3-27, 37-60, and 68-70, or complements thereto, which are included in a data set comprised by, e.g., digital device 300 and/or a computer readable medium, such as fixed media 302 and/or 308.

XI. Kits

The nucleic acid detection reagents employed in the methods of the present invention are optionally packaged into kits. As described herein, the nucleic acid detection reagents of the invention detectably bind to a nucleic acid with a sequence consisting of SEQ ID NO: 1, SEQ ID NO: 2, SEQ ID NO: 36, a substantially identical variant thereof in which the variant has at least 90% sequence identity to one of SEQ ID NOS: 1 or 2 or 36, or a complement of SEQ ID NO: 1, SEQ ID NO: 2, SEQ ID NO: 36, or the variant. In addition, the kits may also include suitably packaged reagents and materials needed for DNA immobilization, hybridization, and/or detection, such solid supports, buffers, enzymes, and DNA standards, as well as instructions for conducting the assay. Optionally, the nucleic acid detection reagents (e.g., oligonucleotide probes, sequence specific antibodies, etc.) of the invention are provided already attached or otherwise immobilized on solid supports. As another option, nucleic acid detection reagents are provided free in solution in containers, e.g., for performing the detection methods of the invention in the solution phase. In some of these embodiments, nucleic acid detection reagents of the kits comprise labels and/or quencher moieties, such as when molecular beacons, 5'-nuclease probes, or the like comprise sequences selected from SEQ ID NOS: 3-27, 37-60, and 68-70. In certain embodiments, kits further include labeled primers for amplifying target *N. gonorrhoeae* and/or *C. trachomatis* sequences in a sample.

The kit also includes one or more of: a set of instructions for contacting the nucleic acid detection reagents with nucleic acids from a sample or amplicons thereof and detecting binding between the nucleic acid detection reagents and *N. gonorrhoeae* and/or *C. trachomatis* nucleic acids, if any, or at least one container for packaging the nucleic acid detection reagents and the set of instructions. Exemplary solid supports include in the kits of the invention are optionally selected from, e.g., a plate, a microwell plate, a bead, a microbead, a tube (e.g., a microtube, etc.), a fiber, a whisker, a comb, a hybridization chip, a membrane, a single crystal, a ceramic layer, a self-assembling monolayer, or the like.

In some embodiments, the kit further includes at least one primer nucleic acid that is at least partially complementary to at least one segment of an *N. gonorrhoeae* nucleic acid, e.g., for amplifying a segment of the *N. gonorrhoeae* nucleic acid. In certain embodiments, the kit also includes one or more primers for amplifying one or more segments of a *C. trachomatis* nucleic acid. In these embodiments, the kit typically further includes a set of instructions for amplifying one or more subsequences of those nucleic acids with the primer nucleic acids, at least one nucleotide incorporating biocatalyst, and one or more nucleotides. In certain embodiments, the primer nucleic acids comprise at least one label (e.g., a fluorescent dye, a radioisotope, etc.). Suitable labels are described further herein. For example, the primer nucleic acid is optionally conjugated with biotin or a biotin derivative. In these embodiments, the kit typically further includes an enzyme conjugated with avidin or an avidin derivative, or streptavidin or a streptavidin derivative, e.g., for effecting the detection of binding between the nucleic acid detection reagents of the invention and target nucleic acids. In these embodiments, the kit generally further includes at least one nucleotide incorporating biocatalyst (e.g., a polymerase, a ligase, or the like). In these embodiments, the kit typically also further comprising one or more nucleotides, e.g., for use in amplifying the target nucleic acids. Optionally, at least one of the nucleotides comprises a label. In some of these embodiments, the kits further include at least one pyrophosphatase (e.g., a thermostable pyrophosphatase), e.g., for use in minimizing pyrophosphorolysis, uracil N-glycosylase (UNG) (e.g., a thermostable UNG), e.g., for use in applications where protection against carry-over contamination is desirable.

XII. EXAMPLES

It is understood that the examples and embodiments described herein are for illustrative purposes only and are not intended to limit the scope of the claimed invention. It is also understood that various modifications or changes in light of the examples and embodiments described herein will be suggested to persons skilled in the art and are to be included within the spirit and purview of this application and scope of the appended claims.

Example I

Detection of *N. gonorrhoeae* Via *Neisseria gonorrhoeae* Direct Repeat 9

Selection and Synthesis of *Neisseria gonorrhoeae* Direct Repeat 9 Specific Oligonucleotide Primers for PCR Analysis The *Neisseria gonorrhoeae* Direct Repeat 9 (NGDR9) previously was identified as a two-copy DNA sequence in the *Neisseria gonorrhoeae* genome. The sequence of NGDR9 was obtained from the Los Alamos National Laboratory Sexually Transmitted Diseases database via the world wide web at stdgen.lanl.gov/stdgen/bacteria/ngon/. The entire 806 base pair NGDR9 sequence lacks substantial identity with any sequence in the *Neisseria meningitidis* genome, but has 36.85% identity with gaps (44.4% identity without gaps) to *Brucella suis* 1330 chromosome I section 155 (GenBank® accession number AE014469). FIG. 4 depicts a Clustal W alignment of the NGDR9 sequence (SEQ ID NO:1) with a portion of this *Brucella* sequence (SEQ ID NO:34). The NGDR9 sequence was scanned for regions of minimal sequence identity with *B. suis* and upstream and downstream oligonucleotide primers (NG519 (5'-CTCTCAATGC-CCAATCATAAAGC-3' (SEQ ID NO:5)) and a complement to NG514 (i.e., 5'-GATAAAGCAGACGAAGCGGATAC-3' (SEQ ID NO: 24)), respectively spanning a 190 base pair region of NGDR9 were synthesized. The deoxycytidylate units at the 3' ends of both of these primers had been modified to include t-butyl benzyl groups as described in, e.g., U.S. Pat. No. 6,001,611, entitled "MODIFIED NUCLEIC ACID AMPLIFICATION PRIMERS," issued Dec. 14, 1999 to Will, which is incorporated by reference. The positions of NG519 and NG514 in NGDR9 are underlined in FIG. 4.

The positions of other exemplary upstream and downstream oligonucleotide primer pairs are also underlined in FIG. 4. In particular, DK101 (5'-GTTTGGCGGCAAG-CATCT-3' (SEQ ID NO:7)) and DK102 (5'-AAATGGGAT-GCTGTCGTCAA-3' (SEQ ID NO:8)) are shown. The primer pair DK101 and a complement to DK102 (i.e., 5'-TTGAC-GACAGCATCCCATTT-3' (SEQ ID NO: 25)) is designed to amplify a 416 base pair region of NGDR9. Primers corresponding to DK101 and the complement to DK102, which further included 5'-end restriction site linkers were also synthesized, namely, HINDDK101 (5'-GGC AAGCTTGTTTGGCGGCAAGCATCT-3' (SEQ ID NO:9); HindIII restriction site underlined) and BAMDK102 (5'-GGCGGATCCTTGACGACAGCATCCCATTT-3' (SEQ ID NO:10); BamHI restriction site underlined). A photograph of an agarose gel that shows the detection of *N. gonorrhoeae* using this pair of primers is provided below. DK103 (5'-AAACGCAATCTTCAAACACCTCA-3' (SEQ ID NO:11)) and DK104 (5'-TTTGACGGCCTCACGCATAA-3' (SEQ ID NO:12)) are also shown underlined in FIG. 4. The primer pair DK103 and a complement to DK104 (i.e., 5'-TTATGCGT-GAGGCCGTCAAA-3' (SEQ ID NO: 26)) is designed to amplify a 384 base pair region of NGDR9.

Neisserial Genomic DNA Purification

Extraction of genomic DNA from various neisserial strains was performed by using the PureGene® DNA Purification system (Gentra Systems, Minneapolis Minn.). Bacterial cells were grown for 48 hours on Chocolate agar (Hardy Diagnostics, Santa Maria, Calif.) at 37° C. in 5% $CO_2$. The cells were scraped from the agar surface, re-suspended in PBS and centrifuged at 13,000-16,000×g for 5 seconds to pellet the cells. The supernatant was removed by aspiration, leaving behind 10-20 μl residual liquid. The samples were vortexed vigorously to re-suspend the pellet in the residual liquid. DNA extraction was carried out as instructed by the manufacturers. Briefly, 300 μl cell lysis solution was added to the re-suspended cells and pipetted up and down to lyse the cells. Following addition of 1.5 μl of RNAse A solution to the cell lysate, the samples were mixed by inverting the tubes 25 times and incubated for 5 minutes at 37° C. The samples were cooled to room temperature by being placed on ice for 1 minute. A 100 μl volume of Protein Precipitation Solution was added to the RNAse-treated cell lysate and the samples were mixed by vortexing vigorously at high speed for 20 seconds. The protein debris was precipitated by centrifugation at 13,000-16,000×g for 1 minute. The supernate containing the DNA samples was transferred into clean 1.5 ml micro centrifuge tubes, each containing 300 μl of 100% isopropanol. The samples were mixed by gently inverting the tubes 50 times and were then centrifuged at 13,000-16,000×g for 1 minute. The supernate was poured off and the pellet washed with 300 μl 70% ethanol. The tubes were centrifuged again at 13,000-16,000×g for 1 minute. After removal of the supernate, the tubes were drained by inversion and the DNA pellets were re-suspended in 50 μl of Hydration Solution. Genomic DNA was quantitated using the PicoGreen dsDNA Quantitation Reagents (Molecular Probes, Eugene, Oreg.) and the re-suspended DNA was stored at −20° C. until used.

Amplification of Segments of NGDR9

Separate PCR reactions were performed using genomic DNA isolated from the various neisserial species as templates and the pair of primers, NG519 and the complement to NG514 (described above). PCRs were performed in volumes of 100 μl containing 50 mM Tricine (pH 8.3), 80 mM $K(OAc)_2$ (pH 7.5), 2 mM $Mn(OAc)_2$ (pH 6.5), 50 μM dATP, 50 dGTP, 50 μM dCTP, 100 μM dUTP, 20 U of ZO5 DNA polymerase (Roche Molecular Systems, Alameda, Calif.), 5U AmpErase® UNG (Uracil-N-Glycosylase), 0.5 μM of each primer and 1 ng/μl ethidium bromide. Genomic DNA was added as template at $10^3$ genomic equivalents per reaction for *Neisseria gonorrhoeae* and $10^6$ genomic equivalents per reaction for *Neisseria meningitidis* and other neisserial strains. Reactions were performed for 60 cycles of denaturation at 95° C. for 15 seconds, annealing at 58° C. for 20 seconds, and a final extension at 72° C. for 5 minutes using a COBAS TaqMan® PCR System (Roche Molecular Systems, Alameda, Calif.).

Separate PCR reactions were also performed using genomic DNA isolated from various neisserial species as templates and the pair of primers, HINDDK101 and BAMDK102 (described above), using a procedure similar to that described above used to amplify the 190 base pair segment of NGDR9.

Analytical Agarose Gel Electrophoresis of PCR Products

The PCR products were prepared for gel electrophoresis analysis by adding 20 μl of the DNA samples to 8 μl of 10× gel loading buffer (0.025% bromophenol blue dye, 100 mM EDTA, and 30% sucrose). The samples were then loaded into lanes of a horizontally submerged gel containing a 3.0% (w/v) Nusieve, 0.5% (w/v) agarose gel and 0.5 μg/ml ethidium bromide in 1×TB buffer (0.089M Tris, 0.09M Boric Acid, 2 mM EDTA, pH 8.0). The electrophoresis running buffer was 1×TB buffer containing 0.5 ethidium bromide. The gel was run at 95-100 V for 1 hour, then removed and visualized on a long wavelength UV transilluminator. The particular gels were examined for the presence or absence of PCR amplification products at the expected sizes of 190 or 416 bp.

Figure 5:
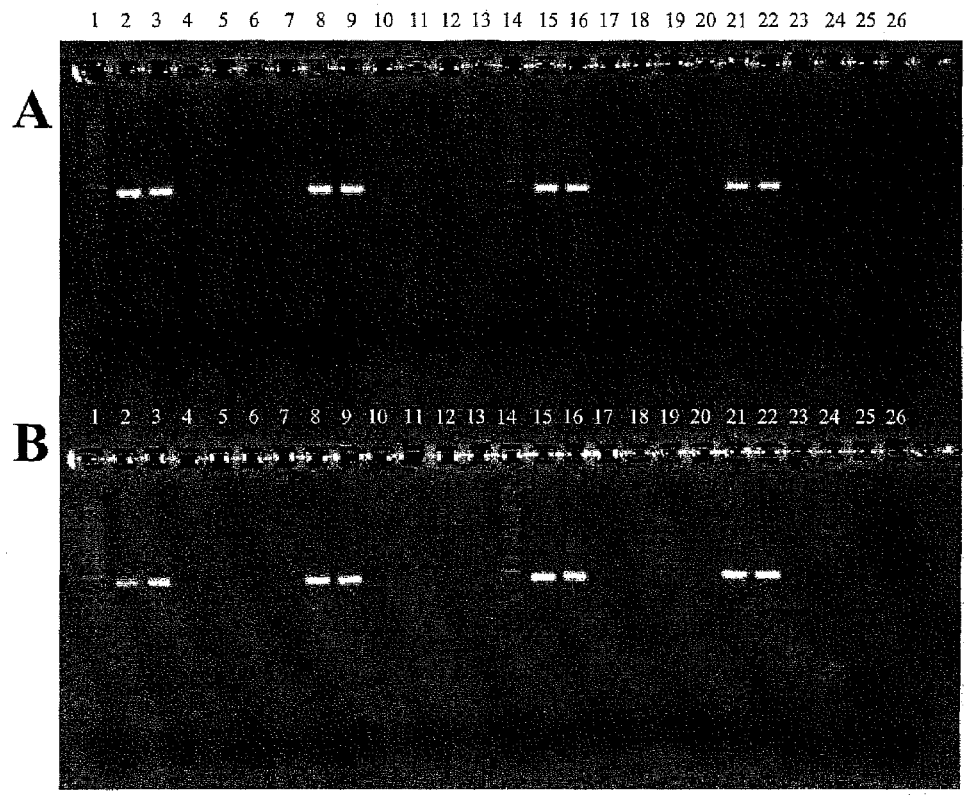
FIGS. 5A and B are photographs of agarose gels that show the detection of a 190 base pair segment of NGDR9.
Figure 6:
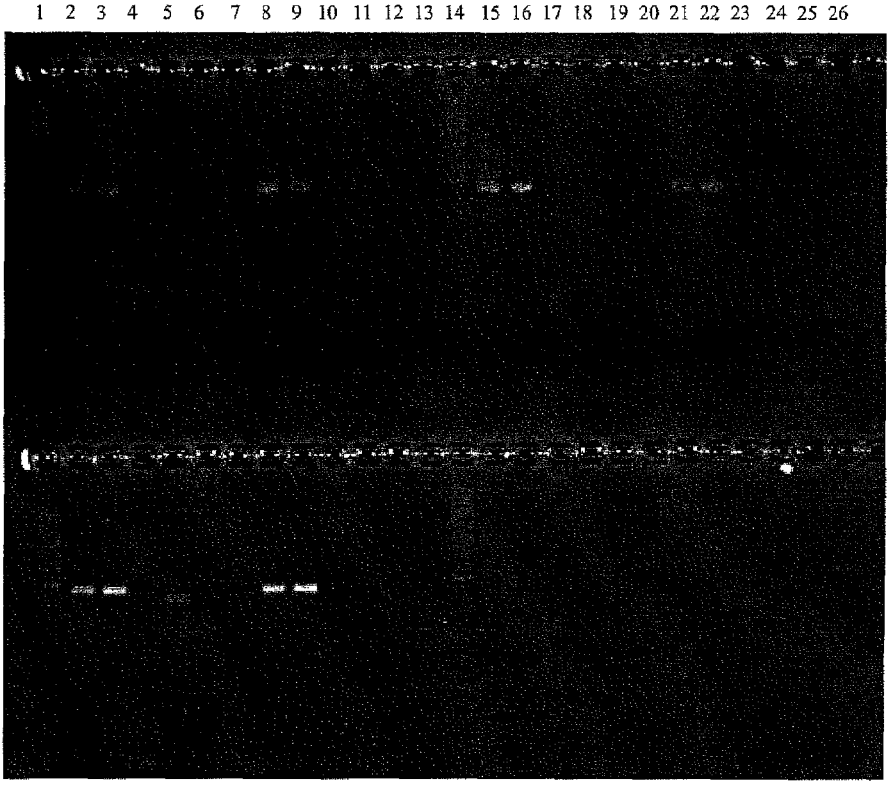
FIGS. 6A and B are photographs of agarose gels that show the detection of a 190 base pair segment of NGDR9.
Figure 7:
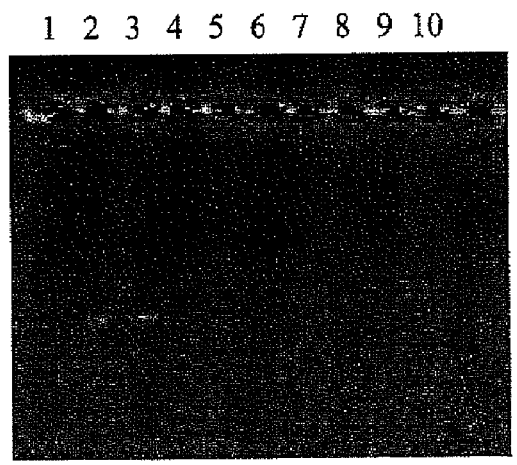
FIG. 7 is a photograph of an agarose gel that shows the detection of a 416 base pair segment of NGDR9.

FIGS. 5 A and B, and 6 A and B are photographs of agarose gels that show the detection of the 190 base pair segment of NGDR9, whereas FIG. 7 is a photograph of an agarose gel that shows the detection of the 416 base pair segment of NGDR9.

Example II

Assays Illustrating the Selective Detection of *N. gonorrhoeae*

This example provides lists of organisms that were analyzed in assays that included the use of primer nucleic acids NG519 (having a sequence corresponding to SEQ ID NO: 5) and NG514R (having a sequence corresponding to SEQ ID NO: 24) and a 5'-nuclease probe (having a sequence corresponding to SEQ ID NO: 18) alone or in combination with *C. trachomatis* primers. In particular, the inclusivity (i.e., a measure of the ability to detect the target organism, *N. gonorrhoeae* in samples) of these assays is illustrated in Table IX.

TABLE IX

| Genus | Species | Number | Primers | Results |
|---|---|---|---|---|
| *Neisseria* | *gonorrhoeae* | 108 | CT/NG | All Positive |

The exclusivity (i.e., a measure of the ability to exclude false positives when neisserial organisms of species other than *gonorrhoeae* are present in samples) of these assays is illustrated in Table X.

TABLE X

| Genus | Species | Number | Primers | Results |
|---|---|---|---|---|
| *Neisseria* | *animalis* | 3 | CT/NG | All Negative |
| *Neisseria* | *caviae* | 2 | " | " |
| *Neisseria* | *cinerea* | 6 | " | " |
| *Neisseria* | *cuniculi* | 1 | " | " |
| *Neisseria* | *denitrificans* | 2 | " | " |
| *Neisseria* | *elongata* | 4 | " | " |
| *Neisseria* | *flava* | 1 | " | " |
| *Neisseria* | *flavescens* | 7 | " | " |
| *Neisseria* | *kochi* | 1 | " | " |
| *Neisseria* | *lactamica* | 6 | " | " |
| *Neisseria* | *meningitidis* | 21 | " | " |
| *Neisseria* | *mucosa* | 14 | " | " |
| *Neisseria* | *perflava* | 6 | " | " |
| *Neisseria* | *polysaccharea* | 3 | " | " |
| *Neisseria* | *sicca* | 7 | " | " |
| *Neisseria* | *subflava* | 1 | " | " |

TABLE X-continued

| Genus | Species | Number | Primers | Results |
|---|---|---|---|---|
| *Neisseria* | *subflava biovar flava* | 1 | " | " |
| *Neisseria* | *subflava biovar perflava* | 2 | " | " |
| *Neisseria* | *subflava biovar subflava/flava* | 2 | " | " |
| *Neisseria* | *subflava perflava* | 5 | " | " |
| | Total | 95 | | All Negative |

The specificity (i.e., a measure of the ability to exclude false positives when non-neisserial organisms are present in samples) of these assays is illustrated in Table XI.

TABLE XI

| Genus | Species | Number | Primers | Results |
|---|---|---|---|---|
| *Chlamydia* | *trachomatis* | 15 | NG | All Negative |
| *Chlamydia* | *pneumonae* | 1 | " | " |
| *Chlamydia* | *psittaci* | 1 | " | " |
| *Achromobacter* | *xerosis* | 1 | " | " |
| *Acinetobacter* | *lwoffi* | 1 | " | " |
| *Acinetobacter* | *calcoaceticus* | 1 | " | " |
| *Acinetobacter* | sp. genospecies 3 | 1 | " | " |
| *Actinomyces* | *isrealii* | 1 | " | " |
| *Aerococcus* | *viridans* | 1 | " | " |
| *Aeromonas* | *hydrophila* | 1 | " | " |
| *Agrobacterium* | *radiobacter* | 1 | " | " |
| *Alcaligenes* | *faecalis* | 1 | " | " |
| *Bacillus* | *thuringiensis* | 1 | " | " |
| *Bacillus* | *subtilis* | 1 | " | " |
| *Bacteriodes* | *fragilis* | 1 | " | " |
| *Bacteroides* | *caccae* | 1 | " | " |
| *Bifidobacillus* | *longum* | 1 | " | " |
| *Bifidobacterium* | *adolescentis* | 1 | " | " |
| *Branhamella* | *catarrhalis* | 1 | " | " |
| *Brevibacterium* | *linens* | 1 | " | " |
| *Candida* | *albicans* | 1 | " | " |
| *Chromobacter* | *violaceum* | 1 | " | " |
| *Citrobacter* | *freundii* | 1 | " | " |
| *Clostridium* | *innocuum* | 1 | " | " |
| *Clostridium* | *perfringens* | 1 | " | " |
| *Corynebacterium* | *genitalium* | 1 | " | " |
| *Corynebacterium* | *xerosis* | 1 | " | " |
| *Cryptococcus* | *neoformans* | 1 | " | " |
| *Deinococcus* | *radiopugnans* | 1 | " | " |
| *Derxia* | *gummosa* | 1 | " | " |
| *Echerichia* | *coli* | 1 | " | " |
| *Eikenella* | *corrodens* | 1 | " | " |
| *Enterobacter* | *cloacae* | 1 | " | " |
| *Enterococcus* | *avium* | 1 | " | " |
| *Enterococcus* | *faecalis* | 1 | " | " |
| *Enterococcus* | *faecium* | 1 | " | " |
| *Erysipelothrix* | *rhusiopathiae* | 1 | " | " |
| *Ewingella* | *americana* | 1 | " | " |
| *Flavobacterium* | *meningosepticum* | 1 | " | " |
| *Gamella* | *haemolysans* | 1 | " | " |
| *Gamella* | *morbillorum* | 1 | " | " |
| *Gardnerella* | *vaginalis* | 1 | " | " |
| *Haemophilus* | *influenzae* | 1 | " | " |
| *Haemophilus* | *ducreyi* | 1 | " | " |
| *Kingella* | *kingae* | 1 | " | " |
| *Klebsiella* | *pneumoniae ss ozaenae* | 1 | " | " |
| *Lactobacillus* | *oris* | 1 | " | " |
| *Lactobacillus* | *vaginalis* | 1 | " | " |
| *Lactobacillus* | *acidophillus* | 1 | " | " |
| *Lactobacillus* | *brevis* | 1 | " | " |
| *Lactobacillus* | *crisptus* | 1 | " | " |
| *Lactobacillus* | *lactis lactis* | 1 | " | " |
| *Lactobacillus* | *parabuchnerri* | 1 | " | " |
| *Lactococcus* | *lactis cremoris* | 1 | " | " |
| *Legionella* | *bozemanii* | 1 | " | " |
| *Legionella* | *pneumophila* | 1 | " | " |
| *Leuconostoc* | *paramesenteroides* | 1 | " | " |
| *Micrococcus* | *luteus* | 1 | " | " |

TABLE XI-continued

| Genus | Species | Number | Primers | Results |
|---|---|---|---|---|
| Moraxella | osloensis | 1 | " | " |
| Morganella | morganii | 1 | " | " |
| Mycobacterium | smegmatis | 1 | " | " |
| Mycoplasma | hominis | 1 | " | " |
| Serratia | denitrificans | 1 | " | " |
| Pasteurella | maltocida | 1 | " | " |
| Pediococcus | acidilactica | 1 | " | " |
| Peptostreptococcus | magnus | 1 | " | " |
| Peptostreptococcus | productus | 1 | " | " |
| Prevotella | bivia | 1 | " | " |
| Prevotella | corporis | 1 | " | " |
| Prevotella | intermedia | 1 | " | " |
| Propionibacterium | acnes | 1 | " | " |
| Proteus | mirabilis | 1 | " | " |
| Providencia | stuartii | 1 | " | " |
| Pseudomonas | aeruginosa | 1 | " | " |
| Pseudomonas | putida | 1 | " | " |
| Rahnella | aquatilis | 1 | " | " |
| Salmonella | minnesota | 1 | " | " |
| Salmonella | typhimurium | 1 | " | " |
| Serratia | marscence | 1 | " | " |
| Staphylococcus | aureus | 1 | " | " |
| Staphylococcus | epidermidis | 1 | " | " |
| Streptococcus | salivarius | 1 | " | " |
| Streptococcus | agalactiae | 1 | " | " |
| Streptococcus | anginosus | 1 | " | " |
| Streptococcus | bovis | 1 | " | " |
| Streptococcus | dysgalatia | 1 | " | " |
| Streptococcus | equinis | 1 | " | " |
| Streptococcus | pneumoniae | 1 | " | " |
| Streptococcus | pyogenes | 1 | " | " |
| Vibrio | parahaemolyticus | 1 | " | " |
| Yersinia | enterocolitica | 1 | " | " |
| Treponema | pallidum | 1 | " | " |
| Herpes simplex virus 1 | | 1 | " | " |
| Herpes simplex virus 2 | | 1 | " | " |
| Epstein Barr Virus | | 1 | " | " |
| Human papilloma virus type 16 | | 1 | " | " |
| Human papilloma virus type 18 | | 1 | " | " |
| Total | | 111 | | All Negative |

Example III

Detection of *N. gonorrhoeae* Via *Neisseria gonorrhoeae* Direct Repeat 33

Selection and Synthesis of *Neisseria gonorrhoeae* Direct Repeat 33 Specific Oligonucleotide Primers for PCR Analysis The *Neisseria gonorrhoeae* Direct Repeat 33 (NGDR33) was previously identified as a two-copy DNA sequence in the *Neisseria gonorrhoeae* genome. The sequence of NGDR33 was obtained from the Los Alamos National Laboratory Sexually Transmitted Diseases database via the world wide web at stdgen.lanl.gov/stdgen/bacteria/ngon/. A blast homology search of NGDR33 revealed numerous significant hits with *Neisseria meningitidis* and the entire 1142 base pair NGDR33 sequence has 38.09% identity with gaps (50.44% identity without gaps) to *N. meningitidis* serogroup B strain MC58 section 77 (GenBank® accession number AE002435). FIG. 8 depicts a Clustal W alignment of the NGDR33 sequence (SEQ ID NO:2) with a portion of this *N. meningitidis* sequence (SEQ ID NO:35). The NGDR33 sequence was scanned for regions of minimal sequence identity with N meningitidis and upstream and downstream oligonucleotide primers (NG613 (5'-AATGTCGGGTTTGACGAAACTC-3' (SEQ ID NO:15)) and a complement to NG614 (i.e., 5'-AACGTCCGACAACCGGTAAC-3' (SEQ ID NO:27)), respectively spanning a 265 base pair region of NGDR33 were synthesized. The positions of NG613 and NG614 are underlined in FIG. 8. The deoxycytidylate units at the 3' ends of both of these primers had been modified, as referred to above, to include t-butyl benzyl groups.

Figure 9:
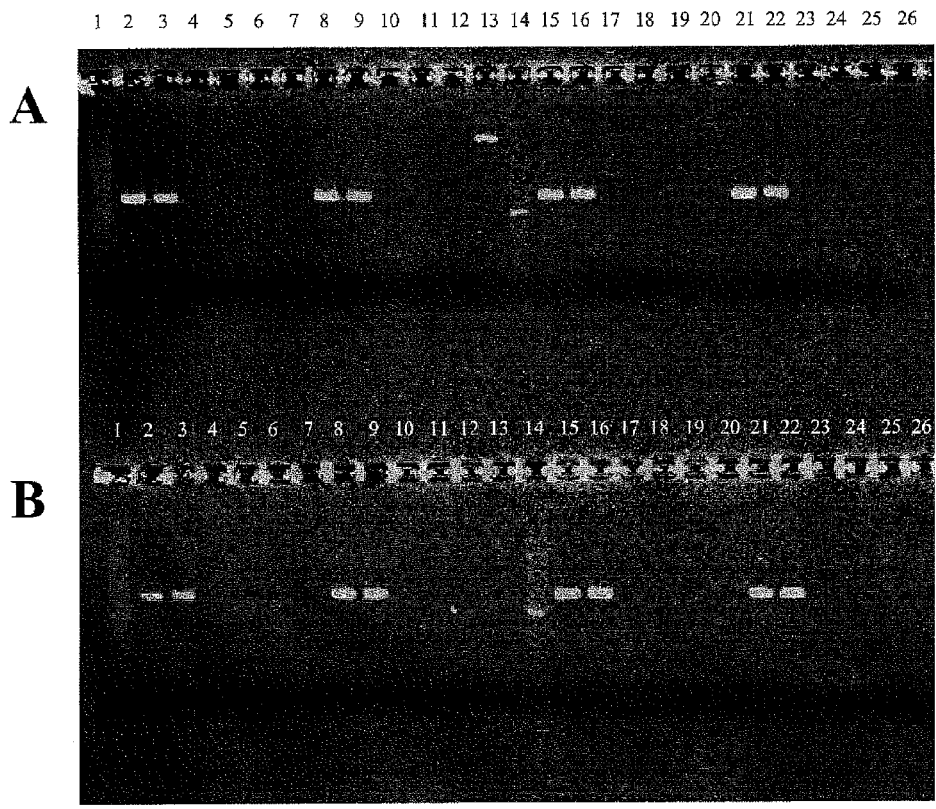
FIGS. 9A and B are photographs of agarose gels that show the detection of a 265 base pair segment of NGDR33.
Figure 10:
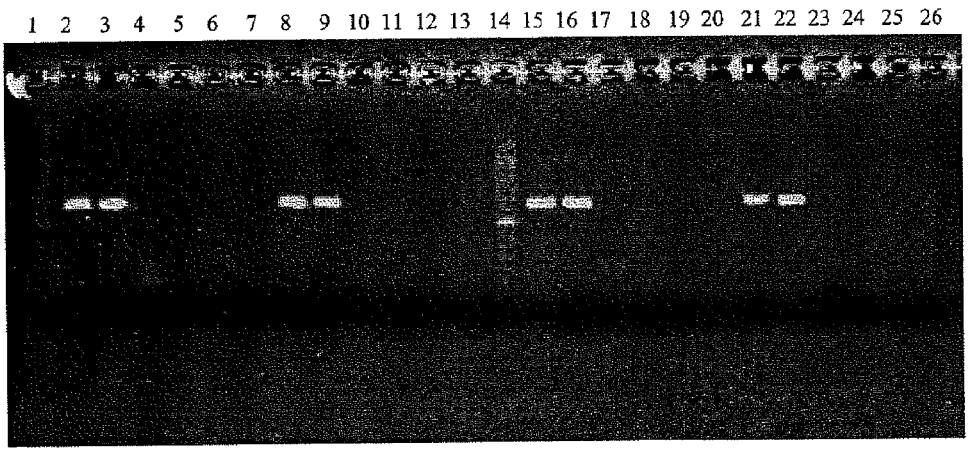
FIG. 10 is a photograph of an agarose gel that shows the detection of a 265 base pair segment of NGDR33.

Neisserial Genomic DNA Purification, Amplification, and Analytical Agarose Gel Electrophoresis The genomic DNA of various neisserial species was purified as described above in Example I. Separate PCR reactions were performed using genomic DNA isolated from various neisserial species as templates and the pair of primers, NG613 and the complement to NG614 (described above), using a procedure similar to that described above used to amplify the 190 base pair segment of NGDR9. In addition, the PCR products of these amplification reactions were electrophoretically separated as described above in Example I. The gels were examined for the presence or absence of PCR amplification products at the expected size of 265 bp. FIGS. 9 A and B, and 10 are photographs of agarose gels that show the detection of this 265 base pair segment of NGDR33

Example IV

Detection of *N. gonorrhoeae/C. trachomatis* in Clinical Samples

This prophetic example describes a protocol for the detection of *N. gonorrhoeae* and *C. trachomatis* in clinical samples.

Clinical Samples

Endocervical swab specimens from women and urethral swab specimens from men are collected by standard procedures known in the art. Swabs are inoculated into suitable culture transport media (e.g., 2SP, M-4 (Microtest, Inc., Atlanta, Ga.), Bartel's chlamydial (Intracel Corp., Issaquah, Wash.), etc.), which is then used for PCR analysis (see also, Van der Pol et al. (2000) *J. Clin. Microbiol.* 38:1105-1112, which is incorporated by reference). These specimens are generally stored at 2 to 8° C. and are typically transported to the laboratory within 24 to 72 hours of collection. The specimens are typically vortexed with the swab still in the tube, cell cultures are inoculated, and an aliquot of each specimen is transferred to a new tube, which is generally stored at 2 to 8° C. for up to 7 days postcollection and then processed for PCR analysis.

Optionally, 50 ml aliquots of first-catch urine is also collected from both men and women. Female urine specimens are collected either before or after swab collection. Male urine specimens are collected after the urethral swab specimens have been obtained. Urine specimens are typically stored at room temperature and transported to the laboratory within 24 hours or are stored at, e.g., 2 to 8° C. if not transported within 24 hours of collection. Upon arrival at the laboratory, a 500 µl aliquot is typically stored at 2 to 8° C. for up to 7 days from the time of collection until it is processed for PCR analysis.

PCR Analysis

Each specimen is typically processed and subjected to either or both the AMPLICOR® and COBAS AMPLICOR® tests as described in the manufacturer's package inserts. For each processed specimen, the *C. trachomatis, N. gonorrhoeae*, and internal control (IC) target DNAs are simultaneously amplified in a single reaction mixture that contains at least two primer pairs, at least one pair specific for *C. trachomatis* and at least one pair specific for *N. gonorrhoeae* (e.g., comprising at least one sequence selected from SEQ ID NOS: 3-27). The resulting amplification products are generally captured separately and detected colorimetrically by hybridization to microwell plates (AMPLICOR® format) (Crotchfelt et al. (1997) "Detection of *Neisseria gonorrhoeae* and *Chlamydia trachomatis* in genitourinary specimens from men and women by a coamplification PCR assay," *J. Clin. Microbiol.* 35:1536-1540, which is incorporated by reference) or to magnetic microparticles (COBAS AMPLICOR® format) coated with *N. gonorrhoeae*-(e.g., comprising sequences selected from SEQ ID NOS: 3-27), *C. trachomatis*-, and IC-specific oligonucleotide probes. The COBAS AMPLICOR® analyzer automatically performs all of the amplification, hybridization, and detection steps (DiDomenico et al. (1996) "COBAS AMPLICOR™: a fully automated RNA and DNA amplification and detection system for routine diagnostic PCR," *Clin. Chem.* 42:1915-1923, Jungkind et al. (1996) "Evaluation of automated COBAS AMPLI-COR PCR system for detection of several infectious agents and its impact on laboratory management," *J. Clin. Microbiol.* 34:2778-2783, which are both incorporated by reference). In the AMPLICOR® format, amplification is performed, e.g., with a GeneAmp® PCR System 9700 thermal cycler (Perkin-Elmer, Norwalk, Conn.) and hybridization and detection are performed manually (Loeffelholz et al. (1992) "Detection of *Chlamydia trachomatis* in endocervical specimens by polymerase chain reaction," *J. Clin. Microbiol.* 30:2847-2851, which is incorporated by reference).

Data Analysis

Specimens yielding signals above a positive cutoff (optical density [OD] of 2.0 ($A_{660}$) for *C. trachomatis* and OD of 3.5 ($A_{660}$) for *N. gonorrhoeae*) are typically interpreted as positive for the particular organism, regardless of the IC result. Specimens yielding *N. gonorrhoeae* or *C. trachomatis* signals below a negative cutoff (e.g., OD of 0.2) are typically interpreted as negative for the particular organism, provided that the IC signal is above the assigned cutoff (e.g., OD of 0.2) and the test considered valid. Specimens yielding *N. gonorrhoeae* or *C. trachomatis* signals below the cutoff values for both *N. gonorrhoeae* or *C. trachomatis* and IC are generally interpreted as inhibitory. Inhibitory specimens are typically retested by processing of a frozen aliquot of the original specimen. The repeat test results are classified using the above criteria.

Specimens yielding results between the negative and positive cutoffs ($\geq 0.2$, $<3.5$ for *N. gonorrhoeae* and $\geq 0.2$, $<2.0$ for *C. trachomatis*) are typically considered equivocal for the particular organism, regardless of the IC signal. Equivocal results are generally resolved by processing an aliquot of the original specimen, retesting in duplicate and comparing the results to the initial test. These specimens are typically interpreted as positive for the particular organism if at least two valid tests yield an *N. gonorrhoeae* or *C. trachomatis* OD of $\geq 2.0$ for the particular organism. These specimens are generally interpreted as negative for the particular organism if the two repeat tests yield *N. gonorrhoeae* or *C. trachomatis* signals of <0.2 OD for the particular organism, provided that the IC signals are above the assigned cutoff. If the two repeat tests yield an *N. gonorrhoeae* or *C. trachomatis* OD of <0.2 for the particular organism and the IC signal is below the assigned cutoff for either of the duplicate repeat tests, the specimen is generally interpreted as inhibitory.

Example V

Figures 2, 11:
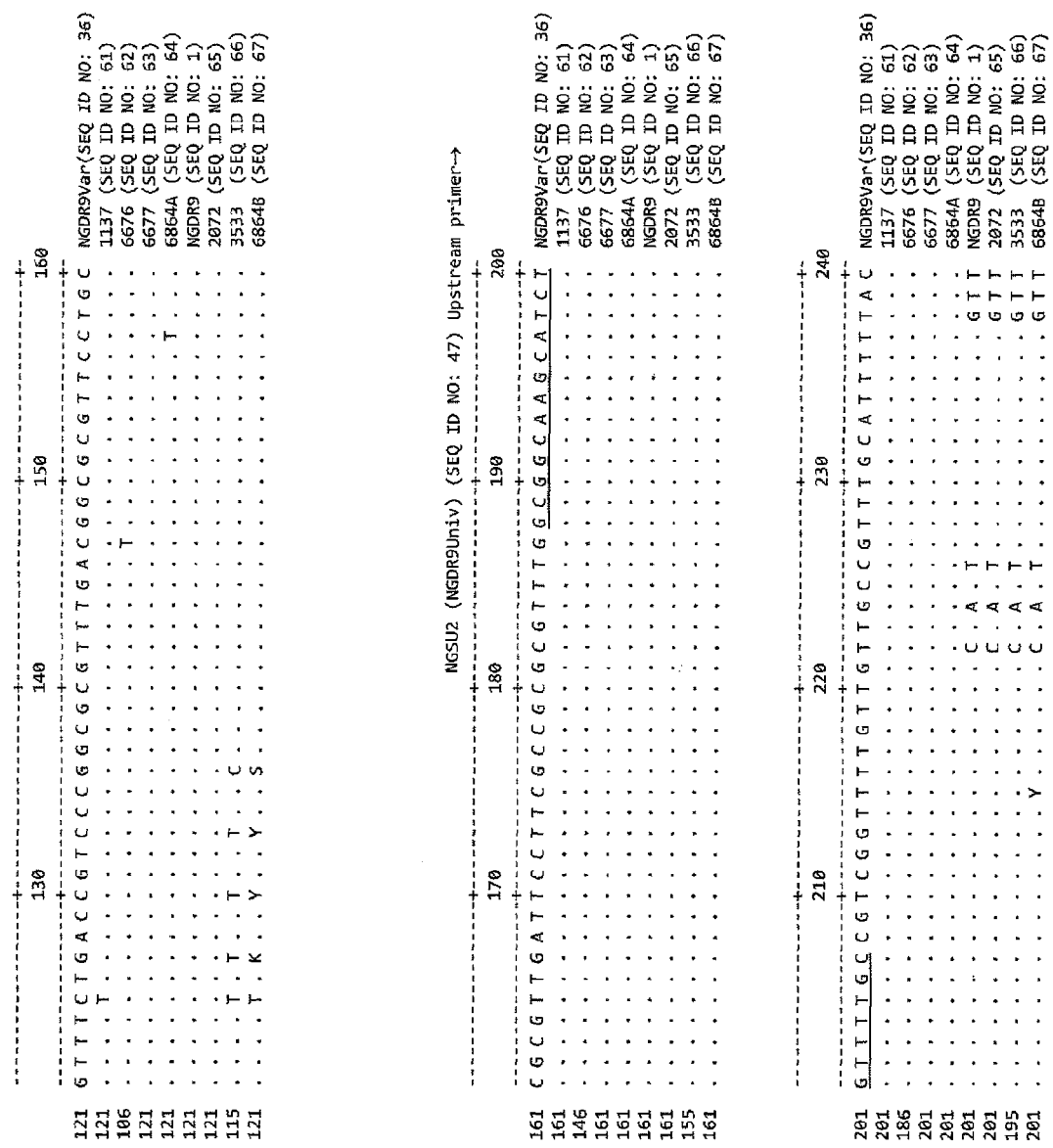
FIG. 11 shows a sequence alignment of a *Neisseria gonorrhoeae* Direct Repeat 9 Variant (NGDR9Var) sequence (SEQ ID NO: 36) with the sequences of amplicons of genomic DNA from various *N. gonorrhoeae* strains (strain 1137, SEQ ID NO: 61; strain 6676, SEQ ID NO: 62; strain 6677, SEQ ID NO: 63; strain 6864A, SEQ ID NO: 64; strain 2072, SEQ ID NO: 65; strain 3533, SEQ ID NO: 66; and strain 6864B, SEQ ID NO: 67) and the NGDR9 sequence (SEQ ID NO: 1).
Figures 3, 11:
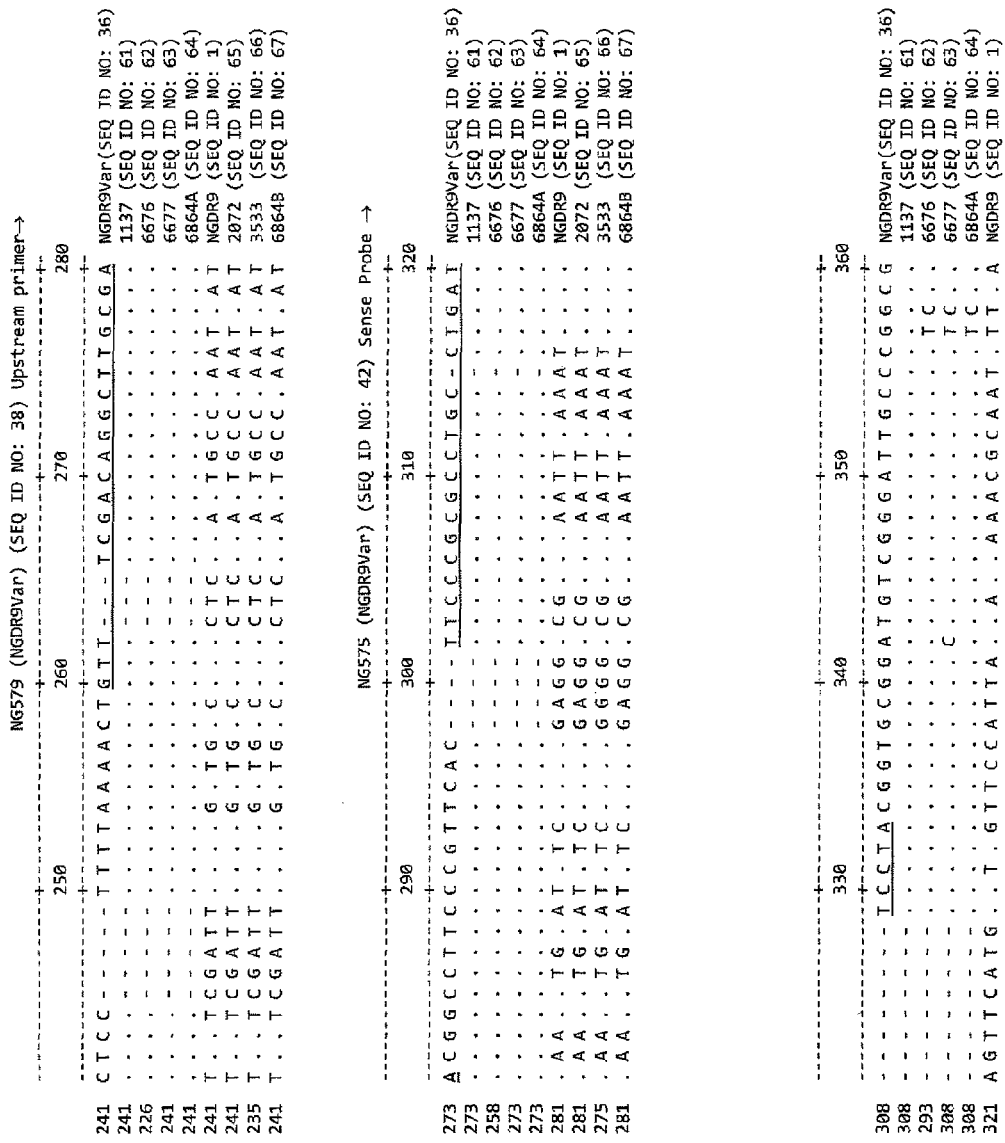

Detection of *N. gonorrhoeae* Via *Neisseria gonorrhoeae* Direct Repeat 9 Variant Selection and Synthesis of NGDR9Var Oligonucleotides for PCR Analysis As described in Example I, the *Neisseria gonorrhoeae* Direct Repeat 9 (NGDR9) previously was identified as a two-copy DNA sequence in the *Neisseria gonorrhoeae* genome. It was subsequently confirmed as a 3-copy DNA sequence. However, during inclusivity testing of a prototype NG assay with NGDR9 primers, 4 *N. gonorrhoeae* strains (including strain NG889) isolated from clinical samples, were not amplified. Subsequent sequence analysis of genomic DNA from strain NG889 revealed the presence of 3 identical copies of a variant sequence (NGDR9Var), with significant mismatches within the target region of NGDR9 that precluded amplification by the NG519 (SEQ ID NO: 5) and NG514 (SEQ ID NO: 24) primers. The entire 727 base pair NGDR9Var sequence (SEQ ID NO: 36) bears no identity with any sequence in the *Neisseria meningitidis* genome but has 70% overall identity with the NGDR9 sequence (SEQ ID NO: 1). The NGDR9Var sequence was scanned for maximum sequence identity with variant sequences from additional *N. gonorrhoeae* strains, and upstream and downstream oligonucleotide primers NG579 (5'-GTTTCGACAGGCTTGC-GAA-3') (SEQ ID NO: 38) and NG552 (5'-CCTGTTTGC-GACAAAGAGGA-3') (SEQ ID NO: 40) spanning a 215 bp region of NGDR9Var were synthesized. The deoxyadenosine base at the 3' ends of both of these primers had been modified to include t-benzyl groups as described in, e.g., U.S. Pat. No. 6,001,611, entitled "MODIFIED NUCLEIC ACID AMPLI-FICATION PRIMERS," issued Dec. 14, 1999 to Will, which is incorporated by reference. The positions of NG579 and NG552 in NGDR9Var are underlined in FIG. 11.

Amplification of 215 bp Segment of NGDR9Var

Separate PCR reactions were performed using genomic DNA isolated from the various neisserial species (as described in Example I) as templates and the pair of primers NG579 and NG552 (described above). PCRs were performed in volumes of 100 µl containing 50 mM Tricine(pH 8.3), 80 mM K(OAc)$_2$ (pH 7.5), 1 mM Mn(OAc)$_2$ (pH 6.5), 5% glycerol, 1 mM Mg(OAc)$_2$ (pH 6.5), 50 µM dATP, 50 µM dGTP, 50 µM dCTP, 100 µM dUTP, 20 U of ZO5® DNA polymerase (Roche Molecular Systems, Alameda, Calif.), 5U AmpErase® UNG (Uracil-N-Glycosylase), and 0.5 µM of each primer. Genomic DNA was added as template at $10^3$ genomic equivalents per reaction for *Neisseria gonorrhoeae* and $10^6$ genomic equivalents per reaction for *Neisseria meningitidis* and other neisserial strains. Reactions were performed for 60 cycles of denaturation at 95° C. for 15 sec, annealing at 58° C. for 40 sec, and a final extension at 72° C. for 5 min using a COBAS Taqman® PCR System (Roche Molecular Systems, Alameda, Calif.).

Analytical Agarose Gel Electrophoresis of NGDR9Var PCR Products

The PCR products were prepared for gel electrophoresis analysis as described in Example I. The gels were examined for the presence or absence of PCR amplification products at the expected size of 215 bp.

Figure 12A:
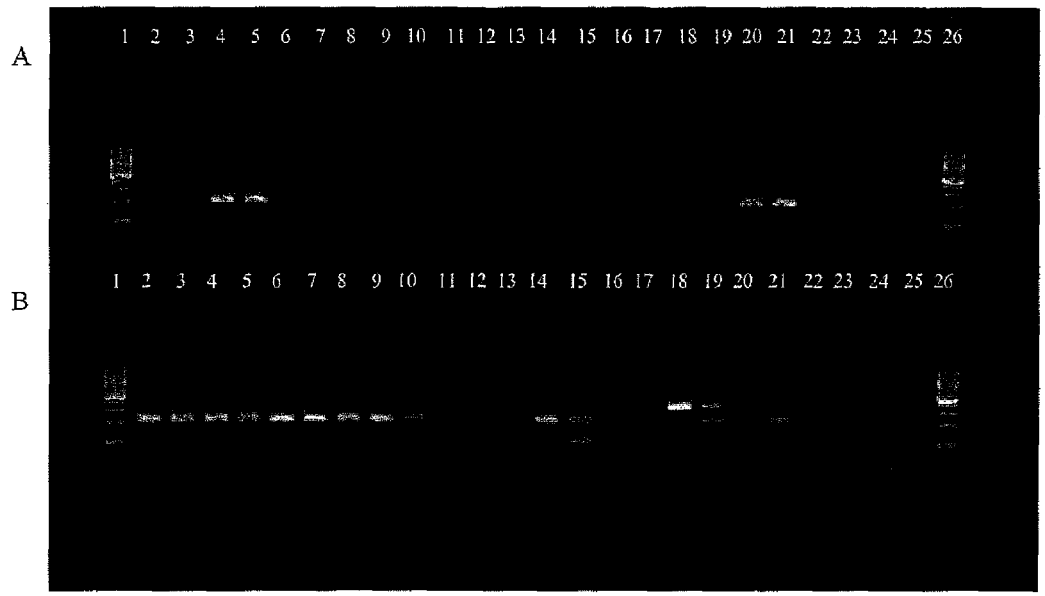

FIGS. 12A and B are photographs of agarose gels that show the detection of the 215 base pair segment of NGDR9Var.

Example VI

Detection of *N. gonorrhoeae* Via *Neisseria gonorrhoeae* Direct Repeat 9

Selection and Synthesis of NGDR9Univ Oligonucleotides for PCR Analysis

In order to utilize a single set of oligonucleotides for simultaneous amplification and detection of NGDR9 and NGDR9Var sequences, both sequences were scanned for regions of maximum sequence identity and consensus sequence upstream and downstream oligonucleotides NGSU2 (5'-GCGGCAAGCATCTGTTTTGC-3') (SEQ ID NO: 47) and NGSL2 (5'-AGTAGCAGGCGCGAAGAT-TGA-3') (SEQ ID NO: 49) spanning a 473 base pair region of NGDR9 and a 394 base pair region of NGDR9Var were synthesized. The deoxycytosine and deoxyadenosine bases at the 3' ends of NGSU2 and NGSL2 primers respectively, had been modified to include t-benzyl groups as described in, e.g., U.S. Pat. No. 6,001,611, entitled "MODIFIED NUCLEIC ACID AMPLIFICATION PRIMERS," issued Dec. 14, 1999 to Will, which is incorporated by reference. The positions of NGSU2 and NGSL2 in NGDR9 and NGDR9Var are underlined in FIG. 11.

Amplification of 473 bp Segment of NGDR9 and 394 bp of NGDR9Var

Separate PCR reactions were performed using genomic DNA isolated from the various neisserial species (as described in Example I) as templates and the pair of primers NGSU2 and NGSL2 (described above). PCRs were performed in volumes of 100 µl containing 50 mM Tricine(pH 8.3), 80 mM K(OAc)$_2$ (pH 7.5), 1 mM Mn(OAc)$_2$ (pH 6.5), 1 mM Mg(OAc)$_2$ (pH 6.5), 5% glycerol, 50 µM dATP, 50 µM dGTP, 50 µM dCTP, 100 µM dUTP, 20 U of ZO5® DNA polymerase (Roche Molecular Systems, Alameda, Calif.), 5U AmpErase® UNG (Uracil-N-Glycosylase), and 0.5 µM of each primer. Genomic DNA was added as template at $10^3$ genomic equivalents per reaction for *Neisseria gonorrhoeae* and $10^6$ genomic equivalents per reaction for *Neisseria meningitidis* and other neisserial strains. Reactions were performed for 60 cycles of denaturation at 95° C. for 15 sec, annealing at 58° C. for 40 sec, and a final extension at 72° C. for 5 min using a COBAS Taqman® PCR System (Roche Molecular Systems, Alameda, Calif.).

Analytical Agarose Gel Electrophoresis of NGDR9Univ PCR Products

The PCR products were prepared for gel electrophoresis analysis as described in Example I. The gels were examined for the presence or absence of PCR amplification products at the expected sizes of 473 bp for the NGDR9 and 394 bp for the NGDR9Var.

Figure 13B:
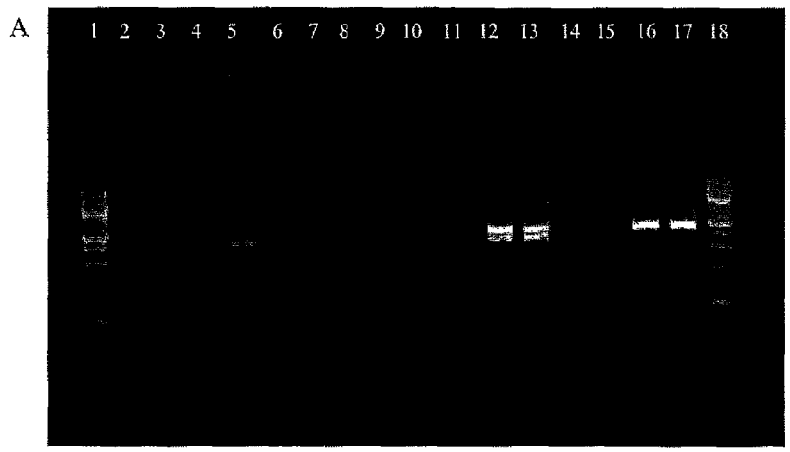

FIGS. 13A and B are photographs of agarose gels that show the detection of the 473 base pair segment of NGDR9 and the 394 base pair segment of NGDR9Var.

Example VII

Assays Illustrating the Selective Detection of *N. Gonorrhoeae* with NGDR9Var Primers This example provides lists of organisms that were analyzed in assays that included the use of primer nucleic acids NG579 (SEQ ID NO: 38) and NG552 (SEQ ID NO: 40) and a 5'-nuclease probe (having a sequence corresponding to SEQ ID NO: 42) alone or in combination with *C. trachomatis* primers.

The inclusivity (i.e., a measure of the ability to detect the target organism, *N. gonorrhoeae* in samples) of these assays is illustrated in Table XII.

TABLE XII

| Genus | Species | Number tested | Primers | Number Positive |
|---|---|---|---|---|
| Neisseria | gonorrhoeae | 538 | NGDR9Var | 62 |

The exclusivity (i.e., a measure of the ability to exclude false positives when neisserial organisms of species other than *gonorrhoeae* are present in samples) of these assays is illustrated in Table XIII.

TABLE XIII

| Genus | Species | Number | Primers | Results |
|---|---|---|---|---|
| Neisseria | animalis | 3 | NGDR9Var | Negative |
| Neisseria | caviae | 2 | " | " |
| Neisseria | cinerea | 5 | " | " |
| Neisseria | cuniculi | 1 | " | " |
| Neisseria | denitrificans | 2 | " | " |
| Neisseria | elongata | 5 | " | " |
| Neisseria | flava | 1 | " | " |
| Neisseria | flavescens | 7 | " | " |
| Neisseria | kochi | 1 | " | " |
| Neisseria | lactamica | 6 | " | " |
| Neisseria | meningitidis | 24 | " | " |
| Neisseria | mucosa | 14 | " | " |
| Neisseria | perflava | 6 | " | " |
| Neisseria | polysaccharea | 3 | " | " |
| Neisseria | sicca | 7 | " | " |
| Neisseria | subflava | 1 | " | " |
| Neisseria | subflava biovar flava | 1 | " | " |
| Neisseria | subflava biovar subflava/flava | 3 | " | " |
| Neisseria | subflava perflava | 7 | " | " |
| | Total | 99 | | |

The specificity (i.e., a measure of the ability to exclude false positives when non-neisserial organisms are present in samples) of these assays is illustrated in Table XIV.

TABLE XIV

| Genus | species | Number | Primers | Results |
|---|---|---|---|---|
| Chlamydia | trachomatis | 15 | NGDR9Var | Negative |
| Chlamydia | pneumoniae | 1 | " | " |
| Chlamydia | psittaci | 1 | " | " |
| Achromobacter | Xerosis | 1 | " | " |
| Acinetobacter | Lwoffi | 1 | " | " |
| Acinetobacter | calcoaceticus | 1 | " | " |
| Actinomyces | isrealii | 1 | " | " |
| Aerococcus | viridans | 1 | " | " |
| Aeromonas | hydrophila | 1 | " | " |
| Agrobacterium | radiobacter | 1 | " | " |
| Alcaligenes | faecalis | 1 | " | " |
| Bacillus | thuringiensis | 1 | " | " |
| Bacillus | subtilis | 1 | " | " |
| Bacteriodes | fragilis | 1 | " | " |
| Bacteroides | caccae | 1 | " | " |
| Bifidobacillus | longum | 1 | " | " |
| Bifidobacterium | adolescentis | 1 | " | " |
| Branhamella | catarrhalis | 1 | " | " |
| Brevibacterium | linens | 1 | " | " |
| Candida | albicans | 1 | " | " |

TABLE XIV-continued

| Genus | species | Number | Primers | Results |
|---|---|---|---|---|
| *Chromobacter* | *violaceum* | 1 | " | " |
| *Citrobacter* | *freundii* | 1 | " | " |
| *Clostridium* | *innocuum* | 1 | " | " |
| *Clostridium* | *perfringens* | 1 | " | " |
| *Corynebacterium* | *genitalium* | 1 | " | " |
| *Corynebacterium* | *xerosis* | 1 | " | " |
| *Cryptococcus* | *neoformans* | 1 | " | " |
| *Echerichia* | *coli* | 1 | " | " |
| *Eikenella* | *corrodens* | 1 | " | " |
| *Enterobacter* | *cloacae* | 1 | " | " |
| *Enterococcus* | *avium* | 1 | " | " |
| *Enterococcus* | *faecalis* | 1 | " | " |
| *Enterococcus* | *faecium* | 1 | " | " |
| *Erysipelothrix* | *rhusiopathiae* | 1 | " | " |
| *Ewingella* | *americana* | 1 | " | " |
| *Flavobacterium* | *meningosepticum* | 1 | " | " |
| *Gamella* | *morbillorum* | 1 | " | " |
| *Gardnerella* | *vaginalis* | 1 | " | " |
| *Haemophilus* | *influenzae* | 1 | " | " |
| *Haemophilus* | *ducreyi* | 1 | " | " |
| *Kingella* | *kingae* | 1 | " | " |
| *Klebsiella* | *pneumoniae* ss *ozaenae* | 1 | " | " |
| *Lactobacillus* | *oris* | 1 | " | " |
| *Lactobacillus* | *vaginalis* | 1 | " | " |
| *Lactobacillus* | *acidophillus* | 1 | " | " |
| *Lactobacillus* | *brevis* | 1 | " | " |
| *Lactobacillus* | *parabuchnerri* | 1 | " | " |
| *Legionella* | *bozemanii* | 1 | " | " |
| *Legionella* | *pneumophila* | 1 | " | " |
| *Leuconostoc* | *paramesenteroides* | 1 | " | " |
| *Micrococcus* | *luteus* | 1 | " | " |
| *Moraxella* | *osloensis* | 1 | " | " |
| *Morganella* | *morganii* | 1 | " | " |
| *Mycobacterium* | *smegmatis* | 1 | " | " |
| *Mycoplasma* | *hominis* | 1 | " | " |
| *Serratia* | *denitrificans* | 1 | " | " |
| *Pasteurella* | *maltocida* | 1 | " | " |
| *Peptostreptococcus* | *magnus* | 1 | " | " |
| *Peptostreptococcus* | *productus* | 1 | " | " |
| *Prevotella* | *bivia* | 1 | " | " |
| *Prevotella* | *corporis* | 1 | " | " |
| *Prevotella* | *intermedia* | 1 | " | " |
| *Propionibacterium* | *acnes* | 1 | " | " |
| *Proteus* | *mirabilis* | 1 | " | " |
| *Providencia* | *stuartii* | 1 | " | " |
| *Pseudomonas* | *aeruginosa* | 1 | " | " |
| *Pseudomonas* | *putida* | 1 | " | " |
| *Salmonella* | *minnesota* | 1 | " | " |
| *Salmonella* | *typhimurium* | 1 | " | " |
| *Serratia* | *marcescens* | 1 | " | " |
| *Staphylococcus* | *aureus* | 1 | " | " |
| *Staphylococcus* | *epidermidis* | 1 | " | " |
| *Streptococcus* | *salivarius* | 1 | " | " |
| *Streptococcus* | *agalactiae* | 1 | " | " |
| *Streptococcus* | *bovis* | 1 | " | " |
| *Streptococcus* | *dysgalatia* | 1 | " | " |
| *Streptococcus* | *equis* | 1 | " | " |
| *Streptococcus* | *pneumoniae* | 1 | " | " |
| *Streptococcus* | *pyogenes* | 1 | " | " |
| *Vibrio* | *parahaemolyticus* | 1 | " | " |
| *Yersinia* | *enterocolitica* | 1 | " | " |
| *Treponema* | *pallidum* | 1 | " | " |
| Herpes simplex virus 1 | | 1 | " | " |
| Herpes simplex virus 2 | | 1 | " | " |
| Epstein Barr Virus | | 1 | " | " |
| Human papilloma virus type 16 | | 1 | " | " |
| Human papilloma virus type 18 | | 1 | " | " |
| Total | | 100 | | |

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. A kit, comprising:
(a) at least one oligonucleotide consisting of at least 90% sequence identity with SEQ ID NO: 68 or with full complements thereof;
(b) at least one oligonucleotide selected from the group consisting of: SEQ ID NOS: 69, 70, a substantially identical variant thereof wherein the variant has at least 90% sequence identity to one of SEQ ID NOS: 69, 70, and with full complements of SEQ ID NOS: 69, 70, and the variant; and
(c) instructions for determining a presence of *Neisseria gonorrhoeae* in a sample by monitoring binding between nucleic acids and/or amplicons thereof from the sample and the oligonucleotide, wherein the presence of *Neisseria gonorrhoeae* in the sample is unknown or unsubstantiated.

2. The kit of claim 1, further comprising one or more nucleic acid detection reagents that detectably bind to a *Chlamydia trachomatis* nucleic acid.

3. The kit of claim 2, further comprising at least one enzyme.

4. A method of detecting *Neisseria gonorrhoeae* in a sample, the method comprising:

(a) contacting nucleic acids from the sample with at least a first set of oligonucleotides in a nucleic acid amplification reaction, the first set of oligonucleotides comprising:
a first oligonucleotide consisting of at least 90% sequence identity with SEQ ID NO: 68 or with full complements thereof, and
a second oligonucleotide selected from the group consisting of: SEQ ID NOS: 69, 70, a substantially identical variant thereof wherein the variant has at least 90% sequence identity to one of SEQ ID NOS: 69, 70, and with full complements of SEQ ID NOS: 69, 70, and the variant; and
(b) detecting one or more amplicons thereof from the nucleic acid amplification reaction during or after (a), thereby detecting the *Neisseria gonorrhoeae* in the sample.

5. The method of claim 4, wherein (a) comprises contacting the nucleic acids from the sample with at least a second set of oligonucleotides in the nucleic acid amplification reaction, the second set of oligonucleotides being at least partially complementary to a *Chlamydia trachomatis* nucleic acid, and wherein (b) comprises detecting one or more additional amplicons from the nucleic acid amplification reaction during or after (a), thereby detecting *Chlamydia trachomatis* in the sample.

6. The method of claim 4, wherein at least one of the oligonucleotides comprises a modified nucleic acid.

7. The method of claim 4, wherein at least one of the oligonucleotides comprises at least one label and/or at least one quencher moiety.

8. The method of claim 7, wherein (b) comprises detecting a detectable signal produced by the label, or amplifying a detectable signal produced by the label to produce an amplified signal and detecting the amplified signal.

9. The method of claim 7, wherein (b) comprises monitoring binding between the one or more amplicons and at least one of the oligonucleotides.

* * * * *

```
                              SEQUENCE LISTING

<160> NUMBER OF SEQ ID NOS: 70

<210> SEQ ID NO 1
<211> LENGTH: 806
<212> TYPE: DNA
<213> ORGANISM: Neisseria gonorrhoeae

<400> SEQUENCE: 1
cagccgcatc atgatgccgc acgtcagggc ttcgtcttcc gatacctttg cgccagacaa      60
catccgggcg atgttttctt tttgcgcttt tgaccgggcg gacagccggt tccggtcaac     120
gtttctgacc gtcccggcgc gtttgacggc gcgttcctgc cgcgttgatt ccttcgccgc     180
gcgtttggcg gcaagcatct gttttgccgt cggttttgtt gctactgttt gcattttgtt     240
ttctcgattt tttgatgccg ttctctcaat gcccaatcat aaagctgtat ctctcacgag     300
gtcgccgaat ttaaattgat agttcatgtc ttgttccatt aatatcaaac gcaatcttca     360
aacacctcaa ttacattttt taaatcgcta ataccataat ttattacatc ctttagaaat     420
tccaaagagg tatccgcttc gtctgcttta tccctaattt cgtctatata accctctaac     480
gattcaggct cttttaatgc ttctttgcat aagttatcta ttacccttaa tgcgttttt     540 acatcttcca aatagctcat tttttgctcc ttaactcaaa atgggatgct gtcgtcaaca     600
tcttctacgg tttatctaat ctgcaaattc ttccgccctt caatcttcgc gcctgctact     660
tgccgaccgc tttcaatcgc ttttctgatg gcggttttgt ccggttcggt tttgacggcc     720
tcacgcataa attcggcggg gatttgtgct tcgtctaaga tcacgacggc ttcggatttg     780
cggaacgagg ctttaaaagt gccgtc                                         806

<210> SEQ ID NO 2
<211> LENGTH: 1142
<212> TYPE: DNA
<213> ORGANISM: Neisseria gonorrhoeae

<400> SEQUENCE: 2
acgccgtggt gcggcctgtt tgtcggatac tgcctgggca aaagcggacg cgcggtcatc      60
agggactggt atcgcgccaa agcctggtca atgtcgggtt tgacgaaact cgaagccccc     120
gcatacggct gcatcgcggt caaaccgcgc cggggcggcg gacacgtgtt cttcgttgtc     180
ggcaaagacg cggaaggcag aatcttgggc ttgggcggca atcagggcaa tatggtatcc     240
atcatcccgt ttgaccctgc ggacattgac ggctacttct ggccgtccaa gctgattggc     300
ggcaaagccg tgccttcgtc ccccgccgaa gggcgttacc ggttgtcgga cgttgccgcc     360
acggcgaaac agggcgcggg cgaggcgtaa atgattgggg ctttgctgaa aaattggaag     420
ccgctgctta ttttgtccgc aatcgcgttc ttcgccgttt cttggcagct ggacagggcg     480
gcgcaatacc gtcgcggata cggtgcggcg gtgtcggagg tttcggaacg cctcaaagcc     540
gccgcggtcg aacacgccga acacgcccgc aaatcgtccg ccgcgtatca ggcgcaaaag     600
gcggcgcgcg aggaaaaaga aagggtgcgc tatgtgcaaa cgcttaaaat cattgaaaaa     660
cctgtgtacc gcaatgcctg ttttgatgct gacggcgtgc gcgaactcaa cgccgccgtt     720
```

```
gacgacggcg gttaagccgc cgccgatttt ggtgcggccc tgcccgaaac tgccgcacct    780
tgaagggaac acgggcgcgg acgtgctgcc gtgggccctg aaggcggccg gtatgtataa    840
cgactgcagg gcgcggcacg gcgcgctggt acgggcgttg ggcgcggatt gagttgtcaa    900
ccggaagttt gcaaccgaac cgtcggttcc gggttggcgg ccgcatcggg ggaagtgtcg    960
gcattccccc cgatttttta catatcgggc ggacgcggca aatttttgcc gttttgtttg   1020
cgcgaagggg gcgttataca aaattatcag gcgcaccaat aatgggcgga atgaaaatg    1080 ccgtaccgat ccggacaaca accgatgccg caccctgcgg gcaggcttcg cactctgaaa   1140
gg                                                                 1142
```

```
<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
cgttctctca atgcccaatc a                                               21

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
agcagacgaa gcggatacct c                                               21

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
ctctcaatgc ccaatcataa agc                                             23

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
gtatccgctt cgtctgcttt atc                                             23

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
gtttggcggc aagcatct                                                   18
```

```
<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
aaatgggatg ctgtcgtcaa                                            20

<210> SEQ ID NO 9
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
ggcaagcttg tttggcggca agcatct                                    27

<210> SEQ ID NO 10
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
ggcggatcct tgacgacagc atcccattt                                  29

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
aaacgcaatc ttcaaacacc tca                                        23

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
tttgacggcc tcacgcataa                                            20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
tcaatgtcgg gtttgacgaa                                            20
```

```
<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
aacgtccgac aaccggtaac                                                   20

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
aatgtcgggt ttgacgaaac tc                                                22

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
gttaccggtt gtcggacgtt                                                   20

<210> SEQ ID NO 17
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
cgaggtcgcc gaatttaaat tgatagtt                                          28

<210> SEQ ID NO 18
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
aactatcaat ttaaattcgg cgacctcg                                          28

<210> SEQ ID NO 19
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
cgaggtcgcc gaatttaaat tgatagttca                                        30
```

```
<210> SEQ ID NO 20
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
tgaactatca atttaaattc ggcgacctcg                                            30

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
gcggcaatca gggcaatatg gtat                                                  24

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
ataccatatt gccctgattg ccgc                                                  24

<210> SEQ ID NO 23
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
ggcggcaatc agggcaatat ggtat                                                 25

<210> SEQ ID NO 24
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
gataaagcag acgaagcgga tac                                                   23

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
ttgacgacag catcccattt                                                       20
```

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
ttatgcgtga ggccgtcaaa                                               20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
aacgtccgac aaccggtaac                                               20

<210> SEQ ID NO 28
<211> LENGTH: 405
<212> TYPE: DNA
<213> ORGANISM: Artificial Sequence
<220> FEATURE:
<223> OTHER INFORMATION: Description of Artificial Sequence: Synthetic
      consensus sequence

<400> SEQUENCE: 28
gcatctgttt tgccgtcggt tttgttgcta ctgtttgcat tttgttttct cgattttttg    60
atgccgttct ctcaatgccc aatcataaag ctgtatctct cacgaggtcg ccgaatttaa   120
attgatagtt catgtcttgt tccattaata tcaaacgcaa tcttcaaaca cctcaattac   180 atttttttaaa tcgctaatac cataatttat tacatccttt agaaattcca aagaggtatc   240
cgcttcgtct gctttatccc taatttcgtc tatataaccc tctaacgatt caggctcttt   300
taatgcttct ttgcataagt tatctattac ccttaatgcg ttttttacat cttccaaata   360
gctcattttt tgctccttaa ctcaaaatgg gatgctgtcg tcaaa                   405

<210> SEQ ID NO 29
<211> LENGTH: 370
<212> TYPE: DNA
<213> ORGANISM: Neisseria gonorrhoeae

<400> SEQUENCE: 29
gttgctactg tttgcatttt gttttctcga ttttttgatg ccgttctctc aatgcccaat    60
cataaagctg tatctctcac gaggtcgccg aatttaaatt gatagttcat gtcttgttcc   120
attaatatca aacgcaatct tcaaacacct caattacatt ttttaaatcg ctaataccat   180
aatttattac atcctttaga aattccaaag aggtatccgc ttcgtctgct ttatccctaa   240
tttcgtctat ataatcctct aacgattcag gctcttttaa tgcttctttg cataagttat   300
ctattaccct taatgcgttt tttacatctt ccaaatagct catttttgc tccttaactc   360 aaaatgggat                                                          370

<210> SEQ ID NO 30
<211> LENGTH: 375
<212> TYPE: DNA
<213> ORGANISM: Neisseria gonorrhoeae

```
<400> SEQUENCE: 30
ctgtttgcat tttgttttct cgattttttg atgccgttct ctcaatgccc aatcataaag    60
ctgtatctct cacgaggtcg ccgaatttaa attgatagtt catgtcttgt tccattaata   120
tcaaacgcaa tcttcaaaca cctcaattac atttttaaa tcgctaatac cataatttat    180
tacatccttt agaaattcca agaggtatc cgcttcgtct gctttatccc taatttcgtc    240
tatataaccc tctaacgatt caggctcttt taatgcttct ttgcataagt tatctattac   300
ccttaatgcg ttttttacat cttccaaata gctcatttt tgctccttaa ctcaaaatgg    360
gatgctgtcg tcaaa                                                    375

<210> SEQ ID NO 31
<211> LENGTH: 400
<212> TYPE: DNA
<213> ORGANISM: Neisseria gonorrhoeae

<400> SEQUENCE: 31
tgttttgccg tcggttttgt tgctactgtt tgcattttgt tttctcgatt ttttgatgcc    60
gttctctcaa tgcccaatca taaagctgta tctctcacgg ggtcgccgaa tttaaattga   120
tagttcatgt cttgttccat aatatcaaa cgcaatcttc aaacacctca attacatttt    180
ttaaatcgct aataccataa tttattacat cctttagaaa ttccaaagag gtatccgctt   240
cgtctgcttt atccctaatt tcgtctatat aaccctctaa cgattcaggc tcttttaatg   300
cttctttgca taagttatct attaccctta atgcgttttt tacatcttcc aaatagctca   360
ttttttgctc cttaactcaa atgggatgc tgtcgtcaaa                          400

<210> SEQ ID NO 32
<211> LENGTH: 405
<212> TYPE: DNA
<213> ORGANISM: Neisseria gonorrhoeae

<400> SEQUENCE: 32
gcatctgttt tgccgtcggt tttgttgcta ctgtttgcat tttgttttct cgattttttg    60
atgccgttct ctcaatgccc aatcataaag ctgtatctct cacgaggtcg ccgaatttaa   120
attgatagtt catgtcttgt tccattaata tcaaacgcca tcttcaaaca cctcaattac   180 atttttaaa tcgctaatac catcatttat tacatccttt agaaattcca agaggtatc     240 cgcttcgtct actttatccc taatttcgtc tatataatcc tctaacgatt caggctcttt   300
taatgcttct ttgcataagt tatctattac ccttaatgcg ttttttacat cttccaaata   360 gctcatttt tgctccttaa ctcaaaatgg gatgctgtcg tcaaa                    405

<210> SEQ ID NO 33
<211> LENGTH: 405
<212> TYPE: DNA
<213> ORGANISM: Neisseria gonorrhoeae

<400> SEQUENCE: 33
gcatctgttt tgccgtcggt tttgttgcta ctgtttgcat tttgttttct cgattttttg    60
atgccgttct ctcaatgccc aatcataaag ctgtatctct cacggggtcg ccgaatttaa   120
attgatagtt catgtcttgt tccattaata tcaaacgcaa tcttcaaaca cctcaattac   180 atttttaaa tcgctaatac cataatttat tacatccttt agaaattcca agaggtatc     240 cgcttcgtct gctttatccc taatttcgtc tatataaccc tctaacgatt caggctcttt   300
```

```
taatgcttct ttgcataagt tatctattac ccttaatgcg ttttttacat cttccaaata    360
gctcattttt tgctccttaa ctcaaaatgg gatgctgtcg tcaaa                    405

<210> SEQ ID NO 34
<211> LENGTH: 11498
<212> TYPE: DNA
<213> ORGANISM: Brucella suis

<400> SEQUENCE: 34
accgaaaccg ctctaactgc aatgacaaag gcagctttga ttacatggca actggccgaa     60
gcgcaaacaa actgtgcaac gggaagttaa aaacaaaatg cccggctaaa agccgggcag    120
attgctgaat tttgtagcat tttttgctaa tatatcaggc aatttacttc tggaagtaat    180
tatacttgcc gtcttcgccc ttgcgccatt caaacatgac atagggcgac aggctcggat    240 caccccttcgc atcgaaggag atatcgccga gcacggtctt gaacggaccc ttttccttca    300
tcgcggtagc gacttccatc ggatcattgc tgccagccgc attggccgcg ttcacaagcg    360
attgcacacc ggcataggca tagaacgtat aggcttccgg ctcgaaaccc ttgtcacgga    420
acgccttgat gagttcggca ttggccttgt cgtcgcgcgg atcgggaccg aaagtattca    480
tcacaccggc cacggcgtca ccggcaatcg acgccagctc gttggacacg atgccgtcac    540
ccgaaatgaa ctgggctttc agcccctgat cggccatctg gcgaatcaga aggccagctt    600
ccgggtgcat accgccccag taaacggcag tgatgcccgc agctttcatc ttggaaatga    660
gcgcggagaa atccttgtcg ccctgattca cgccctcata gagcgtttcc ttcatgccgt    720
tctcgttgag cgacttttta gtttcgtcgg caaggccctg accatagggc gtcttgtcgt    780
gcagaatggc aaccttgccg tccttgtaat tatcggccat gtacttgcct gcgacaatgc    840
cctgcttgtc gtcgcggcgg caggtgcgga atgtgttcca caattcgcgc tcggtaaagg    900
tcgggttggt cgtgcccggt gcaatcatca gcacgccgtt ttcggcatag atatccgagg    960
tcggaatgct gacaccggaa ttgaaatggc caatcacaaa cttgacgcca tcgcccacga   1020
acttgtttgc aaccgagatg ccctgcttgg gatcggcagc gtcatcacca taaacgaggg   1080
tgatctgctc accattcatg ccgcccttgg cattggcttc cgcgacagcc gcctccacgc   1140
cgcgcttgat ctgttcgccg aaggcagcct ggctgccagt caggggcgca ccaacaccga   1200
ccatgatatc ggcgaaagat gtcccgccca tcgcgaccag cgcacaaagg caaacgccgc   1260
aaaataagga tttcttcatt tcgattgctc ccattatgaa cggcggttcg ccgcccgacg   1320
cagtgcgaac cgcaaatttc agggcagatt cctcgaaccg cccgatgcct tgcagaattt   1380
ccgcacgaga acgcaacctc atgcgtgaga tctgccgatg ttcaatggga agaatgcgtc   1440
agcccacgac cgcttgtgtc cggccaattg ccggaatgcg cgcctcccct cctctccctt   1500
tcacggcatg agagcgtttc acgcttttgc cggaaatatt ccagaaggca caatcggtgc   1560
cagggtcgcc catgctgaaa ccgctcctcc caccggaacg caacaccaga gcgcgttttt   1620
atctgattga atcagactgg cgctctccat gttgttttga cgcgcttctt atccgaaaat   1680
catttcacac ttttcgggat gcgctctaga tttagaggat cgctctatat ccagccgtca   1740
caatagataa agtcgcttta tatatggaag taaagcaatg attcactcta catcctgcgt   1800 tttcgcatg actttatgcg ggaaggcgga ttgcaattga aaatgcccgg cttcaaaagc   1860
cgggcatctg atattttcag aaaagaatat gacggaaact tactgctgaa tgtaattata   1920
cttcccgtct gcaccctttt cccacttgta catgacatag cccggaagct tcggatcacc   1980
cttttcatca taggacagat cgccgagcac ggtcttgaac gggccctttt ccttcatggc   2040
```

```
tttggcgact tcctgcggat cattgctgcc agcggccttt gcggcctgag ccagcgactg    2100
aaccgccgca taggaataga gcgtataggc ttccggctca aaaccggcgt cgcggaattt    2160
cttcaccagt tcggcattat ccgggttgtt gcgcggatcg ggaccgaagg tgttgagcgt    2220
gccttcgaca gccggaccgg cgattgacgc cagctcgttc gacacaatac cgtcacccga    2280
aatgaactgg gcttttagtc cctgatcggc catctgacgg atgatgagac cggcttccgg    2340
gtgcaggcca ccccaataaa ccacgttcac gccagcctgc ttgagcttgg cgatcagcgc    2400
cgagaaatcc ttttcaccaa cgttcacgcc ttcatagagg gtttccttgg tgccaagttc    2460
attcagcttc ttcttggttt cgtcggcaag cccctgaccg taaggggtct tgtcgtgaat    2520
gacggcgatc ttcgcatcct tgaagtggtc aaaaatatac tgaccggcaa cagtgccctg    2580
ctgatcatca cggccgcagg tgcggaatgt gttccacagc ccctgctccg tatattgagg    2640
attggtcgcg ccaggcgaaa tttcgagaat accgttttcg gcatagacct gcgaagccgg    2700
aatggtaacg ccagagttga agtgtccaat cacgaacttg acgccatcgg cggcaaattt    2760
attagccacc gaaatacccT gcttcggatc ggatacgtca tcgccgattg tgatggcaat    2820
cttctcgcca ttgatgccgc cggcatcgtt gacttccttg attgccgcct cggcgccttt    2880
ctggatctgt gcaccataaa cggcgttcgg gccggttaca ggaataccga taccgaccag    2940
tacatcagcc caagccgagc ccccgaaggc gatgactgca gcaagagcaa cgcccgaaaa    3000
aagtgttttt ctcattgttg gaactcccaa attttgttta ccccgaagcg atgttttcgc    3060
atcgccttat tatcttgtcg attaatcgac aatatctacg ttgaatctta ttattatcaa    3120
cgtgatcttt taaaaaagct ccgccgcata acggcgaagc tttaaattat ttcgccttcc    3180
agccgaatgg agaggttttt tcgtagagcc agctatactg gcgcaccatc tgcttggtgc    3240
gcgtatagcg aaagcccacc gtgccgataa tcatcagcac gatcgtgtcc accagataat    3300
agtggagcga caaaagcgtg cccccaaaca acgcataatg aatgaaacgc actgcagctc    3360
ccagcgggat catatagatc aggaactgca cataggtccg ccatgtggat gcgcaggcgc    3420
ggcctgccat ccatgccgcc cagccgccca gaaggcaggt gatgaggaaa acagccaga    3480 atgacggttc ttcgtagaga ataccctgca tgttttttctc ctaatgcctt ccgccttcga    3540
gataagccgc acgcacttcc gggtcggaca aaagttcacg tcccgaacca ctcatcgtga    3600
ttgatccgtt gaccatcaca tagccgcggt cggcaagctt cagcgcaccg aatgcgttct    3660
gttcgacggg gaataccgtc aaaccctgtg tgcggttcaa ttccttgatg gcctcgaaga    3720
tctgcttcac gatcagcggc gcaagaccca gtgacggctc atcgagaagc aggagcttcg    3780
gacgcgccat cagcgcgcgc gcaatggcca gcatctgctg ttcgccgccc gaaagcgtgc    3840
cgccgcgctg gttgatacgc tccttcagac gcgggaacag atcgaacatc agctttacgt    3900
cttcatcgaa atattgctga ttatcgaggc tcgcgcccat ctggaggttt tccagaaccg    3960
tcatgcgcgg gaagatgcga cggccttccg gcgactgcgc aatacgtagc ttcgcaatct    4020
cgtgcggcgg catggaggta atgtccttgc cattgaagag aatgcgaccg gtgcgcgcgc    4080
ggcgagccga agatcgtcat catcaatgtg gatttgcccg caccgttggc gccgatcagc    4140
gccacgatct cacccTcatc cacggtcata tcgatgccct tgagcgcaca gatattgccg    4200
taataggtct cgaccttctc gacggatagg agcggttgct ttttctgcat ggtttcagcc    4260
tgcatcattc gcctcccttt gcgggcttgg ccgaagcttt cgacggcgcc tcggtgcttt    4320
tcgcagcacc cttgccagcc tttgcgggag aagttttgtg gctcgacgga acatcgccgg    4380
cttcaacgcg ctgcgcaaac tcagttgcct ggcctgccgc aagctgtctg gcctggccga    4440
```

```
cccagtcttc gcgggcaatg cgcccgtcga attccagata ggtttcagcc tgctcaatat    4500
ccgtttgcgt ccatgcagcg atctggtcga aatgatagat gccgtgctcg ttgagctttt    4560
tctcgttgac ggcgccaatg cccttgatga gcgtaagatt atcggccttg ccgccgcgcg    4620
cactttccag cccgcccgca agcgcggcct tgccggaagc aagcctctcg ccctttcttt    4680
ccgcaaccgc ttcctcggca agctgcgtcg caatcagatc cgccggatct tcgacaccgg    4740
gcttgtcggc cccttcgatc aggtccgcaa tctcctcgtc atcgacaccc agataggcag    4800
caataacacg cggatcgttc ttgacctctt ccggcgcgcc atcggaaatt ttcgttccat    4860
attccagcac gatcacatgg tcggagattt ccataaccac cgacatgtca tgttcgatga    4920
gcaggatcga cgtgcccgtc tccttgcgga tatcgagcaa aagcgtgttc agctctgccg    4980
attcacgcgg gttgaggcca gccgccggct cgtcgaggca gaggatttcc gggtcggtgc    5040
acatggcgcg ggcaatttcc agacggcgct ggtcgccata aggaaggtcg cccgccggat    5100
catcagcgcg cgcgatcaga ttgatctttt ccagccagaa gcgcgccttc tcgatggctt    5160
ccttcgccgc cgtcttgtag cccggcaatc ccagaagacc gaggatcgtg taacctgaag    5220
agcgcatcag tgtgttgtgc tgcgcaacca gcaggttttc cagaacggta aggcccgaaa    5280
agagccggat gttctggaaa gtacgcgcca ccttggcctg tttggtgatc tggaaatcgg    5340
gcaggcgctc cagaaggaaa ttctcgcccg ttttccgatg catggtcagc ataccgcccg    5400
tcggcttgta aaagccggtg atgcagttga aaaccgtggt cttgcctgca ccattcgggc    5460
cgatgatcgc agtgatatcc ccgcgcttca cgtcaaagct cagatcattg atggcgatca    5520
ggccaccgaa gcgcatcgaa agatgctcga cttggagaat ggtgtctttc aaaccattac    5580
cagacataat gctcgtctcc gccatcagcc gtgcccttcc ttggtaaagg cgcctgacac    5640
catcttcctc gcattcagga acgcgctcgg ttcacggctt cccacgaaac cacgcggttt    5700
ccagaccatg acaaccacca tggcaaggcc gaagatcaac atgcgataga gttccggcgt    5760
aaagtccggc ccgaagatta tcttcaggaa gctcatctca cgcaggattt ccgtaccgcc    5820
aatcatgaca atcgcggcaa tcgcgatgcc gacgagcgaa cccatgccac ccagaaccac    5880
aatggccaga atgactgcgg attcgaggaa cacgaaggat tccgggctga cgaagccctg    5940
acgtgcggca aagaacgaac cggcaaaacc accgaacatc gcgcccgtgg caaacgccgt    6000
gagcttggtc gtggtggtgt tgatgccaag cgaacggcag gcgatctcgt cttcacgcaa    6060
agcttcccac gcgcgcccca ccggcatgcg gcgcaggcgg atcgtaaccc aggccgtcag    6120
gagggccagc aggagaatga cgtaatagag aaagaattta taatgcgccg ctgagaaggc    6180
caggccgaaa tgagcggcaa aaccgtcctt gctcgcattg aaaggcagac cgaagaaggt    6240
tgccttggca atgccggaaa tatcgaaggt gccgcgggta aggtcggtcc agttgatgag    6300
gaccagacgg atgatttcac cgaaggcaag cgtgacgatt gcaagataat cgccgcgcag    6360
gcgcaacacc gggaaaccca gaatgatgcc ccatgtcgca gcgagcagac cggcgatggg    6420
cagaagcacc cagaacgaca ggccgaaata gctggacaga atggcatagg aatatgcgcc    6480
aaccgcatag aaggccacat agccaaggtc gagcagaccg gcgagaccca ccacgatatt    6540
gaggccccag gccagcatca catagatgag gatctggaca ccgaaattat ccacccactc    6600
caacgatccc tgccagccaa gggctgcaac gatgagaacg ggatagacaa agaggaaggc    6660
aacgccaagg cgtgagaaat tgcggcggac aaaagaaggg ttttcggttg agaccgcggg    6720
ccggctgctt ttggcgagct tgcgcgcctc cagccagggc tggagaaagg cgatgaaaag    6780
gaagcgccca accgctgcga tcgcgaccat gatggccagc gttccccagc gctgttcgag    6840
```

-continued

| | | | | | |
|---|---|---|---|---|---|
| caccaattcg | ttgttgatgt | tctgatcggt | cttgaaaccg | atgatgaggc | agaagagacc | 6900 |
| gagagccaga | agaccggcca | tgatcccttc | gcgcagagcc | cggccgaaaa | gggaatccgg | 6960 |
| gcgtgaacca | gtttgtactg | ccatgattac | acctttcga | cttcaggtcg | gccaagaatg | 7020 |
| ccggacggca | tgaagatcag | cacgatagcc | aggatcgaga | acgcggcgac | gtccttgtag | 7080 |
| tcgatcgaga | aataggccga | ccacaacgct | tcgatgagac | cgataagcaa | cccgccgaca | 7140 |
| acagccccg | gaagcgagcc | gatgccgccc | agaaccgccg | ccgtgaacgc | cttcacaccg | 7200 |
| gggatgaacc | cgtcagcgaa | cgaaatcacg | ccatagaagg | agaggtaaag | cgtcccggct | 7260 |
| acggccgcca | gcatggcgcc | catcacgaag | gtgagcgaga | tgacacggtc | gacattgatg | 7320 |
| ccaagaaggg | ccgccatctt | gcgatcctgc | tcgcaagccc | tttgcgcgcg | cccagcgag | 7380 |
| gtgcggttga | cgacatacca | gaagatcgtg | agcaatattg | ccgtaaccac | gatcaccacg | 7440 |
| atctgcttga | gcgagatcgt | gacgccgctg | ccgaacagct | cgtaggaacc | attcagaagc | 7500 |
| tggggaaccg | gcttgttgcg | cggacccttgc | gtgacctgaa | cgaagttcga | caaggcaatc | 7560 |
| gacatgccga | tagccgtgat | cagcggcgca | aggcggaacg | aaccacgcag | cggtcgatag | 7620 |
| gccacgcgct | cgatcgccca | gctccacaga | cccgtcagaa | gcatggcgac | gatcatcatc | 7680 |
| aaaagcagca | tcagtgcaac | cggcagcatt | ccggtgaagg | tcgtgataat | gaggaaaaca | 7740 |
| atcagcgcca | tgaacgcgcc | gagcatgaag | atatcgccat | gagcaaagtt | gatcatgccg | 7800 |
| ataatgccat | agaccatcgt | ataaccgatg | gcgatcaggc | catagatcga | accgagcgca | 7860 |
| agcccgttga | tcacctgctg | gaagaaatat | tccatagaga | agccacccat | tttattgtcc | 7920 |
| gggattttat | ttgccgcatc | ttcttgcgta | cggcttcatt | ttattcccgg | tccatttaca | 7980 |
| cctaacggct | gtatagagga | atgcaagccc | cttttgtcgc | aggcaaaaga | caaagtctct | 8040 |
| cattccgtca | caaactagtt | atgtcccta | tcaaatgccg | tgtatatgtc | ttttctcct | 8100 |
| acccggccta | cgttattcca | tatttttccc | acacacgaaa | aggcaaataa | atgggaaggt | 8160 |
| ggaaataatt | tcgcctgttc | tacccacttt | atgccacgct | gaacccatga | gcaaacggat | 8220 |
| cgcgatcgtc | gataaaaatc | gtattatagc | ccgtcatccg | cgcccagcct | gcaatggaag | 8280 |
| gcacaattgc | ggggcgcccg | gcaacctcgg | cggcgcgctc | cacacgacca | tggaatagcg | 8340 |
| agccgatgat | cgattcatga | ataaattcat | cgcccggttt | cagcttgccc | ttggcggcaa | 8400 |
| gctgggccat | cgcgcgccgac | gtgccggtgc | cgcaggggcga | acggtcgata | gccttgtcgc | 8460 |
| cataaaacac | ggcattgcgc | gcatgggctt | gcgggtgctt | cggcttttccg | gtccagagaa | 8520 |
| tatggctgag | acgttgata | tcaggcagtt | ccgggtgctg | gaacttgtat | ttttcattca | 8580 |
| gccgctggcg | caggaccggg | ctccaggcaa | taagctgaag | cgcggagtaa | tcgtccatat | 8640 |
| ccgtgtagtt | ttcctgcggt | tcgacaatgg | cgtagaaatt | accaccataa | gcaacatcga | 8700 |
| ccttgatcgg | gccaagatcg | gggcattcga | cctccaggcc | ttcggcataa | aggaaagctg | 8760 |
| ggacattggt | gaggcgcaca | cgctccacat | actgaccgtc | ctgctcatat | tcgatcgcca | 8820 |
| ccaggccggc | gggcgtgtcg | agattgagct | tgcccggcgt | cttgggcgtc | accagtccct | 8880 |
| gctcgattgc | catcgtcacc | gtgccgatgg | tgccatggcc | gcacatcggc | aggcagcccg | 8940 |
| aggtttcgat | gaacagcacc | gccacgtcgc | aatccgcct | tgtcggcgga | tagagaatgg | 9000 |
| aaccggacat | catgtcgtgg | ccgcgcggct | cgaacatgag | gccggtgcgg | atccagtcat | 9060 |
| attccgccag | gaaatgcgcg | cgcttttcca | tcatggtcga | tccattgagg | ttcggcccgc | 9120 |
| cgccagccac | cagccgcaca | gggttgccgc | atgtatgccc | atcgacgcag | aagaaggaat | 9180 |
| gtcttgccat | tatggtcagt | tccgaaaacg | ttgaggcttg | aaaggttcga | tatcgattgc | 9240 |

```
aggttcgcta cccgtgatga ggtcgcggat aagccgcgcc gtcgccgccg attgcgtaag   9300
gcccagatgc ccatggccga aaccgtaata acattgccca cccgccgaag cgcggccgat   9360
aaccggaagg gaatccggca tggagggccg atacccatc cattgcctgc cgccttcaac    9420
cttaaggccc ggcaaaaact tcgatgcttt cttcagcatc gcttcggagc gtgcaaaatt   9480
gggcggcaga tccagcctac cgaactccac cgctccgcca acacgaaggc cggtctccat   9540
tggcgtaatg acaaagccat ggccgggaaa cgttagctgg cgctttacat caaagctgcc   9600
gaccagaagc gtcgtattgt aaccgcgttc ggtatcgagc ggcacgatat cgccgaagcc   9660 cttttgccaga tcccgcgacc acgcacccgc catcagcacc agatgagtgg cattgatctc   9720 cacccgttt tcaagccgca gacgaacgcc gccattctgg cgcttggcgc tcgcaacctt    9780
gccgaaaagg aaccgtgcgc caagactttc cgcataggac cagatcgcct tgccgaaaag   9840
cttcggatcg ctcacattct tccagccagg cacgaaagtt ccagccacga agcgcgggtt   9900 cagcccggc tgcaattccg caagccgcct gccgcgcaca tgttcatagg cgatgcccgc    9960
cttttcgcgc acatcccagc cgggctgcga ggccgcaagc tccgcctcgc tttcgtaaag  10020
ctccagattg ccgtcttcac gcagcctgtt gcgcaagccc gcacgctcga tcagcgactg  10080
catctcgttt tccgcaaggc gcatgatggc cgcttgcgca atggccgttc tggccaaggc  10140
attgggcgcg ctggccgcca gaaacgatag agccggggaa gcattttggg gaaataggtg  10200
gggcgaatgg tgaaagggcc aagcgggtcc agaagccagc ccggcacctt gcgcatcacg  10260
cctttcgagg caagcggcag aatatcggaa aaggccagcg ctgccgcatt gccggaactc  10320
gtttcctcgc aaatgcctgt ccggtcaata acgagcacct cgcgcccggc ctcggcgagc  10380
aatgcggcgg tggcgacacc gacgatcccc ccgccaatga tgacgatatc ctgctgaccc  10440
tgtggatcag atttcatttc tgtgcggctc cccgaccgtc ttggcatatt gcgaaatgtc  10500
cagctcctcc ggcatcgaca cgtctttcat cgcgagcccc gtgtggaatg tctatcgatt  10560
tttcggaatg atgctgtgcg aaaattatct atggagcgat gttcggccca gatctcgcaa  10620
agaggaaaag ccgaacgcct gcttgtttcg agacttcacc tttcgtttga tatatcagtg  10680
atatatctat acacttgcat tatgtcaatc acgtttgtca caaagcaaga agcagcatgg  10740
aacaggttaa agcgcacgaa acatctgcga accgcccccg tggccttgcg ctggcggag   10800 ttgatggctg ggcaagtgaa agcctggccg aacaggccta ccagattctt gaacggctga  10860
tcgtcacgct ggagcttgaa cccggcacac tcgtcaacga acgcacgctg atcgatctga  10920
ccggcatggg ccgcactccc ctgcgtgagg ccatacagcg ccttgcatgg aagggctga   10980 tggaggtgcg cgcccgatcc ggcatcgcca tagcgccgat cgatccgaag gatttcatca  11040
aggttctgga tgcgcgcgag ggcgtggaac gggtgctggc ccgcgacgct gcgcgtttcg  11100
gcagcccgcg cgattacgag aggctcgaag ccgcagccaa ggccatgcgg caggcggttc  11160
caaccgagga cgtgtccctg tttctggatg cggacaaggc atttgatatc gtgctgggtg  11220
cagccgcaag caatccctat gcggcgcgca tcgtggcccc cttgcaaagc catagccgcc  11280
ggttctggtt ccgccttcgc ccatcatcgg gcatcgcagg ctcggccaat gcccacgcga  11340
ccctgatcga agcgatcatt tcacgcgacc cggaacgcgc cagtgatacg gccagcgaac  11400
tcatggccta tctgcgcaca ctcgcgccat agaacatttt cggtactggc caaataaaaa  11460
accggagcaa agccccggtt tcttcatcgg ttcgcgcg                          11498
```

```
<210> SEQ ID NO 35
<211> LENGTH: 11133
<212> TYPE: DNA
<213> ORGANISM: Neisseria meningitidis

<400> SEQUENCE: 35
tgaaaggcaa atcgtggcgg ggcgcaaagc cgcaccggtt tggggatttc cgcaataatt      60
tttaatatcg ataggttata tggctatggc taaaaatgtt gtagtaatcg gcgcacagtg     120
gggcgacgag ggtaaaggta aaatcgttga ctggctggcg gaagaagccg gcggcgtggt     180
gcgcttccaa ggcggccaca atgcgggcca taccttggtt gtcggcggca aaaaaaccat     240
tttgcgcctg attccgagcg gcatcctgca tgaaagtttg gactgcttca tcggttcggg     300
cgttgtcgtc tcccccgaag ccctgttggg cgaaatcgac gagttgaacg cggcaggcgt     360
gaaaaacgtc gaaggccgtc tgaaaatcgc gccgacctgc ccgctgatcc tgccttacca     420
catcgcgctc gaccaagccc gcgaagcatc gcgcggcaaa ggcaaaatcg gcacgaccgg     480
ccgcggcatc ggccctgcct acgaagacaa agtggcacgc cgcgccattc gcgccgcgca     540
tttgctgcat cctgaaaaac tgcgtgaaaa actggatgcc gtccttgcct attacaatgt     600
ccaactgcaa catctgcaca atgccgagcc ggttaaagcg gaagacgtga tggcggttat     660
cgaaaaagtc gcgccgcgca ttgcgccgat gattaccgac gtgtcccgcg tgttgaacga     720
gaaaaacaaa aacggcgaaa aactgctgtt tgaaggcgcg caaggtgcgt tgttggacat     780
cgactacggc acttatccct tcgttacctc gtccaactgt ctggcgggcg cagcttcggc     840
aggcgcgggg gtaggtcctc aaatgctgga ttatgttttg ggcatcgtca aagcctatac     900
cacgcgcgtc ggttcgggcc cgttcccgac cgaattgttc gacgaagtag gcgtaggttt     960
ggcagaacgc ggacacgaat tcggttcggt aaccggacgc gcacgccgct gcggctggtt    1020
tgatgccgcc gccctgaaac gctccatcca aatcaacggc atttccggta tgtgtattac    1080
taaactcgat gtaatggacg gcgttgaaac catcaatatc tgcgtcggct atgaattgcc    1140
cgacggcggc aaaaccgaca tcctgccttg cggttccgat gcggtggaaa cctgcaagcc    1200
gatttacgaa accatgcccg gctggcgcga atccactttc ggcgtgaagg actacggcgc    1260
attgcccgaa aacgccaaag catatttgaa acggattgaa gaagtctgcg gcgcgccggt    1320
cgccatcgtc tccaccggcc ccgaccgaga gaaaacgatt gtgctgcatc atccgttcgc    1380
ataaggtttt gcagtaaaat tgccgtctga agccctaatc cgccgttggt cataaatagt    1440
agggtatcaa catttcgggc tacaatggta cgtcagccaa tgccaagacg tgccagcctg    1500
atttgttgat gtgtgtacta ttgcataggc ggttaagcca tgcaggagat gaaagtgtat    1560
atgtcgcgca aagcccatta gccgcaagcg aggggcgggg tgcgcgagag agaggggggc    1620
aggtgctaag tcattggtta tctccttact atctatctaa ctacgggtgc attatgcgcc    1680
tatgcctgtt ttttgtcaaa cactatacag ttaaaatgtg taaatattta gtaaggacat    1740
ataccctttt ctttacattt agctccatcg gataccagtg cgttcagaga aaatttgaaa    1800
atttctatat tttggttgta taatgctttc attttagaaa ggtctataat gccaaaatca    1860
ctctcgctac aagatgttca gttaaggttt tccagtaaat ttcctgataa gacgttttg     1920 aagttcacta aaaactacga accggtaaca atccaatgcc ctttgcatgg gtcggttgtt    1980
tacgggaatc tacaagctgc catgaaatcc tcaacaggat gtcctgaatg tactcgaaat    2040
cccgaaaagc cctctccaaa cgccgttgcc attaggttgg aggacacaga gacaggggaa    2100
atctacgagt ttgcaagtac actggctgcc agtaaattta tcggttgctc caacagcact    2160
ttagctgtac gtttaagcgg acgcactccg tttgaccgat tgattaggta tcgttatagg    2220
```

```
ttggtaaagt aagttcacaa ccactatggc acttacattt actcaagcag tttctaagct    2280
aacctctaaa tttccacatt tgaatcttgt ggagttcaat ggcgttcgtt acccgacggt    2340
aatcgtctgt cctatacacg ggagggttac ttgctctaca ttcaaaagta tgttggactc    2400
taaaagtggg tgtccaaaat gtgcatctta tggtgtcaat tcccacaaaa ttccagaaga    2460
tacaatagat aaattatcta aaatacagt attggaggat actgtaactg gcgaaacact     2520
tacattcccc tcaagagcat ctgctgcaag gtcattgggt ataaacccag cagctatcac    2580
tgaccgtata aaaggtcggg ttcacacaga gactttactt gcagggaggt ataaggttca    2640
catctgcact aaatgacgta tacactttt aacagtgtat accctcgcc actatcaggt      2700
gcttctcgaa aaatttgaca tttttataaa tttgctatta aatccatttg acaatcaatt    2760
ttggagtctc aaatggccaa atcttcaac caagcagctt ctgaacttac tgatatattc     2820
cctaatatct ctctaaccgg cttgacggt gtgaattacc cagtaaccgt taattgtcct     2880
atgcacggga acgttcgtta ttcgacattt aatgcccctta taaagtcaaa gtacgggtgt   2940
cctgagtgtg ctaagatgtc aaaaacccaa acacctccaa atgtagggaa gcccctcctc    3000
atcctcgaca caacgaccaa cgaaacactc acgttcccaa gcgttactgc cgcaggtgct    3060
gctttaggtg tacatttcca acaaatcaat cacaggctca agggtcgaac gtcgcccgac    3120
aaccttattt caaacaggta caaagtgctt gggtacgata ggtaaggttc acaaccct      3180
aaatcctacg aaccaagctc gacggacgtt caaatcccgg ttagagttaa tttatgtaaa    3240
gatttagtaa agacgtatac cattttttctt tacattgtgc ttgcgcagga tttcaggtag  3300
gtctcaaaaa atttgaaaat ttctatattt tggttgtgta atccatttgc acataaccta   3360
tggagacaaa ttatgggtaa gcgaatgact ttcgataccg ccaaatcacg cttttcaagag  3420
aaatttccac atttagaatt gttggagttc agtggcattt ataaaccttc cagtgttaga   3480
tgtcctacgc acggggttgt ccaacttttg tattacgaca cagctataaa gtcaaagtat   3540
gggtgtccgg agtgcgggaa acttaaaatg aaggaaaata cgcctcccca aaaccaaaaa   3600
cctgtctcca tcctcgacac cgccacaggc gaaacactca cgttcccag cgtacaagct    3660
gccgccaaag ccctaaacac cccctacggc tctatacgaa ccaagctcga cggacgttca   3720
aatcccgaca accttgtctg taacaggtat aaggttctgc tataatcaac ctatggaaaa   3780
tattgaagaa tacgcactgc tgtctcccga agccctgctg gaacgcctgg ataccgtttt   3840
gagtatcaga atcggcggca agggttggga atccagttat gaccgccaac tttgcacaga   3900
cgctggtcga aatacaggac agtctgtaca gggttgtgtc aaccgtccaa tacgggatg    3960
acaacctcaa gcggttgaca gcggacaaac ggaagcagta tgagttgaac ttcaagattt   4020
ccgagggttc tacgcgtgta gagtccgact ttaaagagac tttggttcgg ttcggtagag   4080
atatgcttca agatatgccc cctaaaatcc gttcggcaac gctggtagcg ttgacgaccc   4140
tgcttgtcgg agggggcgttg ggttacggtt atttggaata cctgaagcag gttgcttcgg  4200
aagggtatca gaccgagcgt ctgtataatg ccgtcgaccg tcttgcagaa tcccaagaac   4260
ggataacgtc cgccatcctg aagggtgcta gaggtgccga tttcgtgcaa atcggcagac   4320
gttcctacag tagggaggat atatcggagg caaatagacg tgcagagcgt gtcccgtatg   4380
gcgcagagtt ggtttcagac ggcaatttta ccgctgtttt atctgatata ggggattaac   4440
aaaaatcagg acaaggcgac gaagccgcag acagtataaa tagtacgaa ccgattcact    4500
tggtgcttca gcaccttaga gaatcgtttt ctttgagcta aggcgaggca acgccgtact   4560
ggttttttgtt aatccactat attttctgtc cggatacggt ttatcagggt atatcaatgc  4620
```

```
ggcgtatccg gtgcggaaat ggatacggtt ggtgtcggta tggaaacctg atgttttcag    4680
acagcatata caaaaaaccg tactgcttgc gcgtacggtt tttgccgttt caaatcggtt    4740
taaagcgatt tgaggcgggc gatacggttg tccagcgaag ggtgggtgct gagcagggag    4800
tcgcgcgtat ctccggcgat gcccattgcg ttcatttctt cgggcaaatc gaccgggttg    4860
cctttgagcc tttgcagggc ggaaatcatt ttcggcgcgc cgaccagttt tgccgcgccc    4920
gcatcggcgc ggtattcgcg ttgtcggctg aaccacatga caattaagct ggcaaggaag    4980
ccgaacagga tttggaatac catgctgacc aggaaataag ttccctggga ctggctgccg    5040
tcgttgtttc gggcaatcag gttggcaata atgcgcgaca ggaacacgac aaaggtattg    5100
accacgcctt gaatcagcgt cagcgtaacc atatcgccgt tgccgacgtg tgccatttcg    5160
tgcgccaata cggcttccac ttcgtcacgc gtcatatggt cgagcaaacc ggtgctgacg    5220
gcgatcaggg agctgtttct cgatgcgccc gtggcaaagg cattgggttc ggggagtgg    5280 tagatggcga cttcgggcgt tttcaggttc cattgccgcg cttgggcttc gacagtgttc    5340
aaaagccagg cttcttcttc ggtgcgcggc gtgtcgataa cttccgcgcc gaccgattgt    5400
ttggcgataa atttggacat cagcagcgaa ataatcgaac cagtgaagcc gacgacggcg    5460
gaatacgcca acaggctgcc cgtgccgccc cggctgttga tgcccaaaac cgccaaaaca    5520
atgttgatta cgaccaaaac agcgatattg gtagccaaaa acagaaaaat tcgtttcacg    5580
gatgttcctt tttggtaggg tgtgatgttt tgaaattttg ggggattgtc ccaaaaagtt    5640
gccggcttgt gaatatcaga ctcggcaaag gtatgcaaaa catttgcttg caaatggcag    5700
tttgtgcagt tggttttttga actattgtgc caagccgtgt agaatcgtaa accatctgtt    5760
tgattccaat aaacacattt caaaggatca cttcatgaaa gcattacttt taggcgcgcc    5820
gggcgcgggc aaaggcactc aggcgcaatt catcaccgca gcgttcggca ttccgcaaat    5880
ctctaccggc gacatgctcc gtgccgcgat taaggcaggc acgcccttgg gtttggaagc    5940 gaaaaaatc attgacgaag gcggcttggt gcgcgacgac atcattatcg gcatggtcaa    6000
agaacgcatc gcgcaagacg actgcaaaaa cggtttcttg tttgacggtt tcccgcgcac    6060
attggcacaa gccgaagcga tggttgaagc aggcgtggat ttggatgcag tcgttgaaat    6120
cgatgtgcct gacagcgtga ttgtcgaccg catgagcggc cgccgcgtgc atttggcttc    6180
cggccgtact taccacgtta cctacaaccc gcccaaagtt gaaggcaaag acgacgtaac    6240
cggcgaagat ttgattcagc gcgacgacga caaagaagaa accgtgaaaa aacgccttgc    6300
cgtttaccac gagcaaaccg aagttttggt cgattttac agcaaactgg aaggcgaaca    6360
cgcgcctaaa tacatcaaag ttgacggcac ccaagcagta gaagccgtga agccgaagt    6420 attgggcgca ttgggcaaat aaatcgaaaa ggtcgtaccc acgggcaggc ttcgcactct    6480
gaaaacagaa aatcaggttt tcagacgacc tgttttgat aaacagcgtg ttgcaaccga    6540
aaaataatca tttggcgtca ttcccgcgca ggcgggaatc catttctgaa tttgggcaat    6600
cgctgtttaa atctgatgaa ctgagtttta tcaatggatt cccgcctgcg cgggaatgac    6660
ggctgatgta ccggttcaaa tttatccgaa acagtttgtc ggaggcttga gtccgcgtag    6720 gtcgacatc aatgcccgac ctacggtttg aatttacgtt gttatagtgg attaacaaaa    6780
atcaggacaa ggcgacgaag ccgcaggcag tacagatagt acggaaccga ttcactttgt    6840
gcttcagcac cttagagaag cgttctcttt gaactaaggc gagacaacgc cgtaccggtt    6900
taaagttaat ccactatact gcgaaaaaga cgataaaggt cgtctgaaaa cccgaaacga    6960
aaacaccatg aatcctttaa tctccgactt ccaaactccg caacaacgca ccccgttat    7020
```

-continued

```
cgtcgccctt gattttcca acgaaaaaga cacgctcgga ttcgtccgca accttgaccc      7080
gacattgtgt caaatcaaaa tcggcaaaga gctgtttacc gcgacgggac gcaatttggc      7140
agaaagctta atcaatcaag gtttcaaact tttcctcgat ttgaaatacc acgatattcc      7200
ccacaccgtc gcgcaagcct gcaaagtcgc tgccgatatg ggcgtttgga tggtcgatat      7260
gcacgcatcg ggcggccgcc gtatgatgga agccgcagca gaagccgttg ccggatacgg      7320
cacgaagccg ctcttaatcg gcgtaaccgt gttgaccagc atggaacaaa gtgatttggc      7380
ggaaatcggt ttgaacaccg cccctgaaga acaagtcatc cgcttggcaa aactggcgca      7440
aagttcgggc ttggacggcg tggtctgttc cgcccaagaa gccgcgccgc tgcgccgcga      7500
attgggacag gattttgtct tggtcacgcc cggcatccgc ttggacgttg ccggcaataa      7560
tgatgaccag cgccgcatca tgacaccggc cgaagccttg gctgccggtt cgacttattt      7620
ggtaatgggt cgtcctgtaa cccaagctgc cgatccggta ccgtattgc gcgaagtgaa       7680
ccgcgtggca aaccttgaag caaactgatt ttcagacggc cttacaggct gaggccgtct      7740
gaaaaatac aacggaggca atatgtccgc caagttccaa caagaaaccc tcaaatcccg        7800
tttcgcgcaa gccaaagtcc tggttgtcgg cgacgtgatg ctcgaccgct attggttcgg      7860
cgatgtgtcc cgtatttcgc ccgaagcccc cgtgccggtg gcgaaaatcg gacgaatcga      7920
ccaacgcgcg ggcggagcgg caaatgtcgc gcgcaacatc gcttcgttgg gcggcagggc      7980
agggctgttg tccgtaaccg gcaacgacga agccgccgac gcgctcgatg cgctgatggt      8040
gcaggacggc gtcgcctcct atctgatgcg cgacaaacaa atcgccacca ccgtcaaact      8100
gcgcgtcgtc gcccgcaacc agcagcttat ccgtcttgat tttgaagaac atcccaactg      8160
cgaagtgttg gaacaaatca gcagaaata ccgcgaaatc ttgcccgaat cgacgcaat      8220
cattttttca gactacggca aaggcggcct gtcgcatatc tccgatatga tcgattgggc      8280
gaaacacgcc ggcaaaaccg tcttaatcga ccccaaaggc gacgattacg aaaaatatgt      8340
cggtgcaact ctgattacgc ctaaccgcgc cgaattgaaa gaagtggtcg gcagttggaa      8400
aaacgaaagc gagctgaccg aaaaagcgca aaacctgcgc cgccacctcg acctgaccgc      8460
cgttttactg acccgaagcg aagaaggcat gaccttgttc agcgaaggcg aaccgattta      8520
ccagcccacc cgcgcccaag aagtttacga cgtatccggt gcgggcgaca ccgtcattgc      8580
cggaatgggc ttgggtttgg cggcaggctg caccatgccc gaagccatgt accttgccaa      8640
tactgcggcc ggggttgtcg tggcgaaact cggtacggcg gtttgctcgt ttgccgaatt      8700
gatcaaggca ttgtcagggc aatcaacaat gtagttttca tattgataag ataaacagaa      8760
cgatataagt atgactattt cgacaatggc acagacacac gatactcgat tacaaaaaac      8820
tttgctcttt cccagtcaac aaggttggaa atctaaaact tttcttaaac ctgattcaca      8880
tattagatta gcaaccgtat tcagcgggat tggtgcggtt gaacaggcat tccaccgatt      8940
aaatttaaac cataccattg ttttttcagg agatattgat ccatacgtta aaaaagtta       9000
tcttggaaac tataaattaa atgaagattt ttggcataac gacattactc aatttgatgc      9060
gagaaagttt agaaatcaag ttgatatttt agttggaggc agtccttgcc aagcattttc      9120
catggttggc aaacgtgcag gattagaaga tacacgagga acattattct atgaatttgc      9180
tcgcgttgtg gatgaagtcc aaccaaagat atttatttat gaaaatgtaa agggcttgct      9240
taatcatgat aatggaaaaa cttggaaagt tgtaaaaagt gttttttatt cacttggtta      9300
tgacttatat ttccaaataa tgaatagtaa ggattatggg attcctcaac atcgtgagcg      9360
tattttgtt gttggctttc ataccctcc tataaatggt tttcagtttc ctgaaaagat       9420
```

```
tgaattagaa catactatgc aagatttttt ggaggactat actgatagca aatattttt      9480 acgtgaaaag ggtgcgaaat tgttaccag ttctaaaaat agacaaaaac gttatacaca      9540
gattaatgga gaaattgcct tatgccaaaa agcaaatcaa caatttaatt ggcatggtga     9600
ttttattttt caggcagccc gcgaatctga atttgatgac tttattttg atgtaaataa     9660 cgttgaggaa aaatattatc tttctgaaaa aatcaaaaat tatgttttgg caggaggaac    9720
aaaaaatttt aaaaccagta cggaaactga tttgcctgta gctcgcccat tattgcaaac   9780
tatgcataaa atgcatcgtg ccggggttga taattatgtt actcataatc gtggacgtat   9840 tcgtaaaatta acacctaggg aatgtttgcg gctaatgggt tttagagatg attttaaaat  9900
tttagttagt gatactcaaa tgtatcgcca agcgggaaac agtattgttg ttgatgtatt   9960
aatcgctata ttaaaacaaa tggatattac gctttatgga gagtaaaatg ccggattttc  10020
aaagaattac tattgaaaac atagagtatt ttattgtcga tagtattcaa aatttacgtg  10080
cggaagatag ttttattcac aggaataaca agttatctgt ttttggtggt aatggggaag  10140
cacgcaaata tgtaggtagt tatattgatg atagtggtcg aaaactaagt acattttttg  10200
agtatgaaaa ttggggggatt actgagacaa aaaatggaag gagggtagaa tatccttca   10260 ttcagaaaaa ttgtttttt tataagaaaa atttacagcg ttatttggtt gatgcaaaag    10320
ttgaatatca caaacaagaa cagaaatatc atcatgatat ttcaaggttt tatgatgatt  10380
acgttttaag tattaataat ctgcctacag aaaatatttt cttttcaatc catgatgtat  10440
cagaccattt ggaaaattct aaaggttacc gtaggggtta tatccgttcg gaggatgata  10500
tatggtcaat ttggcgtaag attgtattgc ccaaaattag ttatttatca attcttaaac  10560
tattgcctgt caaagataca gaagattcag aaccattatt ttatttccga atattttgg   10620 attatcaatt tcgctctatc gtgcacccgc aactcttatc aagagaaaaa ttagaaatac  10680
cggcttcaga atttaatcaa ttcgtagagc aagaaatcat taaacagaaa agtagaaaag  10740
ggcagcagaa atatcgcaag gatgttataa atcatatgtc gcaatgtcca tttacattaa  10800
ttacagatga gatttttgtta agggctagtc atattaaacc ttatatggtt tgtattactg  10860
agaaaaatga gaaagaggca ttagattatt taaatggggt agctttaacg ccgacttatg  10920
attggttgtt cgatcaaggt tatattactt tcttggatga tggtcgtttg atttgcggta  10980
ctcgactaag ccgttacaca tgggaaaaac ttaatatcaa tccaaatgca aaaaattaag 11040
atgagaatat atcccgaagg aagagaaaaa tatttggaat atcatcgcaa atttgtgttt  11100
caggacaata tcgatgattt cttgtaacta agt                               11133

<210> SEQ ID NO 36
<211> LENGTH: 727
<212> TYPE: DNA
<213> ORGANISM: Neisseria gonorrhoeae

<400> SEQUENCE: 36
cagccgcatc atgatgccgc acgtcagggc ttcgtcttcc gatacctttg cgcccgacaa      60
catccgggcg atgttttct tttgcgcttt tgaccgggcg gacagccggt tccggtcaac      120
gtttctgacc gtcccggcgc gtttgacggc gcgttcctgc cgcgttgatt ccttcgccgc     180
gcgtttggcg gcaagcatct gttttgccgt cggttttgtt gttgccgttt gcatttttac    240
ctccttttaa aactgtttcg acaggcttgc gaacggcctt cccgttcact tcccgcgcct    300
gcctgattcc tacggtgcgg atgtcgggat tgcccggcgg cagcctgaca aacccttcgg   360
cggcccctat ggttggatat ccggggctga ttcggcagcg gctgttgctt ggccgctccc  420
```

```
gtccgcgccg gtctgcgtac cgcttggaat cctctttgtc gcaaacaggc cgccgccgtt      480
tttcttcttc gggacgatgt tttccaaagg ctgcgaacat ggcggcccct gtttatctaa      540
tctgcaaatt cttccgctct tcaatcttcg cgcctgctac ttgccgaccg ctttcaatcg      600
cttttctgat ggcggttttg tccggttcgg ttttgacggc ctcacgcata aattcggcgg      660
ggatttgtgc ttcgtctaag atcacgacgg cttcggattt gcggaacgag gctttaaaag      720
tgccgtc                                                                727

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
gtttcgacag gcttgcgaac                                                   20

<210> SEQ ID NO 38
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
gtttcgacag gcttgcgaa                                                    19

<210> SEQ ID NO 39
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
tttgttgttg ccgtttgca                                                    19

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
cctgtttgcg acaaagagga                                                   20

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
tgcgacaaag aggattccaa                                                   20
```

<210> SEQ ID NO 42
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 42
ttcccgcgcc tgcctgattc cta                                                23

<210> SEQ ID NO 43
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 43
acatccgcac cgtaggaatc aggca                                              25

<210> SEQ ID NO 44
<211> LENGTH: 28
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 44
aatcccgaca tccgcaccgt aggaatca                                           28

<210> SEQ ID NO 45
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 45
aatcccgaca tccgcaccgt aggaat                                             26

<210> SEQ ID NO 46
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
cgtttggcgg caagcatc                                                      18

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
gcggcaagca tctgttttgc                                                    20

<210> SEQ ID NO 48
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 48
gtagcaggcg cgaagattga a                                    21

<210> SEQ ID NO 49
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 49
agtagcaggc gcgaagattg a                                    21

<210> SEQ ID NO 50
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 50
gggcggaaga atttgcagat ta                                   22

<210> SEQ ID NO 51
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 51
gccatcagaa aagcgattga aa                                   22

<210> SEQ ID NO 52
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 52
ggacaaaacc gccatcagaa a                                    21

<210> SEQ ID NO 53
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 53
taatctgcaa attcttccgc ccttcaatct t                         31

```
<210> SEQ ID NO 54
<211> LENGTH: 32
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 54
tttatctaat ctgcaaattc ttccgccctt ca                                    32

<210> SEQ ID NO 55
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 55
caaattcttc cgcccttcaa tcttcgc                                          27

<210> SEQ ID NO 56
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 56
cttcaatctt cgcgcctgct acttgcc                                          27

<210> SEQ ID NO 57
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 57
aagattgaag ggcggaagaa tttgcagatt a                                     31

<210> SEQ ID NO 58
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 58
gcgaagattg aagggcggaa gaatttg                                          27

<210> SEQ ID NO 59
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
tcagggcttc gtcttccga                                                   19
```

```
<210> SEQ ID NO 60
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
tttaaagcct cgttccgcaa                                                   20

<210> SEQ ID NO 61
<211> LENGTH: 727
<212> TYPE: DNA
<213> ORGANISM: Neisseria gonorrhoeae

<400> SEQUENCE: 61
cagccgcatc atgatgccgc acgtcagggc ttcgtcttcc gatacctttg cgcccgacaa       60
catccgggcg atgttttctt tttgcgcttt tgaccgggcg acagccggt tccggtcaac      120 gttttttgacc gtcccggcgc gtttgacggc gcgttcctgc cgcgttgatt ccttcgccgc    180
gcgtttggcg gcaagcatct gttttgccgt cggttttgtt gttgccgttt gcattttttac   240 ctccttttaa aactgtttcg acaggcttgc gaacggcctt cccgttcact tcccgcgcct    300
gcctgattcc tacggtgcgg atgtcgggat tgcccggcgg cagcctgaca aacccttcgg    360
cggcccctac ggccggatat ccggggctga ttcggcagcg gctgttgctt ggccgctccc    420
gtccgcgccg gtctgcgtac cgcttggaat cctctttgtc gcaaacaggc gccgccgtt    480 tttcttcttc ggggcggaat tttccaaagg ctgcgaacat ggcggcccct gtttatctaa    540
tctgcaaatt cttccgctct tcaatcttcg cgcctgctac ttcccgaccg cttttcaatcg   600 cttttctgat ggcggttttg tccggttcgg ttttgacggc ctcacgcata aattcggcag    660
ggatttgtgc ttcgtctaag atcacgacgg cttcggattt gcggaacgag gctttaaaag    720
tgccgtc                                                              727

<210> SEQ ID NO 62
<211> LENGTH: 711
<212> TYPE: DNA
<213> ORGANISM: Neisseria gonorrhoeae

<400> SEQUENCE: 62
gccgcacgtc agggcttcgt cttccgatac ctttgcgccc gacaacatcc gggcgatgtt       60 ttcttttgc gctttgacc gggcggacag ccggttccgg tcaacgtttc tgaccgtccc       120
ggcgcgtttg atggcgcgtt cctgccgcgt tgattccttc gccgcgcgtt tggcggcaag    180
catctgtttt gccgtcggtt tgttgttgc cgtttgcatt tttacctcct tttaaaactg    240
tttcgacagg cttgcgaacg gccttcccgt tcacttcccg cgcctgcctg attcctacgg   300
tgcggatgtc gggattgccc tccggcagcc tgacaaaccc ttcggcggcc cctacggccg    360
gatatccggg gctgattcgg cagcggctgt tgcttggccg ctcccgtccg cgccggtctg    420
cgtaccgctt ggaatcctct ttgtcgcaaa caggccgccg ccgttttttct tcttcgggac    480 gatgttttcc aaaggctgcg aacatggcgg cccctgttta tttaatctgc aaattcttcc    540
gctcttcaat cttcgcgcct gctacttccc gaccgctttc aatcgctttt ctgatggcgg    600
ttttgtccgg ttcggttttg acggtctcac gcataaattc ggcagggatt tgtgcttcgt    660
ctaagatccc gacggcttcg gatttgcgga acgaggctta aaagtgccgt c             711
```

```
<210> SEQ ID NO 63
<211> LENGTH: 647
<212> TYPE: DNA
<213> ORGANISM: Neisseria gonorrhoeae

<400> SEQUENCE: 63
cagccgcatc atgatgccgc acgtcagggc ttcgtcttcc gatacctttg cgcccgacaa      60
catccgggcg atgttttctt tttgcgcttt tgaccgggcg gacagccggt tccggtcaac     120
gttttgccgt cggttttgtt gttgccgttt gcattttttac ctccttttaa aactgtttcg    180
acaggcttgc gaacggcctt cccgttcact tcccgcgcct gcctgattcc tacggtgcgg    240
ctgtcgggat tgccctccgg cagcctgaca aaccccttcgg cggcccctac ggccggatat    300
ccggggctga ttcggcagcg gctgttgctt ggccgctccc gtccgcgccg gtctgcgtac    360
cgcttggaat cctctttgtc gcaaacaggc cgccgccgtt tttcttcttc gggacgatgt    420
tttccaaagg ctgcgaacat ggcggccccct gtttatttaa tctgcaaatt ctgacgctct    480
tcaatcttcg cgcctgctac ttcccgaccg ctttcaatcg cttttctgat ggcggttttg    540
tccggttcgg ttttgacggt ctcacgcata aattcggcag ggatttgtgc ttcgtctaag    600
atcacgacgg cttcggattt gcggaacgag gctttaaaag tgccgtc                  647

<210> SEQ ID NO 64
<211> LENGTH: 727
<212> TYPE: DNA
<213> ORGANISM: Neisseria gonorrhoeae

<400> SEQUENCE: 64
cagccgcatc atgatgccgc acgtcagggc ttcgtcttcc gatacctttg cgccagacaa     60
catccgggcg atgttttctt tttgcgcttt tgaccgggcg gacagccggt tccggtcaac    120
gtttctgacc gtcccggcgc gtttgacggc gcgttcttgc cgcgttgatt ccttcgccgc    180
gcgtttggcg gcaagcatct gttttgccgt cggttttgtt gttgccgttt gcattttttac   240 ctccttttaa aactgtttcg acaggcttgc gaacggcctt cccgttcact tcccgcgcct   300
gcctgattcc tacggtgcgg atgtcgggat tgccctccgg cagcctgaca aaccccttcgg  360 cggcccctac ggccggatat ccggggctga ttcggcagcg gctgttgctt ggccgctccc   420
gtccgcgccg gtctgcgtac cgcttggaat cctctttgtt gcaaacaggc cgccgccgtt   480
tttcttcttc gggacgatgt tttccaaagg ctgcgaacat ggcggcccct gtttatctaa   540
tctgcaaatt cttccgctct tcaatcttcg cgcctgctac ttgccgaccg ctttcaatcg   600
cttttctgat ggcggttttg tccggttcgg ttttgacggc ctcacgcata aattcggcag   660
ggatttgtgc ttcgtctaag atcacgacgg cttcggattt gcggaacgag gctttaaaag   720
tgccgtc                                                             727

<210> SEQ ID NO 65
<211> LENGTH: 806
<212> TYPE: DNA
<213> ORGANISM: Neisseria gonorrhoeae

<400> SEQUENCE: 65
cagccgcatc atgatgccgc acgtcagggc ttcgtcttcc gatacctttg cgcccgacaa     60
catccgggcg atgttttctt tttgcgcttt tgaccgggcg gacagccggt tccggtcaac    120
gtttctgacc gtcccggcgc gtttgacggc gcgttcctgc cgcgttgatt ccttcgccgc   180
gcgtttggcg gcaagcatct gttttgccgt cggttttgtt gctactgttt gcattttgtt   240
ttctcgattt tttgatgccg ttctctcaat gcccaatcat aaagctgtat ctctcacgag   300
```

-continued

```
gtcgccgaat ttaaattgat agttcatgtc ttgttccatt aatatcaaac gcaatcttca      360
aacacctcaa ttcattttt taaatcgcta ataccataat ttattacatc ctttagaaat      420
tccaaagagg tatccgcttc gtctgcttta tccctaattt cgtctatata accctctaac      480
gattcaggct cttttaatgc ttctttgcat aagttatcta ttacccttaa tgcgtttttt      540
acatcttcca aatagctcat tttttgctcc ttaactcaaa atgggatgct gtcgtcaaca      600
tcttctacgg tttatctaat ctgcaaattc ttccgccctt caatcttcgc gcctgctact      660
tgccgaccgc tttcaatcgc ttttctgatg gcggttttgt ccggttcggt tttgacggcc      720
tcacgcataa attcggcggg gatttgtgct cgtctaaga tcacgacggc ttcggatttg      780
cggaacgagg ctttaaaagt gccgtc                                          806
```

<210> SEQ ID NO 66
<211> LENGTH: 800
<212> TYPE: DNA
<213> ORGANISM: Neisseria gonorrhoeae

<400> SEQUENCE: 66

```
catcatgatg ccgcacgtca gggcttcgtc ttccgatacc tttgcgcccg acaacatccg       60
ggcgatgttt tcttttttgcg cttttgaccg ggcggacagc cggttccggt caacgttttt      120
tactgttccc gcgcgtttga cggcgcgttc ctgccgcgtt gattccttcg ccgcgcgttt      180
ggcggcaagc atctgttttg ccgtcggttt tgttgctact gtttgcattt tgttttctcg      240
attttttgat gccgttctct caatgcccaa tcataaagct gtatctctca cggggtcgcc      300
gaatttaaat tgatagttca tgtcttgttc cattaatatc aaacgcaatc ttcaaacacc      360
tcaattacat tttttaaatc gctaatacca taatttatta catcctttag aaattccaaa      420
gaggtatccg cttcgtctgc tttatcccta atttcgtcta tataaccctc taacgattca      480
ggctctttta atgcttcttt gcataagtta tctattaccc ttaatgcgtt ttttacatct      540
tccaaatagc tcatttttg ctccttaact caaaatggga tgctgtcgtc aacatcttct      600
acggtttatc taatctgcaa attcttccgc ccttcaatct tcgcgcctgc tacttgccga      660
ccgctttcaa tcgcttttct gatggcggtt ttgtccggtt cggttttgac ggcctcacgc      720
ataaattcgg cggggatttg tgcttcgtct aagatcacga cggcttcgga tttgcggaac      780
gaggctttaa aagtgccgtc                                                 800
```

<210> SEQ ID NO 67
<211> LENGTH: 806
<212> TYPE: DNA
<213> ORGANISM: Neisseria gonorrhoeae

<400> SEQUENCE: 67

```
cagccgcatc atgatgccgc acgtcagggc ttcgtcttcc gatacctttg cgcccgacaa       60
catccgggcg atgttttctt tttgcgcttt tgaccgggcg acagccggt tccggtcaac      120
gttttttkacy gtyccsgcgc gtttgacggc gcgttcctgc cgcgttgatt ccttcgccgc      180
gcgtttggcg gcaagcatct gttttgccgt cggtyttgtt gctactgttt gcattttgtt      240
ttctcgattt tttgatgccg ttctctcaat gcccaatcat aaagctgtat ctctcacgag      300
gtcgccgaat ttaaattgat agttcatgtc ttgttccatt aatatcaaac gcmatcttca      360
aacacctcaa ttcattttt taaatcgcta ataccatmat ttattacatc ctttagaaat      420
tccaaagagg tatccgcttc gtctrcttta tccctaattt cgtctatata ayectctaac      480
gattcaggct cttttaatgc ttctttgcat aagttatcta ttacccttaa tgcgtttttt      540
```

```
acatcttcca aatagctcat tttttgctcc ttaactcaaa atgggatgct gtcgtcaaca      600
tcttctacgg tttatctaat ctgcaaattc tkmcgctctt caatcttcgc gcctgctact      660
tgccgaccgc tttcaatcgc ttttctgatg gcggttttgt ccggttcggt tttgacggcc      720
tcacgcataa attcggcagg gatttgtgct tcgtctaaga tcacgacggc ttcggatttg      780
cggaacgagg ctttaaaagt gccgtc                                           806

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
tcaatcttcg cgcctgctac                                                   20

<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
aaagcctcgt tccgcaaatc                                                   20

<210> SEQ ID NO 70
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 70
aaaccgaacc ggacaaaacc gccat                                             25
```